United States Patent
Wizel et al.

(10) Patent No.: US 8,765,148 B2
(45) Date of Patent: Jul. 1, 2014

(54) IC31 NANOPARTICLES

(75) Inventors: Benjamin Wizel, San Diego, CA (US); Karin Riedl, Krems (AT); Karen Lingnau, Vienna (AT); Ursula Schlosser, Uttendorf (AT); Jürgen Wruss, Vienna (AT); Robert Schlegl, Siegenfeld (AT); Michael Weber, Vienna (AT); Christoph Reinisch, Siegenfeld (AT); Ljubomir Paucz, Vienna (AT); Christoph Klade, Wr. Neustadt (AT); Jee Loon Look, Boyds, MD (US); Christian Ruiz, Gaithersburg, MD (US); Robert Seid, Chapel Hill, NC (US)

(73) Assignee: Valneva Austria GmbH, Vienna (AT)

( * ) Notice: Subject to any disclaimer, the term of this patent is extended or adjusted under 35 U.S.C. 154(b) by 0 days.

(21) Appl. No.: 13/578,686

(22) PCT Filed: Feb. 21, 2011

(86) PCT No.: PCT/EP2011/052496
§ 371 (c)(1),
(2), (4) Date: Aug. 13, 2012

(87) PCT Pub. No.: WO2011/101465
PCT Pub. Date: Aug. 25, 2011

(65) Prior Publication Data
US 2012/0308618 A1 Dec. 6, 2012

Related U.S. Application Data

(60) Provisional application No. 61/306,338, filed on Feb. 19, 2010.

(51) Int. Cl.
*A61K 39/39* (2006.01)
*A61K 9/14* (2006.01)
*A61K 9/51* (2006.01)
*A61K 39/40* (2006.01)
*A61K 39/42* (2006.01)

(52) U.S. Cl.
CPC . *A61K 39/39* (2013.01); *A61K 9/51* (2013.01); *A61K 39/40* (2013.01); *A61K 39/42* (2013.01)
USPC .................. 424/278.1; 424/184.1; 424/499

(58) Field of Classification Search
None
See application file for complete search history.

(56) References Cited

U.S. PATENT DOCUMENTS 6,534,065 B1 * 3/2003 Makin et al. .............. 424/206.1
6,869,607 B1 * 3/2005 Buschle et al. ............ 424/184.1

FOREIGN PATENT DOCUMENTS

| DE | 19803453 C | 8/1999 |
|---|---|---|
| WO | WO-97/19169 A1 | 5/1997 |
| WO | WO-97/30721 A1 | 8/1997 |
| WO | WO-99/20301 A1 | 4/1999 |
| WO | WO-99/38528 A3 | 12/1999 |
| WO | WO-01/93905 A1 | 12/2001 |
| WO | WO-02/32451 A1 | 4/2002 |
| WO | WO-02/053184 A3 | 7/2002 |
| WO | WO-02/053185 A3 | 7/2002 |
| WO | WO-02/059148 A3 | 8/2002 |
| WO | WO-02/066621 A1 | 8/2002 |
| WO | WO-2004/024182 A3 | 3/2004 |
| WO | WO-2004/084937 A1 | 10/2004 |
| WO | WO-2004/084938 A1 | 10/2004 |
| WO | WO 2004084938 A1 * | 10/2004 |
| WO | WO-2005/004910 A2 | 1/2005 |
| WO | WO-2006/045677 A1 | 5/2006 |
| WO | WO-2007/121491 A8 | 11/2007 |
| WO | WO-2008/031126 A1 | 3/2008 |
| WO | WO-2010/015701 | 2/2010 |

OTHER PUBLICATIONS

Kamath et al., Adult-like anti-mycobacterial T cell and in vivo dendritic cell responses following neonatal immunization with Ag85B-ESAT-6 in the IC31 adjuvant. PLoS One. 2008;3(11):e3683. Epub Nov. 10, 2008.
Kamath et al., Protective anti-mycobacterial T cell responses through exquisite in vivo activation of vaccine-targeted dendritic cells. Eur J Immunol. May 2008;38(5):1247-56.
Lingnau et al., IC31 and IC30, novel types of vaccine adjuvant based on peptide delivery systems. Expert Rev Vaccines. Oct. 2007;6(5):741-6.
Olafsdottir et al., IC31, a two-component novel adjuvant mixed with a conjugate vaccine enhances protective immunity against pneumococcal disease in neonatal mice. Scand J Immunol. Mar. 2009;69(3):194-202.
Riedl et al.,The novel adjuvant IC31 strongly improves influenza vaccine-specific cellular and humoral immune responses in young adult and aged mice. Vaccine. Jun. 25, 2008;26(2728):3461-8. Epub May 5, 2008.
Schellack et al., IC31, a novel adjuvant signaling via TLR9, induces potent cellular and humoral immune responses. Vaccine. Jun. 29, 2006;24(26):5461-72. Epub Apr. 7, 2006.

* cited by examiner

*Primary Examiner* — H. Sarah Park
(74) *Attorney, Agent, or Firm* — Wolf, Greenfield & Sacks, P.C.

(57) ABSTRACT

The invention discloses pharmaceutical compositions in liquid form comprising a peptide with the amino acid sequence KLKL$_5$KLK and an oligodeoxynucleotide with the nucleic acid sequence (dIdC)$_{13}$ and wherein the peptide and the oligodeoxynucleotide are present as sterile-filterable nanoparticles in the composition, thereby forming a suspension, characterized in that the mean particle size of the solid particles is less than 1 μm.

10 Claims, 18 Drawing Sheets

SEQUENCE LISTING

```
<160> NUMBER OF SEQ ID NOS: 9

<210> SEQ ID NO 1
<211> LENGTH: 11
<212> TYPE: PRT
<213> ORGANISM: Artificial sequence
<220> FEATURE:
<223> OTHER INFORMATION: peptide derived from Sapecin B
<220> FEATURE:
<221> NAME/KEY: PEPTIDE
<222> LOCATION: (1)..(11)
<223> OTHER INFORMATION: "KLK"

<400> SEQUENCE: 1

Lys Leu Lys Leu Leu Leu Leu Leu Lys Leu Lys
1               5                   10

<210> SEQ ID NO 2
<211> LENGTH: 26
<212> TYPE: DNA
<213> ORGANISM: Artificial sequence
```

```
<220> FEATURE:
<223> OTHER INFORMATION: oligo-d(IC)13
<220> FEATURE:
<221> NAME/KEY: misc_feature
<222> LOCATION: (1)..(1)
<223> OTHER INFORMATION: n is deoxyinosine
<220> FEATURE:
<221> NAME/KEY: misc_feature
<222> LOCATION: (3)..(3)
<223> OTHER INFORMATION: n is deoxyinosine
<220> FEATURE:
<221> NAME/KEY: misc_feature
<222> LOCATION: (5)..(5)
<223> OTHER INFORMATION: n is deoxyinosine
<220> FEATURE:
<221> NAME/KEY: misc_feature
<222> LOCATION: (7)..(7)
<223> OTHER INFORMATION: n is deoxyinosine
<220> FEATURE:
<221> NAME/KEY: misc_feature
<222> LOCATION: (9)..(9)
<223> OTHER INFORMATION: n is deoxyinosine
<220> FEATURE:
<221> NAME/KEY: misc_feature
<222> LOCATION: (11)..(11)
<223> OTHER INFORMATION: n is deoxyinosine
<220> FEATURE:
<221> NAME/KEY: misc_feature
<222> LOCATION: (13)..(13)
<223> OTHER INFORMATION: n is deoxyinosine
<220> FEATURE:
<221> NAME/KEY: misc_feature
<222> LOCATION: (15)..(15)
<223> OTHER INFORMATION: n is deoxyinosine
<220> FEATURE:
<221> NAME/KEY: misc_feature
<222> LOCATION: (17)..(17)
<223> OTHER INFORMATION: n is deoxyinosine
<220> FEATURE:
<221> NAME/KEY: misc_feature
<222> LOCATION: (19)..(19)
<223> OTHER INFORMATION: n is deoxyinosine
<220> FEATURE:
<221> NAME/KEY: misc_feature
<222> LOCATION: (21)..(21)
<223> OTHER INFORMATION: n is deoxyinosine
<220> FEATURE:
<221> NAME/KEY: misc_feature
<222> LOCATION: (23)..(23)
<223> OTHER INFORMATION: n is deoxyinosine
<220> FEATURE:
<221> NAME/KEY: misc_feature
<222> LOCATION: (25)..(25)
<223> OTHER INFORMATION: n is deoxyinosine

<400> SEQUENCE: 2
ncncncncnc ncncncncnc ncncnc                                      26

<210> SEQ ID NO 3
<211> LENGTH: 251
<212> TYPE: PRT
<213> ORGANISM: Streptococcus pneumoniae
<220> FEATURE:
<221> NAME/KEY: PEPTIDE
<222> LOCATION: (1)..(251)
<223> OTHER INFORMATION: "SP2216-1" IC47 antigen

<400> SEQUENCE: 3

Glu Thr Thr Asp Asp Lys Ile Ala Ala Gln Asp Asn Lys Ile Ser Asn
1               5                   10                  15

Leu Thr Ala Gln Gln Gln Glu Ala Gln Lys Gln Val Asp Gln Ile Gln
            20                  25                  30

Glu Gln Val Ser Ala Ile Gln Ala Glu Gln Ser Asn Leu Gln Ala Glu
        35                  40                  45
```

-continued

Asn Asp Arg Leu Gln Ala Glu Ser Lys Lys Leu Glu Gly Glu Ile Thr
    50                  55                  60

Glu Leu Ser Lys Asn Ile Val Ser Arg Asn Gln Ser Leu Glu Lys Gln
65                  70                  75                  80

Ala Arg Ser Ala Gln Thr Asn Gly Ala Val Thr Ser Tyr Ile Asn Thr
                85                  90                  95

Ile Val Asn Ser Lys Ser Ile Thr Glu Ala Ile Ser Arg Val Ala Ala
            100                 105                 110

Met Ser Glu Ile Val Ser Ala Asn Asn Lys Met Leu Glu Gln Gln Lys
        115                 120                 125

Ala Asp Lys Lys Ala Ile Ser Glu Lys Gln Val Ala Asn Asn Asp Ala
    130                 135                 140

Ile Asn Thr Val Ile Ala Asn Gln Gln Lys Leu Ala Asp Asp Ala Gln
145                 150                 155                 160

Ala Leu Thr Thr Lys Gln Ala Glu Leu Lys Ala Ala Glu Leu Ser Leu
                165                 170                 175

Ala Ala Glu Lys Ala Thr Ala Gly Glu Lys Ala Ser Leu Leu Glu
            180                 185                 190

Gln Lys Ala Ala Ala Glu Ala Glu Ala Arg Ala Ala Val Ala Glu
        195                 200                 205

Ala Ala Tyr Lys Glu Lys Arg Ala Ser Gln Gln Ser Val Leu Ala
    210                 215                 220

Ser Ala Asn Thr Asn Leu Thr Ala Gln Val Gln Ala Val Ser Glu Ser
225                 230                 235                 240

Ala Ala Ala Pro Val Arg Ala Lys Val Arg Pro
                245                 250

<210> SEQ ID NO 4
<211> LENGTH: 315
<212> TYPE: PRT
<213> ORGANISM: Streptococcus pneumoniae
<220> FEATURE:
<221> NAME/KEY: PEPTIDE
<222> LOCATION: (1)..(315)
<223> OTHER INFORMATION: "SP1732-3" IC47 antigen

<400> SEQUENCE: 4

Tyr Leu Ile Leu Leu Ala Ser Leu Val Leu Ala Ala Ser Leu Ile
1               5                   10                  15

Trp Ile Leu Ser Arg Thr Pro Ala Thr Ile Ala Ile Pro Asp Val Ala
                20                  25                  30

Gly Gln Thr Val Ala Glu Ala Lys Ala Thr Leu Lys Lys Ala Asn Phe
            35                  40                  45

Glu Ile Gly Glu Glu Lys Thr Glu Ala Ser Glu Lys Val Glu Glu Gly
        50                  55                  60

Arg Ile Ile Arg Thr Asp Pro Gly Ala Gly Thr Gly Arg Lys Glu Gly
65                  70                  75                  80

Thr Lys Ile Asn Leu Val Val Ser Ser Gly Lys Gln Ser Phe Gln Ile
                85                  90                  95

Ser Asn Tyr Val Gly Arg Lys Ser Asp Val Ile Ala Glu Leu Lys
            100                 105                 110

Glu Lys Lys Val Pro Asp Asn Leu Ile Lys Ile Glu Glu Glu Ser
        115                 120                 125

Asn Glu Ser Glu Ala Gly Thr Val Leu Lys Gln Ser Leu Pro Glu Gly
        130                 135                 140

```
Thr Thr Tyr Asp Leu Ser Lys Ala Thr Gln Ile Val Leu Thr Val Ala
145                 150                 155                 160

Lys Lys Ala Thr Thr Ile Gln Leu Gly Asn Tyr Ile Gly Arg Asn Ser
                165                 170                 175

Thr Glu Val Ile Ser Glu Leu Lys Gln Lys Val Pro Glu Asn Leu
            180                 185                 190

Ile Lys Ile Glu Glu Glu Ser Glu Ser Glu Pro Gly Thr Ile
        195                 200                 205

Met Lys Gln Ser Pro Gly Ala Gly Thr Thr Tyr Asp Val Ser Lys Pro
210                 215                 220

Thr Gln Ile Val Leu Thr Val Ala Lys Lys Val Thr Ser Val Ala Met
225                 230                 235                 240

Pro Ser Tyr Ile Gly Ser Ser Leu Glu Phe Thr Lys Asn Asn Leu Ile
                245                 250                 255

Gln Ile Val Gly Ile Lys Glu Ala Asn Ile Glu Val Val Glu Val Thr
                260                 265                 270

Thr Ala Pro Ala Gly Ser Val Glu Gly Met Val Val Glu Gln Ser Pro
                275                 280                 285

Arg Ala Gly Glu Lys Val Asp Leu Asn Lys Thr Arg Val Lys Ile Ser
290                 295                 300

Ile Tyr Lys Pro Lys Thr Thr Ser Ala Thr Pro
305                 310                 315

<210> SEQ ID NO 5
<211> LENGTH: 289
<212> TYPE: PRT
<213> ORGANISM: Streptococcus pneumoniae
<220> FEATURE:
<221> NAME/KEY: PEPTIDE
<222> LOCATION: (1)..(289)
<223> OTHER INFORMATION: "SP1650" IC47 antigen

<400> SEQUENCE: 5

Ala Ser Gly Lys Lys Asp Thr Thr Ser Gly Gln Lys Leu Lys Val Val
1               5                   10                  15

Ala Thr Asn Ser Ile Ile Ala Asp Ile Thr Lys Asn Ile Ala Gly Asp
                20                  25                  30

Lys Ile Asp Leu His Ser Ile Val Pro Ile Gly Gln Asp Pro His Glu
            35                  40                  45

Tyr Glu Pro Leu Pro Glu Asp Val Lys Lys Thr Ser Glu Ala Asp Leu
        50                  55                  60

Ile Phe Tyr Asn Gly Ile Asn Leu Glu Thr Gly Gly Asn Ala Trp Phe
65                  70                  75                  80

Thr Lys Leu Val Glu Asn Ala Lys Lys Thr Glu Asn Lys Asp Tyr Phe
                85                  90                  95

Ala Val Ser Asp Gly Val Asp Val Ile Tyr Leu Glu Gly Gln Asn Glu
            100                 105                 110

Lys Gly Lys Glu Asp Pro His Ala Trp Leu Asn Leu Glu Asn Gly Ile
        115                 120                 125

Ile Phe Ala Lys Asn Ile Ala Lys Gln Leu Ser Ala Lys Asp Pro Asn
130                 135                 140

Asn Lys Glu Phe Tyr Glu Lys Asn Leu Lys Glu Tyr Thr Asp Lys Leu
145                 150                 155                 160

Asp Lys Leu Asp Lys Glu Ser Lys Asp Lys Phe Asn Lys Ile Pro Ala
                165                 170                 175
```

```
Glu Lys Lys Leu Ile Val Thr Ser Glu Gly Ala Phe Lys Tyr Phe Ser
                180                 185                 190

Lys Ala Tyr Gly Val Pro Ser Ala Tyr Ile Trp Glu Ile Asn Thr Glu
            195                 200                 205

Glu Glu Gly Thr Pro Glu Gln Ile Lys Thr Leu Val Glu Lys Leu Arg
        210                 215                 220

Gln Thr Lys Val Pro Ser Leu Phe Val Glu Ser Ser Val Asp Asp Arg
225                 230                 235                 240

Pro Met Lys Thr Val Ser Gln Asp Thr Asn Ile Pro Ile Tyr Ala Gln
                245                 250                 255

Ile Phe Thr Asp Ser Ile Ala Glu Gln Gly Lys Glu Gly Asp Ser Tyr
            260                 265                 270

Tyr Ser Met Met Lys Tyr Asn Leu Asp Lys Ile Ala Glu Gly Leu Ala
        275                 280                 285

Lys
```

<210> SEQ ID NO 6
<211> LENGTH: 9
<212> TYPE: PRT
<213> ORGANISM: Artificial sequence
<220> FEATURE:
<223> OTHER INFORMATION: Melanoma epitope
<220> FEATURE:
<221> NAME/KEY: PEPTIDE
<222> LOCATION: (1)..(9)
<223> OTHER INFORMATION: "TRP-2"

<400> SEQUENCE: 6

```
Ser Val Tyr Asp Phe Phe Val Trp Leu
1               5
```

<210> SEQ ID NO 7
<211> LENGTH: 8
<212> TYPE: PRT
<213> ORGANISM: Artificial sequence
<220> FEATURE:
<223> OTHER INFORMATION: Ovalbumin epitope
<220> FEATURE:
<221> NAME/KEY: PEPTIDE
<222> LOCATION: (1)..(8)
<223> OTHER INFORMATION: "OVA 257-264"

<400> SEQUENCE: 7

```
Ser Ile Ile Asn Phe Glu Lys Leu
1               5
```

<210> SEQ ID NO 8
<211> LENGTH: 15
<212> TYPE: PRT
<213> ORGANISM: Chlamydia pneumoniae
<220> FEATURE:
<221> NAME/KEY: PEPTIDE
<222> LOCATION: (1)..(15)
<223> OTHER INFORMATION: "CopN 226-240"

<400> SEQUENCE: 8

```
Asp Arg Tyr Thr Tyr Gln Asp Met Ala Ile Val Ser Ser Phe Leu
1               5                   10                  15
```

<210> SEQ ID NO 9
<211> LENGTH: 10
<212> TYPE: PRT
<213> ORGANISM: Artificial sequence
<220> FEATURE:
<223> OTHER INFORMATION: Lung cancer-derived epitope

```
<220> FEATURE:
<221> NAME/KEY: PEPTIDE
<222> LOCATION: (1)..(10)
<223> OTHER INFORMATION: "SVN 19-28"

<400> SEQUENCE: 9

Ile Ala Thr Phe Lys Asn Trp Pro Phe Leu
1               5                   10
```

IC31 NANOPARTICLES

RELATED APPLICATIONS

This application is a national stage filing under 35 U.S.C. §371 of international application PCT/EP2011/052496, filed Feb. 21, 2011, which was published under PCT Article 21(2) in English, and claims the benefit under 35 U.S.C. §119(e) of U.S. provisional application Ser. No. 61/306,338, filed Feb. 19, 2010, the disclosures of which are incorporated by reference herein in their entireties.

The present invention relates to pharmaceutical compositions, especially to immunogenic compositions, and methods of producing such compositions.

Vaccination is generally considered to be the most efficient and cost-effective method of preventing infectious diseases. With the introduction of adjuvants (compounds that stimulate the immune system and increase the response to a vaccine, without having any specific antigenic effect in themselves) the quality, efficacy and sustainability of the immune response generated by vaccines was significantly improved.

Until very recently, however, the only adjuvant widely used in registered vaccines was alum (aluminium salts). Many adjuvants with superior potency compared to alum are unacceptable for medical use due to toxic side effects (e.g. complete and incomplete Freund's adjuvant). However, a variety of novel and well-tolerated adjuvants are currently being tested in the clinic.

One of the most promising Th1-type adjuvants is known under the name IC31® (WO 04/084938 A). IC31® comprises two synergising components: a synthetic antimicrobial peptide, KLK (SEQ ID NO 1; herein also referred to as KLK peptide or KLKL$_5$KLK; see also WO 02/32451 A) and an oligodeoxynucleotide acting as a TLR9 agonist, ODN1a (SEQ ID NO 2; herein also referred to as (dIdC)$_{13}$, oligo-d (IC)$_{13}$ or oligo-(dIdC)$_{13}$; see also WO 01/93905 A). Upon mixing, KLK and ODN1a form a stable complex via ionic and hydrophobic interactions and, in combination with an antigen, provide immune stimulation via the TLR9/MyD88 pathway, activation of dendritic cells and the promotion of potent antigen-specific cellular and humoral immune responses (Lingnau et al., Expert Rev. Vaccines 6 (2007), 741-746).

IC31® has been tested successfully in a number of vaccination strategies (Lingnau et al., Expert Rev. Vaccines 6 (2007), 741-746; Kamath et al., Eur. J. Immunol. 38 (2008), 1247-1256; Riedl et al., Vaccine 26 (2008), 3461-3468; Schellack et al., Vaccine 24 (2006), 5461-5472; Kamath et al., PlosOne 11 (2008), Olafsdottir et al., Scan. J. Immunol. 69 (2009), 194-202; WO 2004/084938 A; WO 02/053185 A; WO 02/053184 A; WO 2004/084937 A).) Vaccines against influenza, tuberculosis, Group B meningococcus and HCV are currently being developed with IC31® as an adjuvant.

As indicated above, numerous reports are available regarding IC31®-containing vaccines; however, one aspect of the production process of this adjuvant was not considered in the prior art: when KLK and ODN1a are mixed under the previously specified conditions to generate IC31®, a precipitate is immediately formed. Since this suspension cannot be sterile filtered through a 0.2 µm filter, the two components are first dissolved separately in aqueous solutions (i.e., KLK in water; ODN1a in Tris/NaCl or phosphate/NaCl buffer) and sterile filtered before mixing. Once the two components are mixed, the precipitate forms; consequently, all subsequent formulation steps must be performed under aseptic conditions (see FIG. 1). This necessity complicates the production process of IC31®-containing compositions significantly.

It is therefore an object of the present invention to provide nanoparticulate IC31®-containing pharmaceutical compositions and improved methods for producing such compositions which do not encompass the disadvantages in the production process described above for classical IC31® formulations.

Therefore, the present invention provides a pharmaceutical composition in liquid form comprising KLK peptide and ODN1a, wherein the peptide and the oligodeoxynucleotide are present as stable nanoparticles in a suspension, characterized in that the mean particle size of the complexes comprising the peptide with the amino acid sequence KLKL$_5$KLK and the oligodeoxynucleotide with the nucleic acid sequence (dIdC)$_{13}$, herein referred to as IC31® complexes, is less than 1 µm, preferably less than 0.8 µm, more preferably less than 0.7 µm, even more preferably less than 0.5 µm, still more preferably less than 0.2 µm, and most preferably less than 0.1 µm.

The term 'mean particle size' as used throughout the present specification shall mean that 50% of all particles of the IC31® complexes (composed of KLK and ODN1a) present in the composition have a diameter larger than that given value, and 50% have a diameter smaller than that given value. The mean particle size according to the present invention, especially for the above definition, is preferably determined by dynamic light scattering (DLS).

The term 'nanoparticle' or 'nanoparticulate' as used throughout the present specification shall mean that the mean particle size is less than 1 µm, preferably less than 0.8 µm, more preferably less than 0.7 µm, even more preferably less than 0.5 µm, still more preferably less than 0.2 µm, and most preferably less than 0.1 µm.

In a preferred embodiment, at least 90% of all IC31® complexes (composed of KLK and ODN1a) in the composition have a diameter of less than 1 µm.

The term 'stable' as used throughout the present specification shall mean that the mean particle size of the IC31® composition remains less than 1 µm, preferably less than 0.8 µm, more preferably less than 0.7 µm, even more preferably less than 0.5 µm, still more preferably less than 0.2 µm, and most preferably less than 0.1 µm, for at least 2 days, preferably at least 3 days, more preferably for at least 5 days, even more preferably for at least 21 days, even more preferably for at least 50 days, still more preferably for at least 57 days, more preferably for at least 200 days, most preferably for at least one year stored at 2° C. to 8° C., preferably at 4° C., or even more preferred at room temperature (RT). In a preferred embodiment, the mean particle size increase is less than 2 fold of the initial mean particle size for at least 2 days, preferably at least 3 days, more preferably for at least 5 days, even more preferably for at least 21 days, even more preferably for at least 50 days, still more preferably for at least 57 days, more preferably for at least 200 days, and most preferably for at least one year stored at 2° C. to 8° C., preferably at 4° C., or even more preferred at room temperature (RT). The initial mean particle size may be determined directly after formulation of the nanoparticulate IC31® compositions according to the invention or shortly thereafter, for example, within 24 hours after formulation, preferably within 12 hours.

The term 'room temperature' as used throughout the present invention shall mean 18° C. to 26° C., preferably 22° C. to 25° C.

In a preferred embodiment, at least 90% of the particles in IC31® nanoparticle compositions remain less than 1 µm, preferably less than 0.8 µm, more preferably less than 0.7 µm, even more preferably less than 0.5 µm, still more preferably less than 0.2 µm, and most preferably less than 0.1 µm, for at least 2 days, preferably for at least 3 days, more preferably for at least 5 days, even more preferably for at least 21 days, even more preferably for at least 50 days, still more preferably for at least 57 days, more preferably for at least 200 days, and most preferably for at least one year.

In another preferred embodiment, the stable IC31® nanoparticle compositions have a mean particle size of less than 0.2 μm for at least 2 days, preferably for at least 3 days, more preferably for at least 5 days, even more preferably for at least 21 days, even more preferably for at least 50 days, still more preferably for at least 57 days, more preferably for at least 200 days, and most preferably for at least one year. Due to the sustained small particle size, sedimentation of any such stable nanoparticle compositions is not detectable for at least 2 days, preferably for at least 3 days, more preferably for at least 5 days, even more preferably for at least 21 days, even more preferably for at least 50 days, still more preferably for at least 57 days, more preferably for at least 200 days, and most preferably for at least one year.

In a preferred embodiment, the nanoparticulate IC31® compositions are filterable through a 0.4 μm filter. The term 'filterable' as used throughout the present specification shall mean that at least 60%, more preferably at least 65%, 70%, 75%, 80%, 85%, 90%, 95%, most preferably at least 100% of both of the components of IC31® can be recovered from the filtrate after having passed through the filter. Recovery is determined preferably by High Performance Liquid Chromatography (HPLC), especially for the above definition of the term 'filterable'. In an even more preferred embodiment, the nanoparticulate IC31® compositions are sterile-filterable through a 0.2 μm filter, i.e. at least 60%, more preferably at least 65%, 70%, 75%, 80%, 85%, 90%, 95%, most preferably at least 100% of both of the components of IC31® can be recovered from the filtrate after having passed through the 0.2 μm filter.

With the present invention, a nanoparticulate composition of IC31® is provided, which is a suspension of IC31® complexes that have a mean particle size of less than 1 μm, preferably less than 0.8 μm, more preferably less than 0.7 μm, even more preferably less than 0.5 μm, still more preferably less than 0.2 μm, and most preferably less than 0.1 μm, hereinafter shall be referred to as 'nanoparticulate IC31®'. It was already known that, due to the size of the particles formed in classical IC31® formulations, which have a mean particle size of 5 to 50 μm, sterile filtration of these formulations is not possible. Therefore, other methods of sterilisation commonly used in the art were tested on classical IC31® formulations, including γ-irradiation and autoclaving. It was found that these sterilisation techniques cannot be applied to the final IC31® composition due to partial destruction of KLK and ODN1a by such methods. Therefore, further investigations focused on reducing the particle size in IC31®-containing preparations to generate sterile-filterable nanoparticulate compositions; i.e., with a mean particle size of less than 1 μm, preferably less than 0.2 μm. Unfortunately, the techniques for providing nanoparticles which are usually applied, such as high pressure homogenization and sonication, also turned out to be unsuitable for classical IC31®.

Upon continued investigation, it was found that lowering the ionic strength of the classical IC31® composition led to decreased precipitation; however, the low ionic strength alone did not result in a stable nanoparticulate composition which could be used for reproducible preparations suitable for sterile filtration, as KLK and ODN1a were removed by filtration of the formulations. Moreover, a further reduction of ionic strength, i.e. an IC31® composition without ions or buffers, upon sterile filtration, revealed that ODN1a was not detectable in the filtrate. This can be explained as KLK and ODN1a forming a complex immediately after mixing resulting in increased turbidity. This KLK/ODN1a complex forms particles that are removed by the filtration. As the most preferred molar ratio in classical IC31® is 25(KLK):1(ODN1a), all ODN1a present is complexed with KLK, whereas excess KLK remains free in the supernatant and is not retained by a filter. This would also apply to any such other low ionic strength IC31® composition, in which KLK is present in significant excess of ODN1a, e.g. of 10:1 to 100:1, or of 20:1 to 50:1. This result indicated that lowering of the ionic strength alone is not sufficient to generate a stable nanoparticulate IC31® composition.

Accordingly, it became surprisingly apparent that it was possible to obtain a suitable nanoparticulate IC31® composition by using a lower ionic strength if an energy input was applied to the formulation after mixing KLK and ODN1a. The energy input can be supplied e.g. as a moderate heating step, processing by homogenization or sonication, or a combination thereof, e.g. a heating step followed by a homogenization and/or sonication step. However, any homogenization or sonication step inherently comprises a heating step as well, since each homogenization or sonication cycle results in a temperature increase. Thus, an according homogenization or sonication step alone would also result in nanoparticulate IC31® compositions according to the present invention, as long as the required amount of energy is provided. These energy-adding steps and their conditions should be designed to not have a detrimental impact on the composition, especially if the composition comprises additional active ingredients, such as e.g. one or more antigens. The conditions described in the present specification are not detrimental to IC31® or its components. Based on the description of the present invention and the nature of the additional components of the composition, a person skilled in the art can readily design appropriate energy input steps and conditions for the particular composition of interest, e.g. further comprising one or more specific antigens. In compositions with an appropriately reduced ionic strength, energy input in the range of moderate heating—e.g. in a water bath at 40° C., 43° C., 45° C., 50° C. or 55° C. and the like—or by an according homogenization or sonication step, is sufficient to generate the appropriate particle sizes in the IC31® composition which even allows for sterile filtration. As further specified below for IC31® formulated in Water For Injection (herein also referred to as "WFI"), more energy is required to result in nanoparticles than for compositions having low ionic strength; thus, either a more intense heating, homogenization, or sonication step would be needed, or more than one energy input step could be combined (e.g. a heating step followed by a homogenization and/or sonication step) to obtain the desired mean particle size. The required sonication conditions will vary depending on liquid volume, type of sonication equipment, position of the probe and temperature of the solution, etc.

These nanoparticulate IC31® compositions according to the present invention are also sufficiently stable to allow industrial production of pharmaceutical compositions which fulfil GMP standards. For example, the compositions do not become too turbid (e.g. $OD_{550}$<0.2) and/or would have a particle size too large for sterile filtration after storage at 2° C. to 8° C., preferably at 4° C., or most preferably at room temperature for at least 24 h, e.g. after storage of at least 2 days, more preferably at least 3 days, at least 5 days, at least 10 days, at least 21 days, at least 50 days, at least 57 days, more preferably at least 200 days, most preferably for at least one year.

The mean particle size of the stable nanoparticulate IC31® compositions according to the present invention may slightly increase over storage time, depending e.g. on the storage term, storage conditions, and/or composition components. However, the mean particle size can be decreased again by applying an energy input as described above, e.g. by another heating and/or homogenization and/or sonication step.

With the present invention, it is therefore made possible to provide a stable nanoparticulate IC31® composition which allows novel and simplified production processes for sterile pharmaceutical compositions, especially vaccines containing IC31®.

According to the present invention, the KLK peptide and ODN1a are prepared in aqueous solutions, mixed at a molar ratio as further described below, the appropriate buffer components (e.g., Tris, Histidine, ammonium bicarbonate, etc.) are added, an energy input is provided, and, preferably, sterile-filtered to produce IC31® compositions. The compositions according to the present invention are provided as an aqueous mixture that is a nanosuspension, meaning a suspension of nanoparticles as described above (due to reduction of particle size in the IC31® complexes formed), i.e. a nanoparticulate IC31® composition.

Preferably, the KLK peptide is present in the compositions according to the present invention in a concentration of at least 10 pmol/mL, preferably of at least 100 pmol/mL, especially of at least 500 pmol/mL. Preferred concentration ranges of KLK are therefore 10 pmol/mL to 1000 nmol/mL, preferably 100 pmol/mL to 50 nmol/mL, especially 500 pmol/mL to 10 nmol/mL. Another preferred concentration of KLK can be up to 3300 nmol/mL. Accordingly, the ODN1a is preferably present in a concentration of at least 0.5 pmol/mL, even more preferred at least 4 pmol/mL, especially at least 20 pmol/mL. Preferred concentration ranges of ODN1a are therefore 0.5 nmol/mL to 40 nmol/mL, preferably 4 pmol/mL to 2 nmol/mL, especially 20 nmol/mL to 500 nmol/mL. Another preferred concentration of ODN1a can be up to 132 nmol/mL.

Preferably, the KLK peptide and the ODN1a oligodeoxynucleotide are present in the compositions according to the present invention in a molar ratio of 10:1 to 100:1, preferably 20:1 to 50:1, most preferably 25:1.

The nanoparticulate IC31® compositions according to the present invention have a significantly reduced particle size (and turbidity) compared to the classical IC31® compositions.

The term 'classical IC31®' composition as used throughout the present specification shall mean the IC31® formulations known in the prior art, especially the known IC31® formulations containing KLK and ODN1a in a molar ratio of 25:1, preferably 1000 nmol/mL KLK and 40 nmol/mL ODN1a, formulated either in 10 mM Tris and 135 mM NaCl, or 5 mM phosphate buffer and 135 mM NaCl. The classical IC31® formulations contain a high salt/ion concentration and are prepared without any energy input step and thus, have a mean particle size of more than 1 μm, especially about 5 to 50 μm.

The turbidity can also be a measure of particle size of an IC31® composition and can be measured by determination of the $OD_{550}$ value on a UV-VIS spectrophotometer. Alternatively, turbidity can be determined by use of a nephelometer and comparing the sample to standard turbidity solutions. With regard to the method using a UV-VIS spectrophotometer, a composition with an $OD_{550}$ value equal to or less than 0.2 is filterable through a 0.2 μm filter, which is the industry standard for sterility. The compositions according to the present invention are readily adjustable to such turbidity ($OD_{550}<0.2$) with the methods disclosed herein. The composition according to the present invention, therefore, preferably has an $OD_{550}$ value of equal to or less than 0.2, preferably of equal to or less than 0.1, especially of less than 0.05.

However, the above description about turbidity only applies to instances in which turbidity can be reasonably considered as a correlate to the particle size in a suspension, which is not necessarily the case. If, for example, the particles in a suspension are very large and immediately precipitate, sedimenting at the bottom of the container, the 'supernatant', i.e. the remaining composition, would appear as a clear liquid. In this case, determination of turbidity of the supernatant would not be a measure for particle size of the suspension.

For sterile filtration, appropriate viscosity of the mixture to be filtered is also critical. Viscosity can be measured e.g. on a Brookfield DV-E rotation viscometer at 20° C. using an LV61 spindle and can be reported as centipoise (cP=milliPascal seconds). Preferred compositions have a viscosity of less than 15 cP. Even more preferred compositions have viscosities of less than 12 cP or even less than 10 cP.

With the methods according to the present invention, nanoparticulate IC31® compositions are enabled; i.e., compositions in which the mean particle size is preferably less than 0.2 μm. The mean particle size according to the present invention is preferably determined by dynamic light scattering (DLS), e.g. using a Malvern Zetasizer system or a Wyatt Dynapro system. Using this method, a particle size distribution is generated resulting in a mean particle size in the nm to μm range for the analyzed sample.

However, the quality of the mean particle size as determined e.g. by a Malvern Zetasizer system or a Wyatt Dynapro system is dependent on the particle size distribution, which is a list of values or a mathematical function that defines the relative amounts of particles present, sorted according to size. The more homogenous and narrow the particle size distribution is the more reliable is the determined mean particle size. Usually, the commercially available DLS systems, such as the Malvern Zetasizer system or a Wyatt Dynapro system, give a value for the quality of the determined mean particle size, e.g. a polydispersity index, or a sum of squares (SOS) error statistic value. The lower those error values, the more homogenous and narrow is the particle size distribution, thus, the more reliable is the given mean particle size. Polydispersity refers to the level of homogeneity of the sizes of the particles. When the level of homogeneity is high, the particles can be considered to be virtually identical in their size, or monodisperse. The level of homogeneity is considered high when the percent polydispersity is less than 15%. When the level of homogeneity is low (percent polydispersity greater than 30%), the particle population can be considered to contain significantly different sizes, and is referred to as polydisperse. The polydispersity index from the Cumulants algorithm is representative of the width of the hypothetical monomodal distribution. Accordingly, a large polydispersity index can indicate either a wide distribution or a multi-modal distribution. However, the optimal particle size distribution for determining a valid mean particle size would be a monomodal and narrow curve describing the particle size distribution, i.e. a single particle size with a Gaussian distribution.

According to a preferred embodiment of the present invention, the mean particle size of the nanoparticles in the composition of the present invention is less than 1 μm, preferably less than 0.8 μm, more preferably less than 0.7 μm, even more preferably less than 0.5 μm, still more preferably less than 0.2 μm, and most preferably less than 0.1 μm.

The compositions according to the present invention preferably contain a suitable buffer system, for example a Tris, a Histidine, a carbonate, a bicarbonate, a 2-(N-morpholino) ethanesulfonic acid (MES) or a 3-(N-morpholino)propanesulfonic acid (MOPS) buffer system, especially a Tris, an ammonium bicarbonate or a Histidine buffer system.

If the composition according to the present invention is provided with a Tris buffer, it preferably contains 1 to 50 mM Tris, more preferred 2 to 30 mM Tris, especially 5 to 20 mM Tris, even more preferably 5 to 10 mM Tris. If the composition according to the present invention is provided with a Histidine buffer, it preferably contains 1 to 50 mM Histidine, more preferred 2 to 30 mM Histidine, especially 3 to 20 mM Histidine.

With the present invention, a method for providing nanoparticulate IC31® compositions is provided which applies low salt and phosphate ion concentrations (as further defined below). High salt concentrations did not result in stable nanoparticle formation. Preferred ion concentrations provided in the compositions according to the present invention are therefore in the range of 1 to 80 mM, 1 to 50 mM, or especially of 5 to 30 mM. Preferred ions at these low concentrations are $Na^+$, $K^+$, $NH_4^+$, $Cl^-$, $CO_3^{2-}$, and $HCO_3^-$.

Since ions such as $Ca^{2+}$ ions, $Mg^{2+}$ ions, phosphate ions, acetate ions or citrate ions, when present at concentrations above about 1 mM do not allow stable nanoparticle formation, the compositions according to the present invention are preferably completely free of these ions; or contain $Ca^{2+}$ ions, phosphate ions, citrate ions or acetate ions at concentrations of less than 1 mM.

The nanoparticulate IC31® compositions according to the present invention are preferably sterile-filterable and, as such, are enabled for GMP sterile filtration. This sterile filtration can be performed, for example, with the aid of different membranes, e.g., PVDF (polyvinyldifluoride), nylon, cellulose acetate or PES (polyethersulfone). Examples of suitable sterile filters are the VWR sterile syringe filter, Millex GV filter unit, Pall Acrodisc® syringe filter and the Fluorodyne® II DFL. Preferably, the present composition is filterable through a 0.2 µm sterile filter. Preferred compositions according to the present invention are indeed provided in a sterile form due to sterile filtration techniques; i.e., they have actually passed through a sterile filter and preserve their sterility afterwards due to appropriate measures, such as appropriate sealing of the containers (e.g. glass vials or syringes) containing the compositions and/or aseptic techniques for subsequent formulation or use steps, to prevent contamination.

Another characteristic parameter which can be adjusted in the compositions according to the present invention is pH. According to a preferred embodiment, the pH of the compositions according to the present invention is 5.5 to 9.5, more preferred 6 to 9, especially 6 to 7. With the adjustment of pH, other parameters such as mean particle size and viscosity, can be fine-tuned to allow optimal processing of the compositions especially for sterile filtration.

The nanoparticulate IC31® compositions according to the present invention can contain IC31® as active ingredient only, e.g. without any antigen. Such pure adjuvant compositions can be administered separately from the actual vaccine containing one or more antigens. The two or more separate compositions can be administered at the same or different site and/or at the same or different time; e.g., subsequently in either order. Alternatively, the nanoparticulate IC31® compositions according to the present invention can be mixed with the antigen(s) or vaccine composition, either for storage or directly prior to administering the mixture to a subject (bed-side mixing).

The most preferred use of IC31®-containing compositions is in the field of immune stimulation for therapy or prevention, especially as an adjuvant, or an adjuvanted vaccine. Therefore, the compositions according to the present invention are preferably compositions for vaccination, especially for the vaccination of animal or human subjects. Accordingly, such preferred compositions contain, in addition to IC31®, at least one antigen, preferably a polypeptide antigen.

Since IC31® is known for its performance as an adjuvant for many kinds of antigens, the nature of the antigen is usually not critical. Therefore, in principle, all relevant antigens may be included in a vaccine according to the present invention. Since production of pharmaceuticals for the vaccination of human subjects and/or animals is a major field of application of the nanoparticle compositions according to the present invention, antigens of human or animal pathogens may be provided as antigens in the compositions, preferably a $CD8^+$ CTL peptide, a $CD4^+$Th peptide, a polypeptide (or a protein), a glycoprotein, a lipoprotein, a virus particle, a whole cell or a subunit thereof. The antigen may be derived from a pathogen such as a virus, a bacterium, a fungus or a parasite. Especially, the antigen is derived from Influenza virus, Hepatitis A, B or C virus (HAV, HBV, HCV), Human Papilloma virus (HPV), Human Immunodeficiency virus (HIV), Herpes Simplex virus (HSV), Parvovirus B19, Tick Borne Encephalitis virus (TBEV), Dengue virus (DENY), Japanese Encephalitis virus (JEV), West Nile virus (WNV), Yellow Fever virus (YFV), Cytomegalovirus (CMV), *Mycobacterium tuberculosis, Staphylococcus aureus, Staphylococcus epidermidis, Helicobacter pylori, Streptococcus pyogenes, Streptococcus agalactiae, Chlamydia pneumoniae, Chlamydia trachomatis, Streptococcus pneumoniae, Klebsiella pneumoniae, Neisseria meningitidis, Borrelia burgdorferi, Borrelia afzelii, Borrelia garinii, Haemophilus influenzae, Moraxella catarrhalis, Enterococcus faecalis, Enterococcus faecium, Escherichia coli, Clostridium difficile, Shigella flexneri, Campylobacter jejuni, Plasmodium falciparum, Plasmodium vivax, Aspergillus* spp. or *Candida albicans*.

In addition, antigens derived from human or animal cancers may be provided as antigens in the compositions of the current invention; for example, a $CD8^+$CTL peptide, a $CD4^+$ Th peptide, a polypeptide, a protein, a glycoprotein, a lipoprotein, a whole cell or a subunit thereof. Examples of such cancers include carcinoma, lymphoma, blastoma, sarcoma, and leukemia or lymphoid malignancies. More particular examples of such cancers include, but are not limited to, squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, head and neck cancer, brain cancer, gastric or stomach cancer including gastrointestinal cancer and gastrointestinal stromal cancer, pancreatic cancer, glioblastoma, neuroblastoma, cervical cancer, ovarian cancer, liver cancer, bladder cancer, cancer of the urinary tract, hepatocellular carcinoma, soft-tissue sarcoma, Kaposi's sarcoma, breast cancer, colon cancer, rectal cancer, colorectal carcinoma (CRC), endometrial or uterine carcinoma, salivary gland carcinoma, kidney or renal cancer, prostate cancer, vulval cancer, thyroid cancer, carcinoid carcinoma, anal carcinoma, penile carcinoma, melanoma, superficial spreading melanoma, lentigo maligna melanoma, acral lentiginous melanoma, nodular melanoma, multiple myeloma and B-cell lymphoma; including, but not limited to, low grade/follicular non-Hodgkin's lymphoma (NHL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, mantle cell lymphoma, AIDS-related lymphoma, Waldenstrom's macroglobulinemia, chronic lymphocytic leukemia (CLL), acute lymphoblastic leukemia (ALL), hairy cell leukemia and chronic myelogenous leukemia.

It is of course possible to adapt known vaccine formats (among many others, e.g. WO 97/019169 A, WO 97/030721A, WO 99/020301 A, WO 99/038528 A, WO 02/066621 A, WO 02/059148, WO 2004/024182 A, WO 2005/004910 A, WO 2006/045677 A, WO 2007/121491 A or PCT/EP2009/060271) to the vaccine compositions according to the present invention by using nanoparticulate IC31® as an adjuvant. Accordingly, a known vaccine may comprise other adjuvants, such as, e.g. alum, AS03, AS04, MF59, and could be combined with the nanoparticulate IC31® compositions according to the present invention.

Preferably, the composition according to the present invention contains a buffer solution, preferably Tris, or most preferably Histidine, along with carbohydrates, preferably sucrose. Sucrose is a non-reducing disaccharide and has been shown to impart storage stability to nanoparticulate IC31® solutions and to improve filterability of nanoparticulate IC31® solutions by minimizing the loss of IC31® materials on filtration membranes. Moreover, carbohydrate excipients such as e.g. sucrose and/or sorbitol can be used (instead of salt ions) to make the final compositions isotonic, which would be advantageous especially for administration to subjects.

Another suitable buffer component is ammonium bicarbonate; however, due to the potential release of ammonia and carbon dioxide gases over time, such compositions might be less stable.

The Histidine buffered compositions result in the smallest particle sizes (as small as 50 nm to 100 nm); whereas other buffer systems such as e.g. Tris result in a mean particle size of about 100 nm or more. The buffer component(s) can be selected based on the desired pH range of the final composition, e.g. if the final composition contains one or more antigens, the buffer system(s) can be selected based on the pH requirements for the antigen(s). Thus, the invention provides for an IC31® nanoparticulate composition in that the mean particle size of the complexes comprising the peptide and the oligodeoxynucleotide is less than 1 µm, preferably less than 0.8 µm, more preferably less than 0.7 µm, even more preferably less than 0.5 µm, still more preferably less than 0.2 µm, and most preferably less than 0.1 µm.

WFI is also suitable for the IC31® nanoparticulate compositions according to the present invention. However, since WFI does not comprise any buffering agents, there could be variations in particle size, pH and stability, thus affecting filterability and reproducibility of the compositions.

Furthermore, WFI-based IC31® compositions may require more energy input to result in the desired nanoparticles compared to compositions with low ionic strength. Thus, e.g. the time or temperature of the heating step could be increased accordingly, and/or a more intense homogenization or sonication step could be applied, or multiple initial energy input steps could be used to result in the desired particle size, e.g. a heating step followed by a homogenization step and/or a sonication step.

Preferably, the composition according to the present invention may further comprise a surfactant, such as e.g. Tween 20 or Tween 80, which reduces the potential loss of IC31® components onto e.g. the walls of containers or on filtration membranes.

Although the parameters of the compositions disclosed herein may be combined to encompass all possible permutations of features disclosed herein, the following compositions are specifically preferred due to their performance and handling in the production process.

A preferred pharmaceutical composition in liquid form comprising a peptide with the amino acid sequence $KLKL_5KLK$ and an oligodeoxynucleotide with the nucleic acid sequence $(dIdC)_{13}$ is characterized in that
  the peptide is present in a concentration of at least 100 nmol/mL and the oligodeoxynucleotide is present in a concentration of at least 4 nmol/mL,
  the mean particle size of the IC31® complexes comprising the peptide and the oligodeoxynucleotide is less than 1 µm,
  the sodium ion concentration is from 1 to 25 mM,
  it may contain $Ca^{2+}$ ions, phosphate ions, citrate ions or acetate ions at concentrations of less than 1 mM,
  it contains 1 to 50 mM of Tris buffer with a pH of 6 to 9, or 1 to 50 mM of Histidine buffer with a pH of 5 to 8,
  optionally, it has a viscosity of less than 15 cP, and
  optionally, it is sterile, preferably by sterile filtration.

Preferably, the peptide and the oligodeoxynucleotide are present in the compositions according to the present invention in a molar ratio of 10:1 to 100:1, preferably 20:1 to 50:1, most preferably 25:1. A preferred pH range for the Tris buffer is 6 to 8, most preferred 7.0 to 7.5. Optionally, the composition has an $OD_{550}$ value of equal to or less than 0.2.

According to another aspect, the present invention also relates to a method for producing a composition comprising in liquid form a peptide with the amino acid sequence $KLKL_5KLK$ and an oligodeoxynucleotide with the nucleic acid sequence $(dIdC)_{13}$, comprising the following steps:
  providing an aqueous mixture of the peptide and the oligodeoxynucleotide, wherein the aqueous mixture has an ion concentration of 1 to 80 mM and may contain $Ca^{2+}$ ions, phosphate ions, citrate ions or acetate ions at concentrations of less than 1 mM,
  providing an energy input to the aqueous mixture, preferably by a heating step to 40° C. to 60° C. or a homogenization step or a sonication step, and
  optionally, filtering the aqueous mixture through a sterile filter.

Preferably, the aqueous mixture is free of $Ca^{2+}$ ions, phosphate ions, citrate ions or acetate ions.

The present invention further comprises a method for producing a composition according to the present invention that comprises the following steps:
  providing an aqueous mixture of the peptide and the oligodeoxynucleotide, wherein the aqueous mixture has an ion concentration of 1 to 80 mM and may contain $Ca^{2+}$ ions, phosphate ions, citrate ions or acetate ions at concentrations of less than 1 mM,
  providing an energy input to the aqueous mixture, preferably by a heating step to 40° C. to 60° C. or a homogenization step or a sonication step,
  optionally, filtering the aqueous mixture, preferably through a sterile filter to obtain a sterile composition, and
  finishing the filtered composition to a pharmaceutical composition.

Preferably, the aqueous mixture is free of $Ca^{2+}$ ions, phosphate ions, citrate ions or acetate ions.

Preferably, the aqueous mixture contains a buffer system, especially a Tris, a Histidine, a 2-(N-morpholino) ethanesulfonic acid (MES) or a 3-(N-morpholino) propanesulfonic acid (MOPS) buffer system, more preferred a Tris, or a Histidine buffer system; or a combination of any such buffer systems, especially a combination of Tris and Histidine buffer systems. Such combination of two or more buffer systems would be suitable, for example, when an antigen formulation buffered in one system is combined with nanoparticulate IC31® buffered in another system.

The filtered or finalized composition can be stored at 2° C. to 8° C., most preferably at room temperature, and stays stable, especially with respect to the particle sizes. The finalized composition could be checked regularly for possible increases in mean particle size especially after longer storage periods using a standardized light scattering method.

The methods according to the present invention are specifically suitable for producing adjuvant and/or vaccine compositions. Accordingly, it is preferred to provide at least one antigen in the aqueous mixture when producing a vaccine. A bed-side mixing approach as described above is also suitable.

At the end of the production process according to the present invention, the compositions are filled or packed into suitable containers for end use, preferably finalized in syringes (e.g., ready to use syringes) or glass vials which are suitable for allowing filling of syringes for use (e.g., through rubber seals).

The energy input provided in the present method should be appropriate for the reduction of particle size to be achieved for the final product or at least for the sterile filtration step. Of course, care must be taken that the other ingredients (e.g., an antigen) are not harmed by this energy input (i.e., that the antigen is not denatured by application of a too high temperature). This can be readily adjusted by the person skilled in the art in view of the nature of the ingredients of the composition to be produced.

Preferred techniques for providing the energy input in the method according to the present invention are infrared irradiation, sonication, induction heating, thermal heating, especially by means of a water bath, vortexing, applying shear forces, especially by means of high speed or high pressure homogenization devices, or combinations of these methods. Preferably, the energy input is provided by heating to 40° C. to 60° C., and/or homogenization, and/or sonication, or combinations thereof. High speed homogenization of a liquid can be provided by the use of a device such as the Ultra-Turrax, which is capable of ultra-high speed stirring. High-pressure homogenization is defined by the pressure applied and the number of cycles, i.e., how many times the solution is pumped through the homogenizer. The amount of energy input also depends e.g. on the composition and on the containers (shape, size, material, etc.) and thus, it cannot be exactly pre-determined by pure calculation but must be actually measured. For example, the energy required for heating one milliliter of water from 22° C. to 40° C. would be 75.24 J; consequently, to heat one liter of water, 75240 J would be required. As a rule of thumb for using a homogenizer to provide energy input, the temperature increase is 2° C. to 3° C. per 100 bar and per cycle for aqueous solutions like IC31® nanoparticles, but of course it depends on the exact geometry of the valves in the system and must be individually evaluated for each homogenizer.

If the energy input step is provided by sonication, typical sonication conditions for a one mL IC31® composition would be, e.g. a one second pulse with a Virtis 100 sonicator and VirSonic 100 (3 mm) probe followed by 5 seconds of gentle mixing in an ice bath, repeated 4 times. Sonication conditions for a larger volume of IC31 would vary considerably e.g., in the probe size used and in the duration and number of pulses delivered. Furthermore, sonication conditions may vary with liquid volume, type of sonication equipment, position of the probe and temperature of the solution, etc.

The energy input can be applied depending on the particle size desired. This energy input is therefore preferably provided for a suitable time period to reduce the particle size to a mean particle size of less than 1 µm, preferably less than 0.8 µm, more preferably less than 0.7 µm, even more preferably less than 0.5 µm, still more preferably less than 0.2 µm, and most preferably less than 0.1 µm.

If the energy input step is performed as a heating step, a moderate heating (e.g. to 40° C., 42° C., 45° C., 50° C., 55° C. or 60° C.) may be performed for 2 min to 60 min, preferably for 5 min to 30 min, especially for 10 min to 20 min.

If a Tris buffer is used during the methods according to the present invention, the aqueous mixture preferably contains 1 to 50 mM Tris, preferably 2 to 30 mM Tris, especially 5 to 20 mM Tris, even more preferably 5 to 10 mM Tris.

If a Histidine buffer is used during the methods according to the present invention, the aqueous mixture preferably contains 1 to 50 mM Histidine, more preferred 2 to 30 mM Histidine, especially 3 to 20 mM Histidine.

When performing the methods according to the present invention, the aqueous mixture can e.g. contain ions in a concentration of 1 to 50 mM, especially of 5 to 30 mM.

The sterile filtration step according to the present invention can be performed with any suitable sterile filter; however, for production processes for pharmaceutical compositions, the sterile filter must be suitable for GMP or GMP approved. Preferably, the sterile filter has a cut-off value of 0.2 µm.

Preferably, the filtration step according to the present invention is performed directly after applying the composition onto the filter in order to avoid or minimize adsorption of the composition to the filter and subsequent reduction in recovery, i.e. the time between applying the composition onto the filter and the filtering should be as short as possible to optimize recovery after filtration.

The aqueous mixture is preferably made of water of high purity, at least "Purified Water" or "Water for Injection" (according to EMEA Guidance EMEA/CVMP/115/01). According to a preferred embodiment of the present methods or compositions, Water for Injection grade (WFI grade) water is used for providing the aqueous mixture.

The present invention also provides a method for producing a composition comprising in liquid form a peptide with the amino acid sequence KLKL$_5$KLK and an oligodeoxynucleotide with the nucleic acid sequence (dIdC)$_{13}$ and wherein the peptide and the oligodeoxynucleotide are present as nanoparticles, which comprises the following steps providing an aqueous mixture of the peptide and the oligodeoxynucleotide, wherein the aqueous mixture has an ion concentration of 1 to 80 mM and it may contain Ca$^{2+}$ ions, phosphate ions, citrate ions or acetate ions at concentrations of less than 1 mM, providing an energy input to the aqueous mixture, preferably by a heating step to 40° C. to 60° C., and filtering the aqueous mixture through a sterile filter, and increasing the particle size, and optionally finishing the obtained mixture into a pharmaceutical preparation.

Preferably, the aqueous mixture is free of Ca$^{2+}$ ions, phosphate ions, citrate ions or acetate ions.

This alternative method allows a final increase of the particle size, a reconstitution of mean particle size if this is needed for the end product (e.g. for reasons of depot performance, adjuvant capacity, etc.). Such a reconstitution can e.g. be done by addition of phosphate ions (or Ca$^{2+}$, citrate, etc. ions), by addition of NaCl, and/or by pH change (e.g. increase of pH).

Of course, also in this method, in which larger particle sizes are reconstituted after sterile filtration, all the preferred embodiments as described above may be applied as well, in all reasonable combinations.

Preferred Aspects:

1. Pharmaceutical composition in liquid form comprising a peptide with the amino acid sequence $KLKL_5KLK$ and an oligodeoxynucleotide with the nucleic acid sequence $(dIdC)_{13}$, characterized in that the mean particle size of the complexes comprising the peptide and the oligodeoxynucleotide is less than 1 μm.

2. Composition according to preferred aspect 1, characterized in that the KLK peptide is present at a concentration of at least 10 nmol/mL, preferably of at least 100 nmol/mL, especially of at least 500 nmol/mL, most especially of at least 1000 nmol/mL.

3. Composition according to preferred aspects 1 or 2, characterized in that the oligodeoxynucleotide ODN1a is present in a concentration of at least 0.5 nmol/mL, preferably at least 5 nmol/mL, especially at least 10 nmol/mL, most especially of at least 40 nmol/mL.

4. Composition according to any one of preferred aspects 1 to 3, characterized in that it has an $OD_{550}$ value of equal or lower than 0.2, preferably of equal or lower than 0.1, especially of lower than 0.05.

5. Composition according to any one of preferred aspects 1 to 4, characterized in that it has a viscosity less than 15 cP, preferably less than 12 cP, especially less than 10 cP.

6. Composition according to any one of preferred aspects 1 to 5, characterized in that the mean particle size of the complexes comprising the peptide KLK and the oligodeoxynucleotide ODN1a is less than 1 μm, preferably less than 0.8 μm, more preferably less than 0.7 μm, even more preferably less than 0.5 μm, still more preferably less than 0.2 μm, and most preferably less than 0.1 μm.

7. Composition according to any one of preferred aspects 1 to 6, characterized in that it contains a buffer system, preferably a Tris, a Histidine, a carbonate, a bicarbonate, a 2-(N-morpholino) ethanesulfonic acid (MES) or a 3-(N-morpholino) propanesulfonic acid (MOPS) buffer system, especially a Tris, and/or a Histidine buffer system.

8. Composition according to any one of preferred aspects 1 to 7, characterized in that is filterable through a 0.2 μm sterile filter.

9. Composition according to any one of preferred aspects 1 to 8, characterized in that it contains 1 to 50 mM Tris, preferably 2 to 30 mM Tris, especially 5 to 20 mM Tris, even more preferably 5 to 10 mM Tris.

10. Composition according to any one of preferred aspects 1 to 9, characterized in that it contains ions in a concentration of 1 to 80 mM, preferably of 1 to 50 mM, especially of 5 to 30 mM.

11. Composition according to any one of preferred aspects 1 to 10, characterized in that it is free of $Ca^{2+}$ ions, phosphate ions, citrate ions or acetate ions, or contains $Ca^{2+}$ ions, phosphate ions, citrate ions or acetate ions in an amount less than 1 mM.

12. Composition according to any one of preferred aspects 1 to 11, characterized in that it has a pH of 5.5 to 9.5, preferably of 7 to 9, more preferred of 7.2 to 9.0, especially of 7.5 to 8.5.

13. Composition according to any one of preferred aspects 1 to 12, characterized in that it is a vaccine and contains an antigen, preferably a peptide or polypeptide antigen.

14. Composition according to any one of preferred aspects 1 to 13, characterized in that it contains an antigen of a human pathogen, preferably a $CD8^+CTL$ peptide, a $CD4^+Th$ peptide, a polypeptide, a protein, a glycoprotein, a lipoprotein, a virus particle, a whole cell or a subunit thereof. The antigen may be derived from a pathogen such as a virus, a bacterium, a fungus or a parasite. Especially, the antigen is derived from Influenza virus, Hepatitis A, B or C virus (HAV, HBV, HCV), Human Papilloma virus (HPV), Human Immunodeficiency virus (HIV), Herpes Simplex virus (HSV), Parvovirus B19, Tick Borne Encephalitis virus (TBEV), Dengue virus (DENY), Japanese Encephalitis virus (JEV), West Nile virus (WNV), Yellow Fever virus (YFV), Cytomegalovirus (CMV), *Mycobacterium tuberculosis, Staphylococcus aureus, Staphylococcus epidermidis, Helicobacter pylori, Streptococcus pyogenes, Streptococcus agalactiae, Chlamydia pneumoniae, Chlamydia trachomatis, Streptococcus pneumoniae, Klebsiella pneumoniae, Neisseria meningitidis, Borrelia burgdorferi, Borrelia afzelii, Borrelia garinii, Haemophilus influenzae, Moraxella catarrhalis, Enterococcus faecalis, Enterococcus faecium, Escherichia coli, Clostridium difficile, Shigella flexneri, Campylobacter jejuni, Plasmodium falciparum, Plasmodium vivax, Aspergillus* spp. or *Candida albicans*.

15. Composition according to any one of preferred aspects 1 to 13, characterized in that it contains an antigen derived from a cancer, preferably derived from a human cancer, preferably a $CD8^+CTL$ peptide, a $CD4^+Th$ peptide, a polypeptide, a protein, a glycoprotein, a lipoprotein, a whole cell or a subunit thereof. Examples of such cancers include carcinoma, lymphoma, blastoma, sarcoma, and leukemia or lymphoid malignancies. More particular examples of such cancers include, but are not limited to, squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, head and neck cancer, brain cancer, gastric or stomach cancer including gastrointestinal cancer and gastrointestinal stromal cancer, pancreatic cancer, glioblastoma, neuroblastoma, cervical cancer, ovarian cancer, liver cancer, bladder cancer, cancer of the urinary tract, hepatocellular carcinoma, soft-tissue sarcoma, Kaposi's sarcoma, breast cancer, colon cancer, rectal cancer, colorectal carcinoma (CRC), endometrial or uterine carcinoma, salivary gland carcinoma, kidney or renal cancer, prostate cancer, vulval cancer, thyroid cancer, carcinoid carcinoma, anal carcinoma, penile carcinoma, melanoma, superficial spreading melanoma, lentigo maligna melanoma, acral lentiginous melanoma, nodular melanoma, multiple myeloma and B-cell lymphoma; including, but not limited to, low grade/follicular non-Hodgkin's lymphoma (NHL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, mantle cell lymphoma, AIDS-related lymphoma, Waldenstrom's macroglobulinemia, chronic lymphocytic leukemia (CLL), acute lymphoblastic leukemia (ALL), hairy cell leukemia and chronic myelogenous leukemia.

16. Composition according to any one of preferred aspects 1 to 15, characterized in that it contains one or more carbohydrates, preferably sucrose and/or sorbitol.

17. Pharmaceutical composition in liquid form comprising a peptide with the amino acid sequence $KLKL_5KLK$ and an oligodeoxynucleotide with the nucleic acid sequence $(dIdC)_{13}$, characterized in that
    the peptide is present at a concentration of at least 100 nmol/mL and the oligodeoxynucleotide is present at a concentration of at least 4 nmol/mL,
    the mean particle size of the complexes comprising the peptide and the oligodeoxynucleotide is less than 1 μm,
    the sodium ion concentration is from 1 to 25 mM,
    it may contain $Ca^{2+}$ ions, phosphate ions, citrate ions or acetate ions at a concentration of less than 1 mM, it contains 1 to 50 mM of Tris buffer with a pH of 7 to 9 or 1 to 50 mM of Histidine buffer with a pH of 5 to 8, optionally, it has a viscosity less than 15 cP, and optionally, it is sterile, preferably by sterile filtration.

18. Composition according to any one of preferred aspects 1 to 17, characterized in that the peptide and the oligodeoxynucleotide are present in a molar ratio of 10:1 to 100:1, preferably 20:1 to 50:1, most preferably 25:1.

19. Method for producing a composition according to any one of preferred aspects 1 to 18, characterized by the following steps:
provides an aqueous mixture of the peptide and the oligodeoxynucleotide, wherein the aqueous mixture has an ion concentration of 1 to 80 mM and may contain $Ca^{2+}$ ions, phosphate ions, citrate ions or acetate ions at concentrations of less than 1 mM,
providing an energy input to the aqueous mixture, preferably by a heating step to 40° C. to 60° C. or homogenization or sonication,
optionally, filtering the aqueous mixture, preferably through a sterile filter, and
optionally, finishing the filtered composition to a pharmaceutical composition.

20. Method according to preferred aspect 19, characterized in that the aqueous mixture contains a buffer system, preferably a Tris, a Histidine, a carbonate, a bicarbonate, a 2-(N-morpholino) ethanesulfonic acid (MES) or a 3-(N-morpholino) propanesulfonic acid (MOPS) buffer system, more preferred a Tris or a Histidine buffer system or a combination of Tris and Histidine buffer systems.

21. Method according to preferred aspects 19 or 20, characterized in that the composition is stored at 2° C. to 8° C.

22. Method according to any one of preferred aspects 19 to 21, characterized in that the aqueous mixture further contains an antigen.

23. Method according to any one of preferred aspects 19 to 22, characterized in that the energy input is provided for a suitable time period to reduce the particle size to a mean particle size of less than 1 μm, preferably less than 0.8 μm, more preferably less than 0.7 μm, even more preferably less than 0.5 μm, still more preferably less than 0.2 μm, and most preferably less than 0.1 μm.

24. Method according to any one of preferred aspects 19 to 23, characterized in that the aqueous mixture contains ions in a concentration of 1 to 50 mM, especially of 5 to 30 mM.

25. Method for producing a composition comprising in liquid form a peptide with the amino acid sequence $KLKL_5KLK$ and an oligodeoxynucleotide with the nucleic acid sequence $(dIdC)_{13}$, comprising the following steps:
providing an aqueous mixture of the peptide and the oligodeoxynucleotide, wherein the aqueous mixture has an ion concentration of 1 to 80 mM and may contain $Ca^{2+}$ ions, phosphate ions, citrate ions or acetate ions at concentrations of less than 1 mM,
providing an energy input to the aqueous mixture, preferably by a heating step to 40° C. to 60° C. or homogenization or sonication, and
filtering the aqueous mixture through a sterile filter, and increasing the particle size, and
optionally finishing the obtained mixture into a pharmaceutical preparation.

26. Method according to preferred aspect 25, characterized in that one or more of the steps disclosed in any one of the preferred aspects 19 to 24 are performed.

The invention is further described in the examples and the figures, yet without being restricted thereto.

Figure 5:
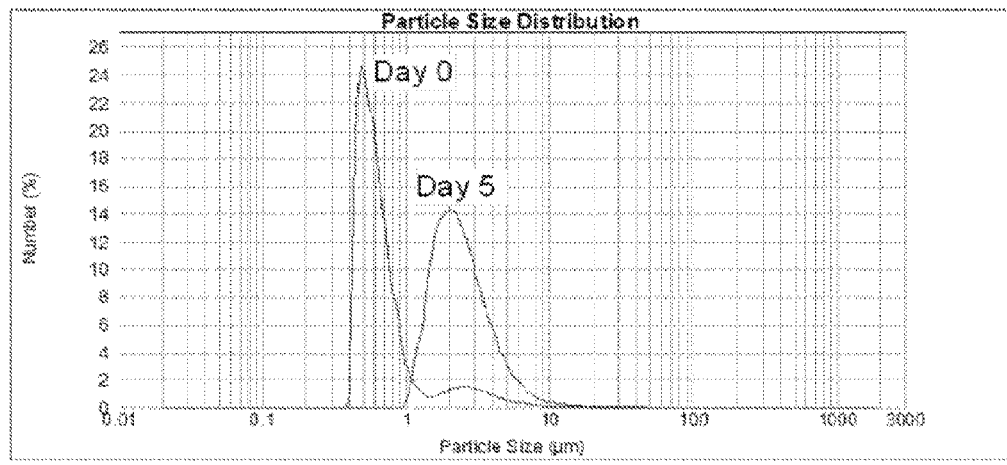
FIG. 5 shows a particle size analysis of classical IC31® (350 nmol/mL KLK/14 nmol/mL ODN1a) formulated in 5 mM phosphate/135 mM NaCl, pH 7.5, after 5 min stirring at 25,000 rpm using an Ultra-Turrax. Red line, PSD directly after stirring; green line, PSD of same sample after 5 days storage at 2-8° C.
Figure 6:
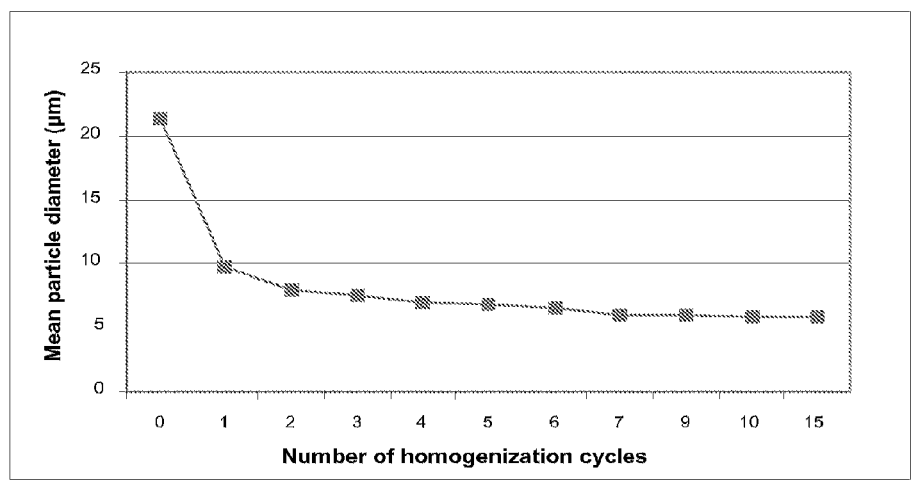
Figure 7:
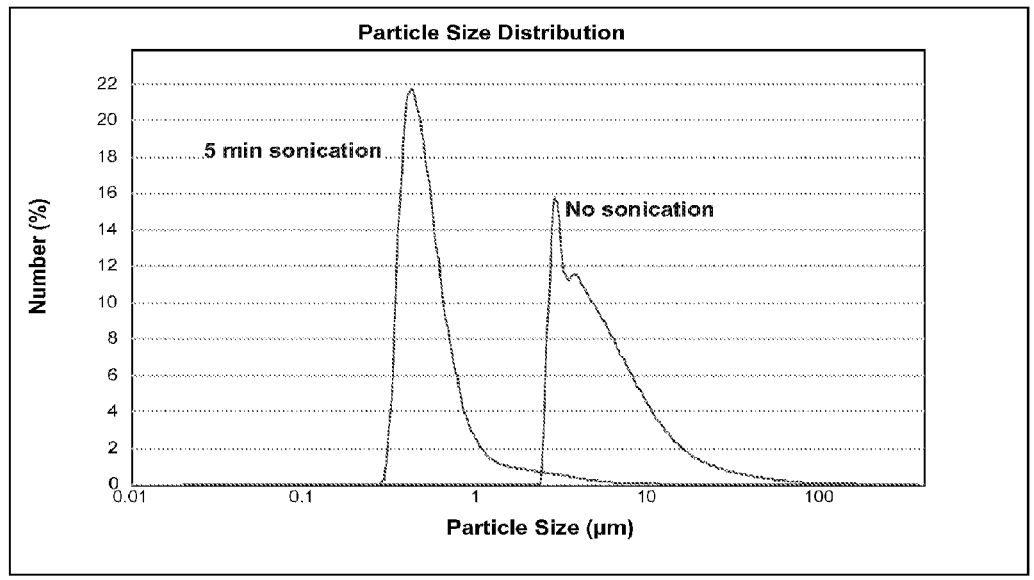
Figure 8:
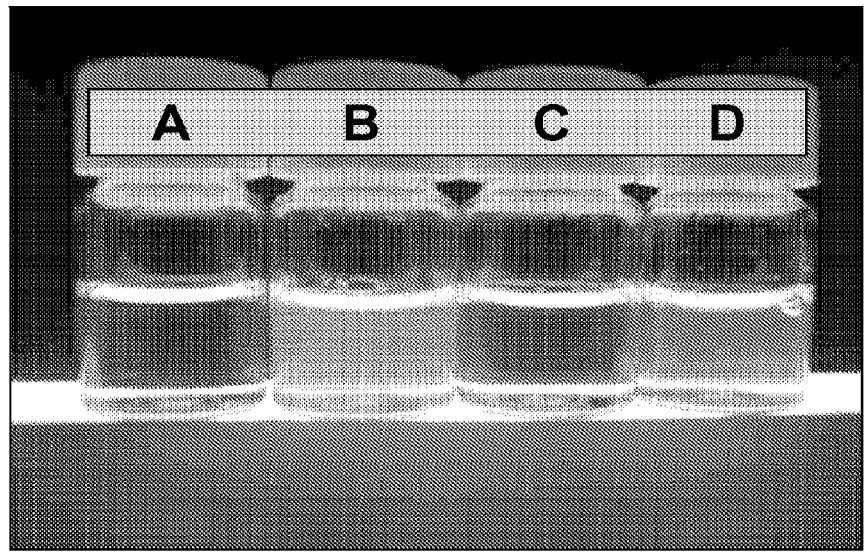
Figure 9:
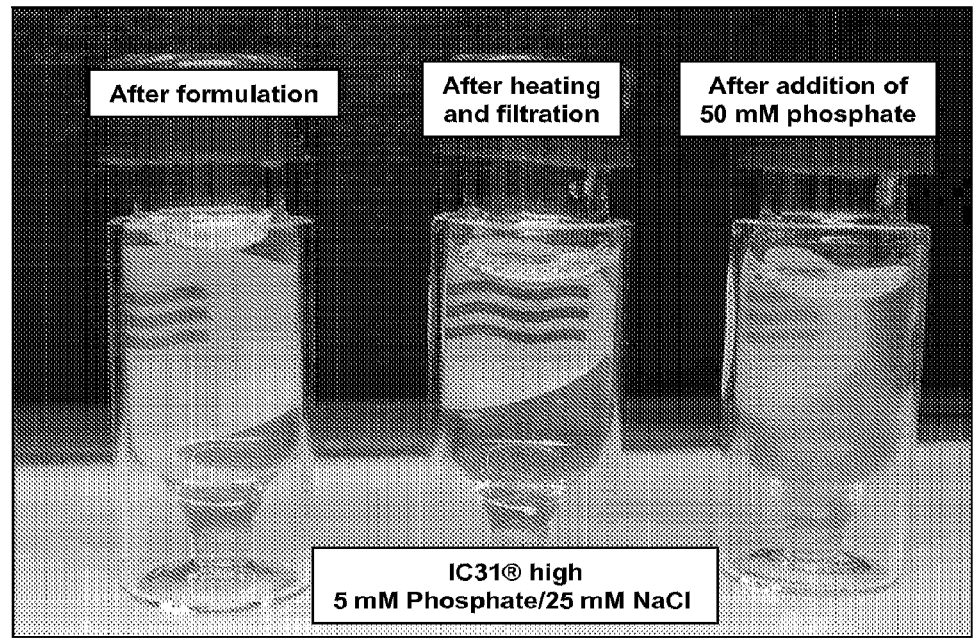
Figure 10:
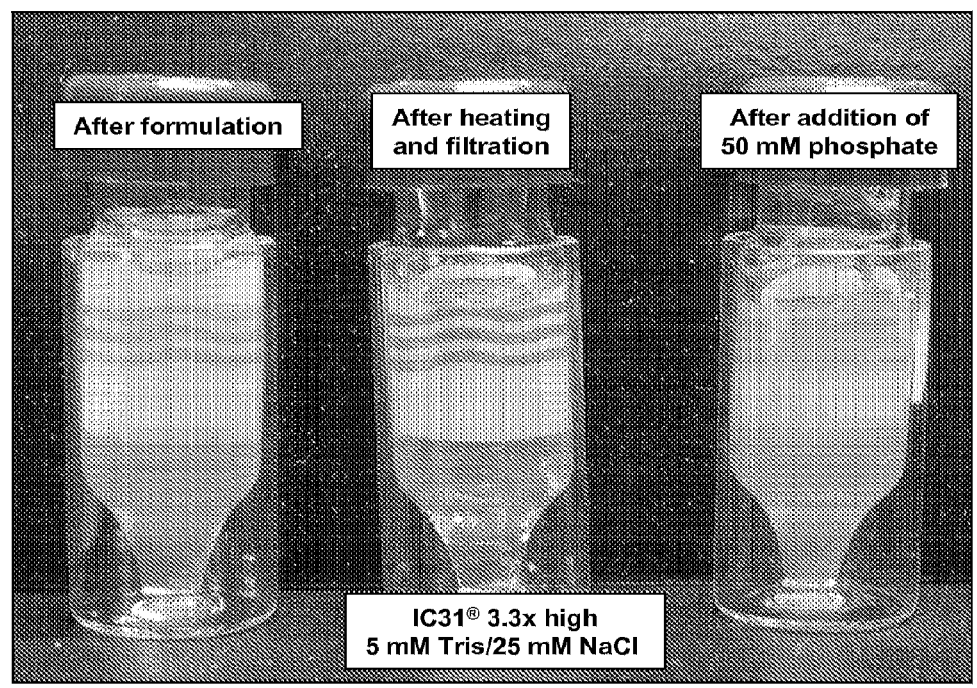
Figure 11A:
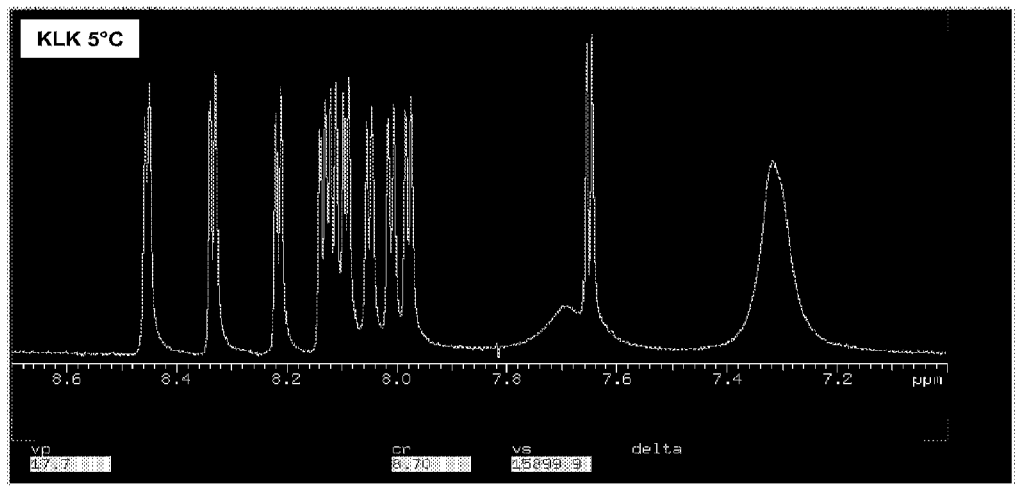
Figure 11B:
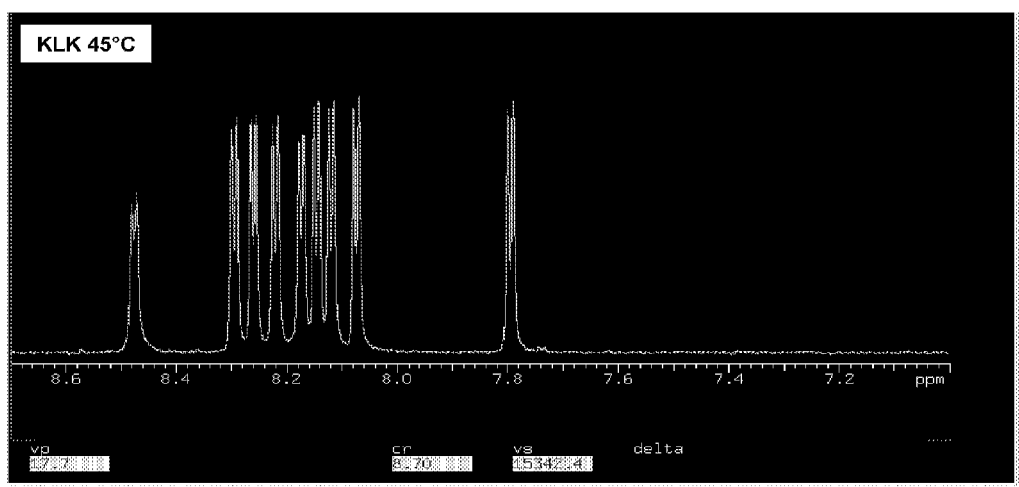
Figure 12:
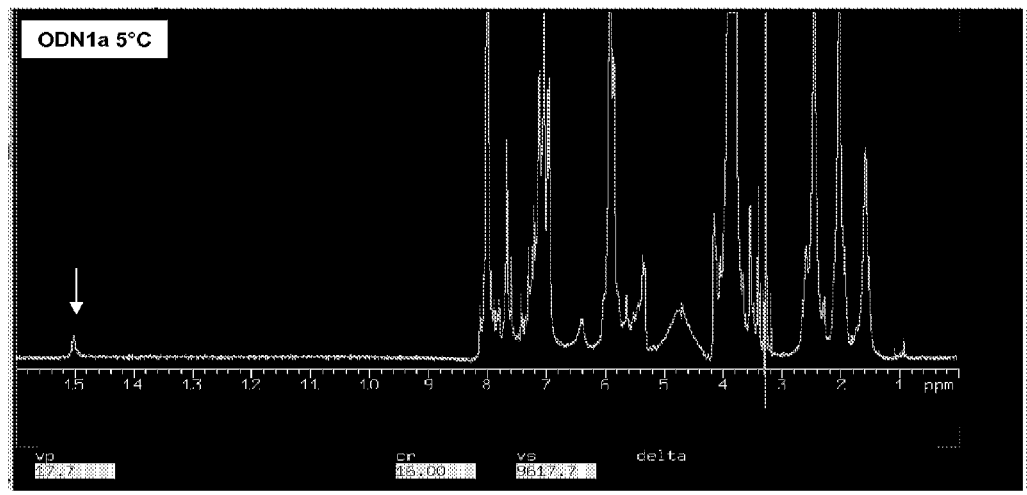
Figure 13:
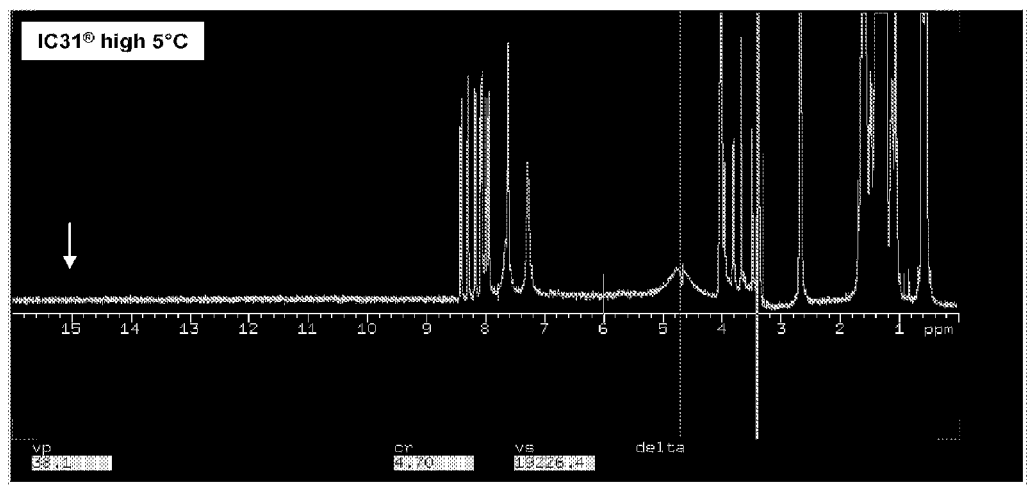
Figure 14:
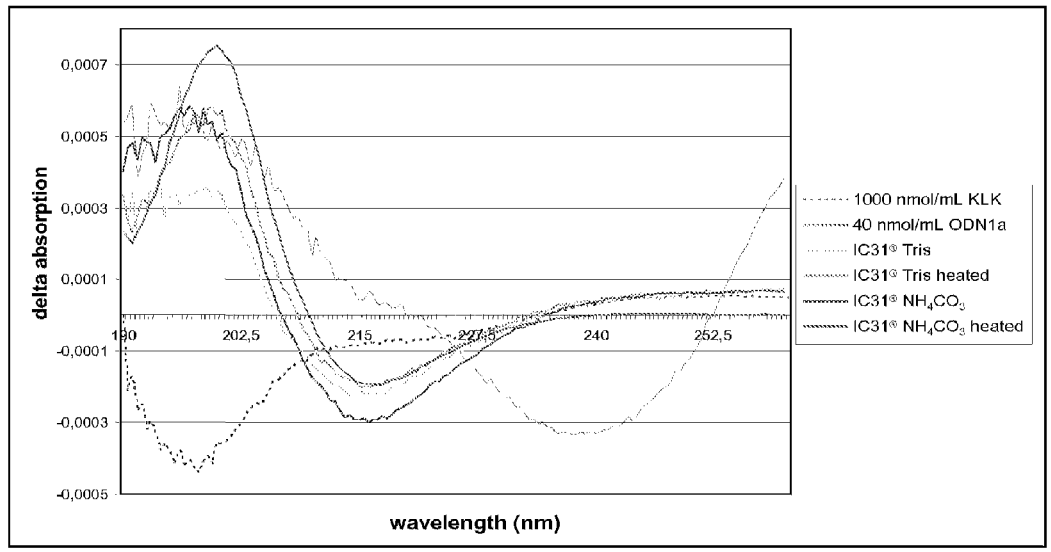
Figure 15:
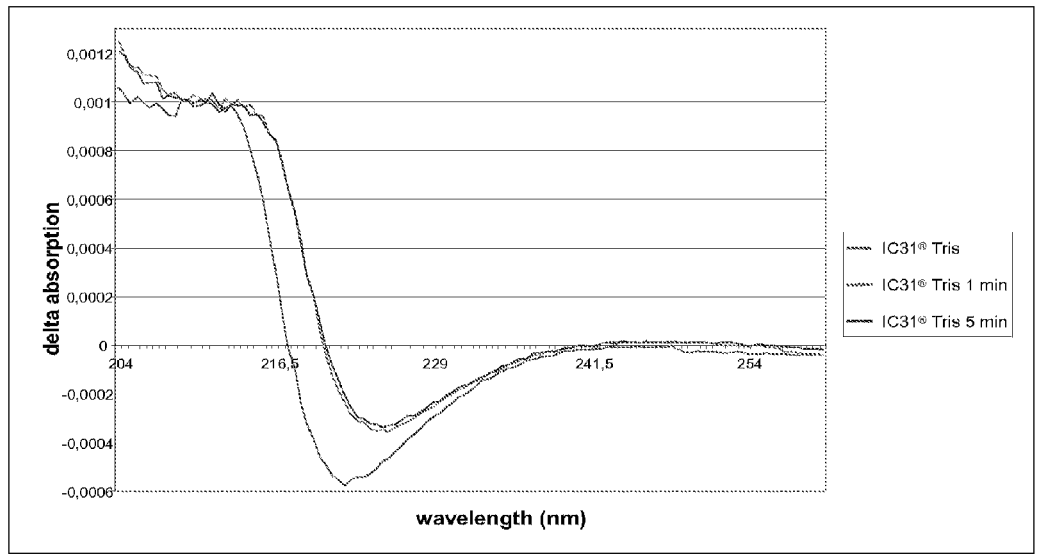

FIG. 6 shows the decrease in mean particle size per cycle number when using a Panda 2K Niro Soavi high pressure homogenizer. This was tested using classical IC31® formulation (350 nmol/mL KLK/14 nmol/mL ODN1a in 5 mM phosphate/135 mM NaCl, pH 7.5). After the first 1-2 cycles, the mean particle diameter remained constant at about 1-10 μm; no submicron particles were generated;

FIG. 7 shows a particle size analysis of a classical IC31® high (1000 nmol/mL KLK/40 nmol/mL ODN1a) formulated in 10 mM Tris/135 mM NaCl, pH 7.5 before and after a 5 min sonication treatment. Although the mean particle size is decreased to 0.2-0.4 μm by sonication, 90% of the total mass of KLK/ODN1a remains bound in particles larger than 1 μm;

FIG. 8 shows the effect of lowering the ionic strength of IC31® compositions on the resulting mean particle size. Tris buffer compositions with lowered ionic strength (vials A and C) showed no visible precipitation of KLK; concentrations were 800 nmol/mL KLK/10 nmol/mL ODN1a formulated in 10 mM Tris/25 mM NaCl, pH 6 (A), 10 mM Tris/250 mM NaCl/0.4% Tween 20, pH 8 (B) and 10 mM Tris/25 mM NaCl/0.4% Tween 20, pH 6 (C); classical IC31® high (1000 nmol/mL KLK/40 nmol/mL ODN1a) was formulated in 5 mM Tris/135 mM NaCl, pH 7.6 (D);

FIG. 9 shows reconstitution of particulate IC31® following sterile filtration of a nanoparticulate IC31® composition. Nanoparticulate IC31® high (1000 nmol/mL KLK/40 nmol/mL ODN1a) was formulated in 5 mM $NH_4CO_3$/25 mM NaCl, pH 8. Left vial, composition before a 5 min 45° C. heating step; middle vial, after heating and 0.2 μm sterile filtration; right vial, reconstitution of precipitate after adding potassium phosphate to a final concentration of 50 mM;

FIG. 10 shows reconstitution of particulate IC31® following sterile filtration of a more concentrated nanoparticulate IC31® composition. Nanoparticulate IC31® 3.3× high (3300 nmol/mL KLK/132 nmol/mL ODN1a) was formulated in 5 mM Tris/25 mM NaCl, pH 6. Left vial, appearance of the composition before a 5 min 45° C. heating step; middle vial, the composition after heating and 0.2 μm sterile filtration; right vial, reconstitution of precipitate after adding potassium phosphate to a final concentration of 50 mM;

FIG. 11 shows 1D-NMR analysis of 1000 nmol/mL KLK formulated in 5 mM Tris/25 mM NaCl, pH 8 before and after heating. Compared with the unheated composition (FIG. 11a), KLK at 45° C. (FIG. 11b) shows a reduction of signals on both sides of the graph, indicating a reduction in the number of particles from both extremes; FIG. 11a, 5° C.; FIG. 11b, 45° C.;

FIG. 12 shows 1D-NMR analysis at 5° C. of a 40 nmol/mL ODN1a composition in 5 mM Tris/25 mM NaCl, pH 8. A characteristic signal for base pair bands can be seen at 15 ppm, demonstrating that ODN1a forms double strands by base pairing. This peak disappears when the sample is warmed to 20° C., indicating a melting of the double strand (data not shown);

FIG. 13 shows 1D-NMR analysis at 5° C. of IC31® high (1000 nmol/mL KLK/40 nmol/mL ODN1a) formulated in 5 mM Tris/25 mM NaCl, pH 8. Only signals characteristic of KLK (see FIG. 11 for reference) are observed, whereas no ODN1a signal at 15 ppm is detected, indicating that no appreciable base pairing of ODN1a occurs in IC31®;

FIG. 14 shows CD spectrograms of 1000 nmol/mL KLK in water, 40 nmol/mL ODN1a in water and nanoparticulate IC31® high (1000 nmol/mL KLK/40 nmol/mL ODN1a) formulated 5 mM Tris/25 mM NaCl, pH 7, or 5 mM $NH_4CO_3$/10 mM NaCl, pH 7.5, before and after a 5 min heating step at 45° C. No change in the overall secondary structure of KLK can be observed in these nanoparticulate compositions, illustrating that KLK has the same β-sheet conformation in both IC31® compositions before and after heating;

FIG. 15 shows CD spectrograms of nanoparticulate IC31® high (1000 nmol/mL KLK/40 nmol/mL ODN1a) formulated in 5 mM Tris/10 mM NaCl, pH 7, before heating (20° C.) and during the 45° C. heating step after one and 5 minutes. No overall change in the secondary structure was observed.

Figure 16:
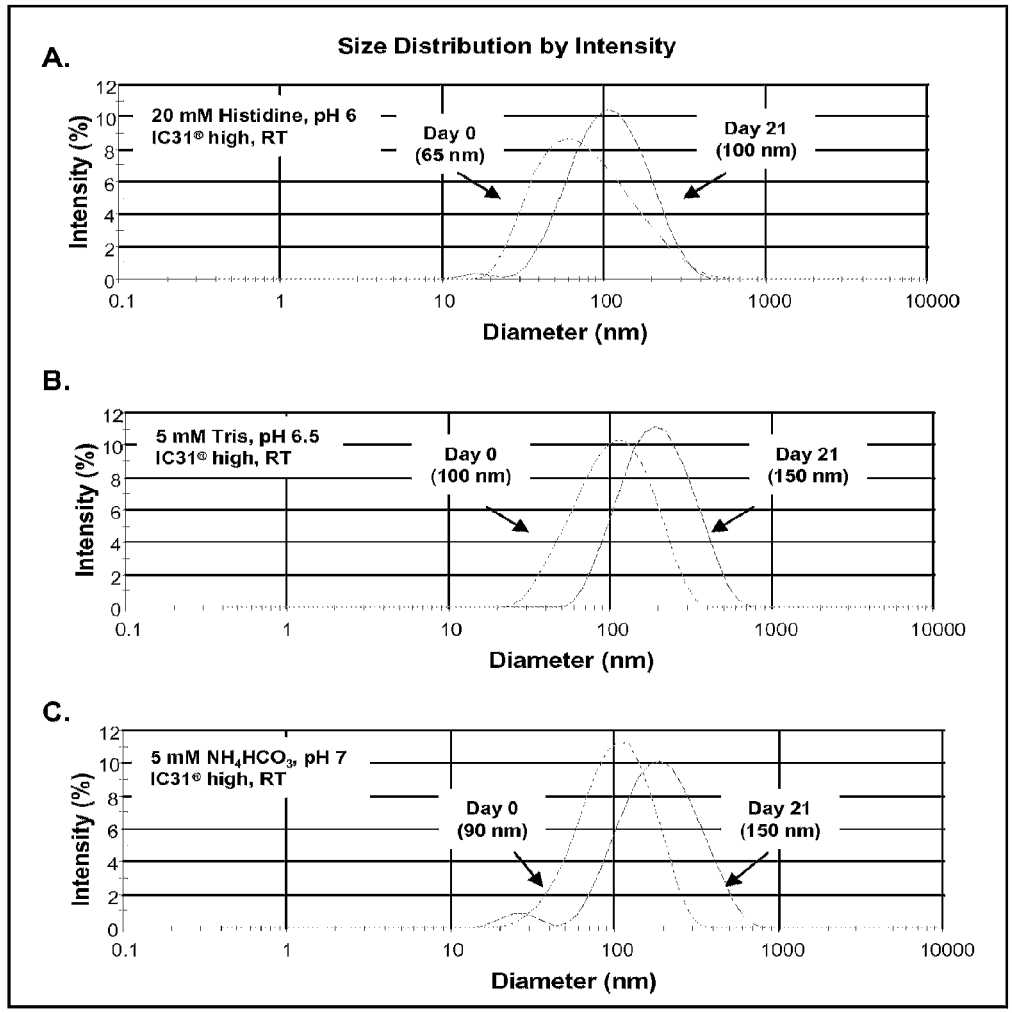

FIG. 16 shows the mean particle sizes of IC31® high (1000 nmol/mL KLK/40 nmol/mL ODN1a) compositions directly after mixing (day 0) and on day 21 after storage at RT; 20 mM Histidine, ph 6 (A); 5 mM Tris, pH 6.5 (B); 5 mM $NH_4HCO_3$, pH 7 (C).

Figure 17:
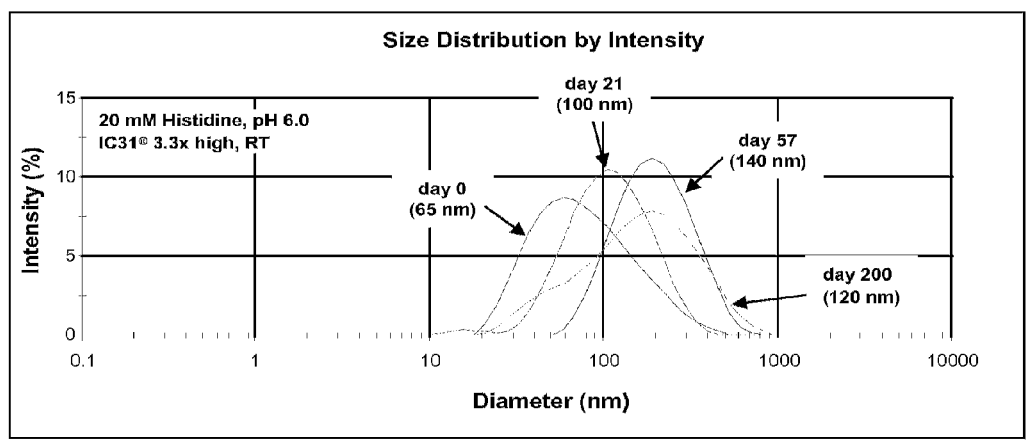

FIG. 17 shows particle size stability of IC31® 3.3× high (3300 nmol/mL KLK/132 nmol/mL ODN1a) formulated in 20 mM Histidine, pH 6.0, on the day of formulation (day 0) and after 21, 57, and 200 days storage at RT.

Figure 18A:
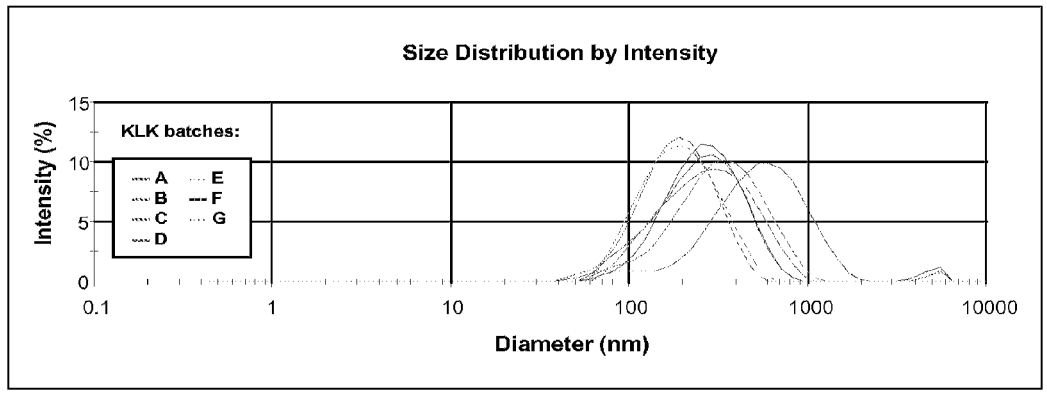
Figure 18B:
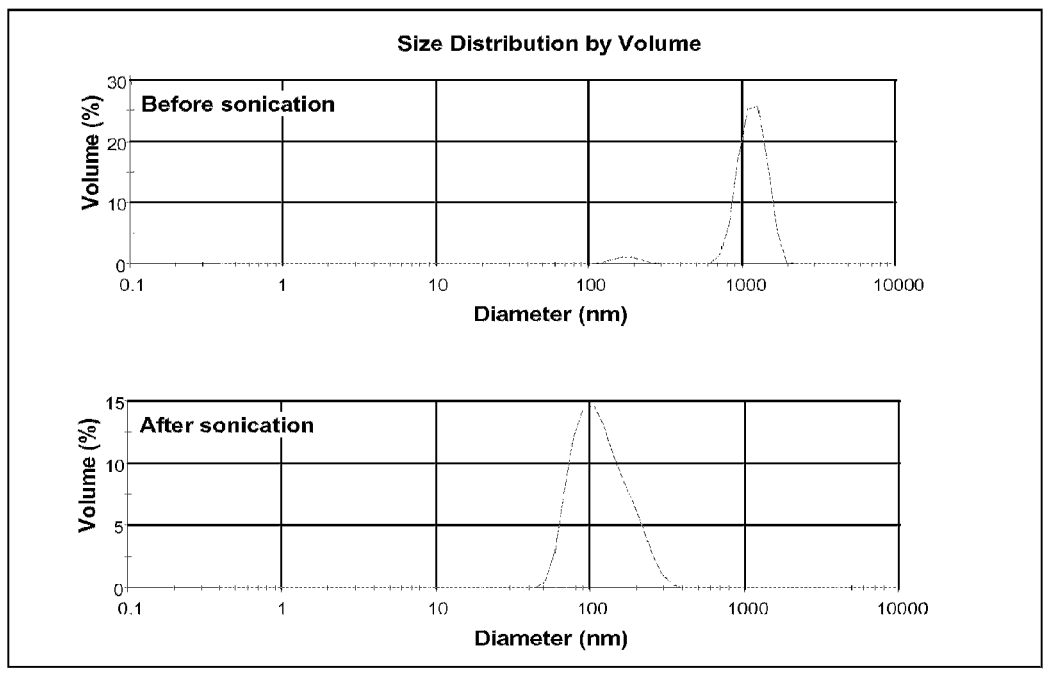

FIG. 18a shows the variable size of IC31® high (1000 nmol/mL KLK/40 nmol/mL ODN1a) nanoparticles made with different batches of KLK (see also Table 11), when formulated in WFI and heated to 45° C. for 10 minutes (FIG. 18a). FIG. 18b shows the particle size of IC31® high (1000 nmol/mL KLK/40 nmol/mL ODN1a) in WFI before energy input (upper graph) and after 5 (1 sec) pulses of sonication with a probe sonicator (lower graph).

Figure 19:
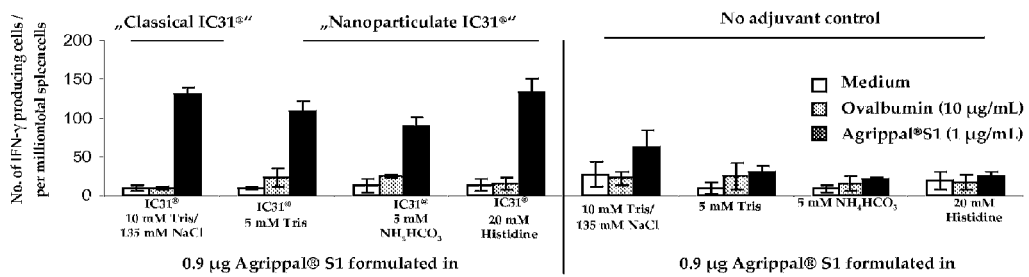
Figure 20:
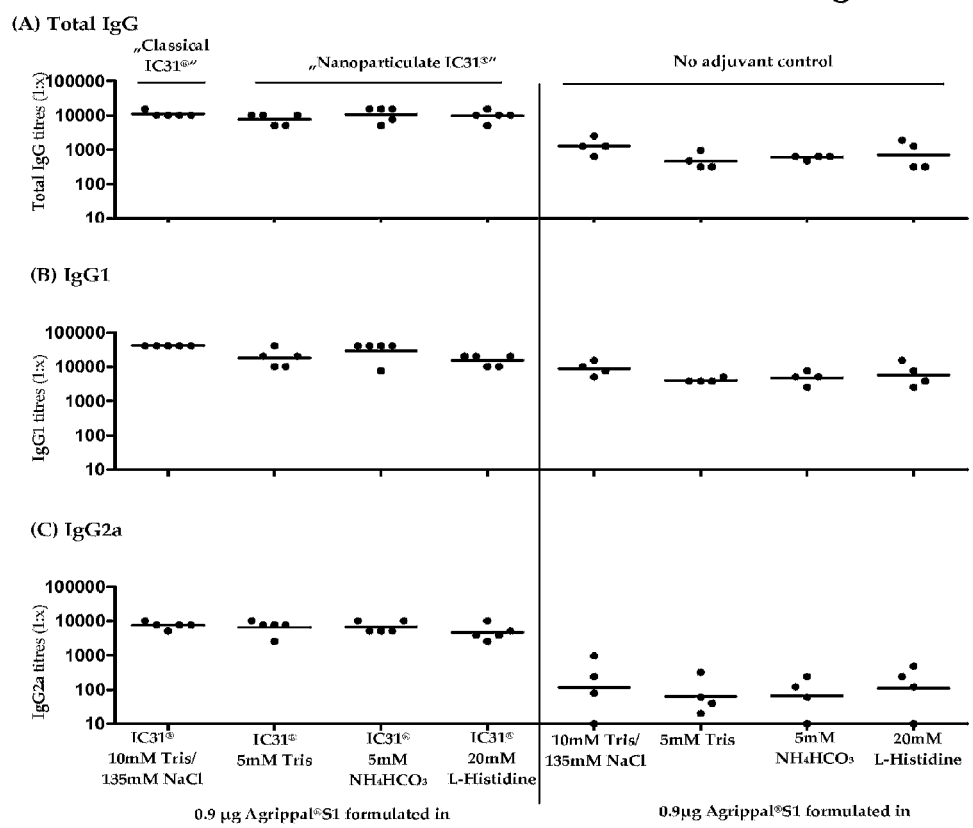
Figure 21:
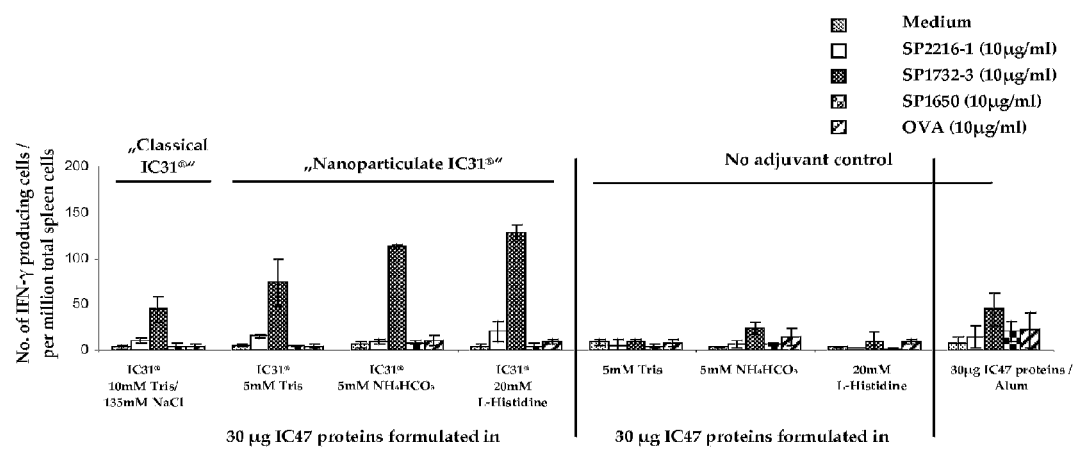
Figure 22:
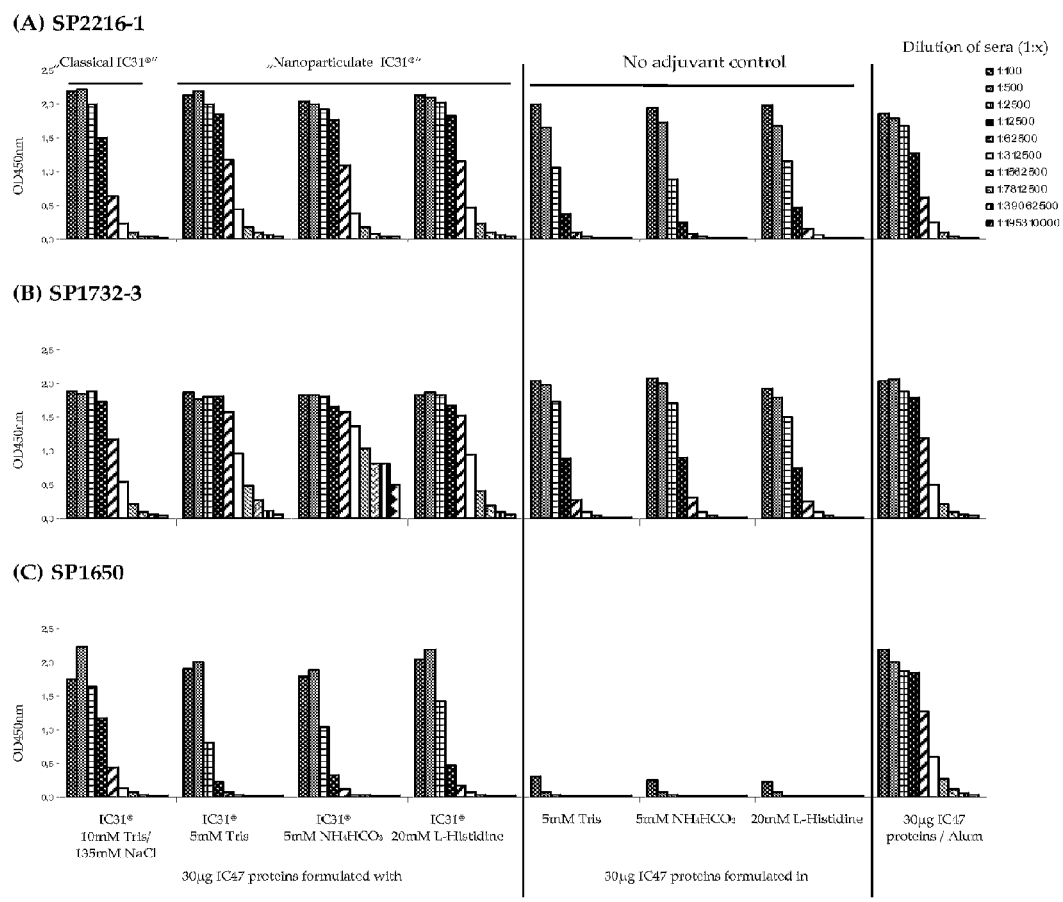
Figure 23:
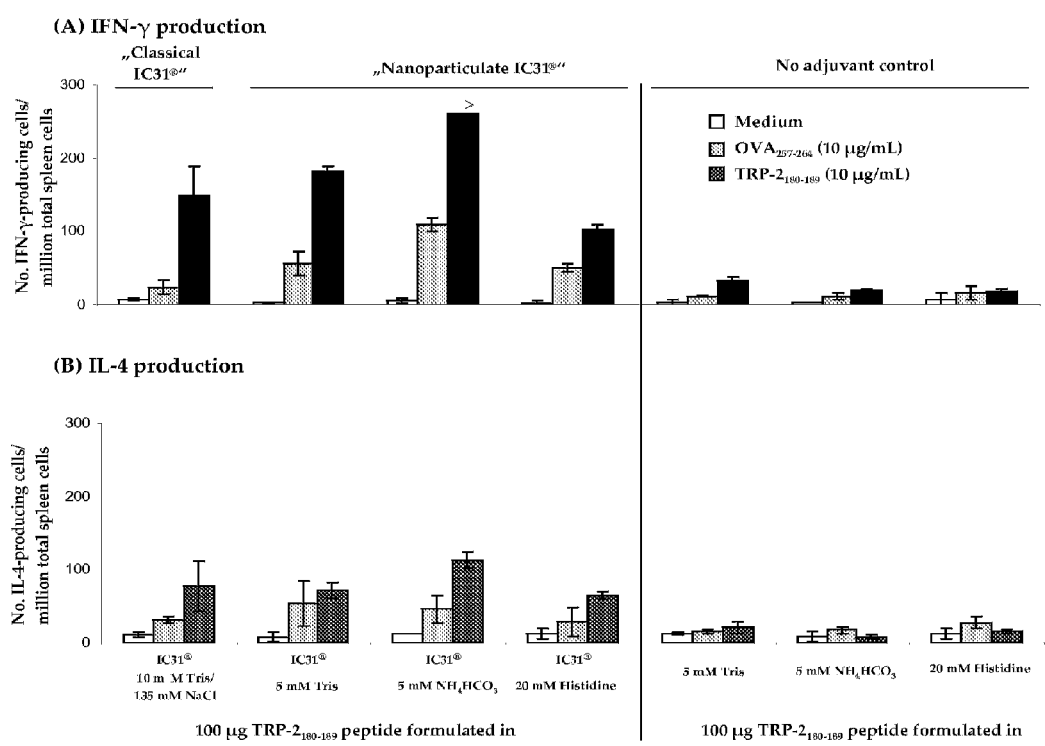
Figure 24:
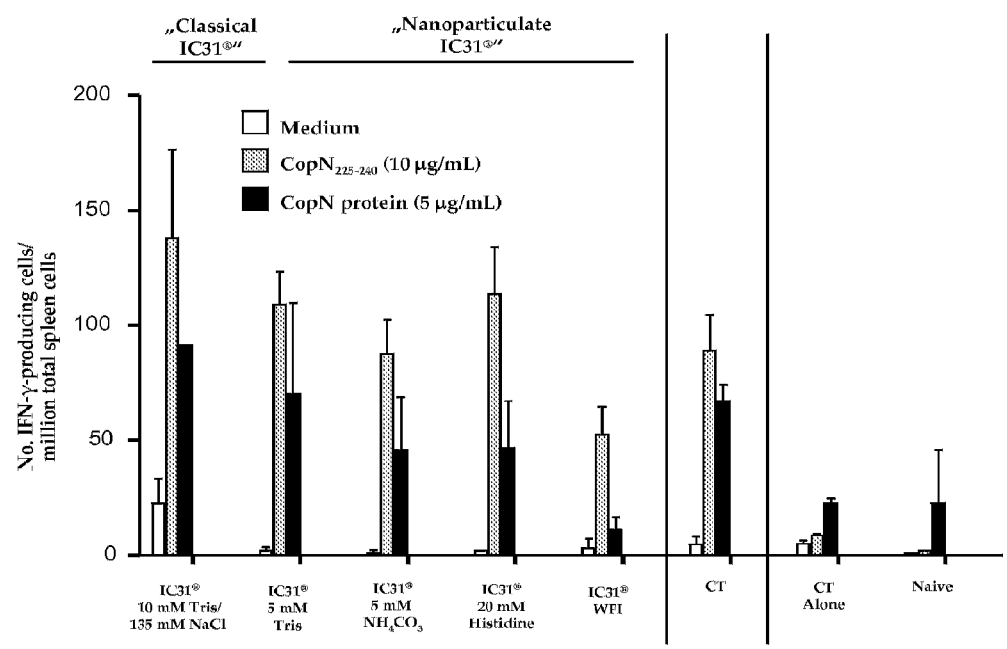

FIG. 19 shows IFN-γ production by total spleen cells: BALB/c mice were immunized intra-muscularly (i.m.) with 0.9 μg Agrippal® S1 alone or in combination with IC31® (100 nmol KLK/4 nmol ODN1a per mouse) formulated in 10 mM Tris/135 mM NaCl, pH 7.5-8 (classical IC31®), 5 mM Tris, pH 7.5, 5 mM $NH_4HCO_3$, pH 8, or 20 mM Histidine buffer, pH 6 (nanoparticulate IC31® formulations). On day 21, splenocytes were analyzed for influenza vaccine-specific IFN-γ producing cells by ELISpot. For each experimental group, 5×10⁵ cells were plated in triplicate and re-stimulated ex vivo with medium (negative control), OVA (10 μg/mL, irrelevant antigen) or Agrippal®S1 (1 μg/mL). Results are expressed as numbers of vaccine-specific cytokine-producing cells per 1×10⁶ total spleen cells (mean of triplicates±standard deviation);

FIG. 20 shows serum total IgG, IgG1 and IgG2a antibody responses: BALB/c mice were immunized (i.m.) with 0.9 μg Agrippal® S1 alone or in combination with classical or nanoparticulate IC31® (100 nmol KLK/4 nmol ODN1a per mouse) formulated in 10 mM Tris/135 mM NaCl, pH 7.5-8 (classical IC31®), 5 mM Tris, pH 7.5, 5 mM $NH_4HCO_3$, pH 8, or 20 mM Histidine buffer, pH 6 (nanoparticulate IC31® formulations). On day 21, blood samples of individual mice were collected and total IgG (A), IgG1 (B) and IgG2a (C) serum antibodies were determined by ELISA. Antibody titres represent the reciprocal of the dilution of serum yielding half maximal $OD_{405}$ values (linear interpolation);

FIG. 21 shows antigen-specific IFN-γ production by total spleen cells: C3H/He mice were immunized sub-cutaneously (s.c.) on day 0 and day 14 with 30 μg IC47 S. pneumoniae vaccine (10 μg/mouse each of SP2216-1, SEQ ID NO 3; SP1732-3, SEQ ID NO 4; SP1650, SEQ ID NO 5) alone or in combination with classical or nanoparticulate IC31® (100 nmol KLK/4 nmol ODN1a per mouse) formulated in 10 mM Tris/135 mM NaCl, pH 7.5-8 (classical IC31®), 5 mM Tris, pH 7.5, 5 mM $NH_4HCO_3$, pH 8, or 20 mM Histidine buffer, pH 6 (nanoparticulate IC31® formulations). The Alum-adjuvanted S. pneumoniae vaccine was used for comparison. On day 21, splenocytes were analyzed for IC47 protein-specific IFN-γ producing cells using ELISpot assays. For each experimental group, 5×10⁵ cells were plated in triplicate and re-stimulated ex vivo with medium (negative control), OVA protein (10 μg/mL, irrelevant antigen) or indicated IC47 proteins (10 μg/mL, SP2216-1, SP1732-3, SP1650). Results are expressed as numbers of protein-specific cytokine-producing cells per 1×10⁶ cells (mean of triplicates±standard deviation);

FIG. 22 shows serum total IgG antibody responses: C3H/He mice were immunized (s.c.) on day 0 and day 14 with 30 μg IC47 S. pneumoniae vaccine (10 μg/mouse of SP2216-1, SP1732-3, SP1650) alone or in combination with classical or nanoparticulate IC31® (100 nmol KLK/4 nmol ODN1a per mouse) formulated in 10 mM Tris/135 mM NaCl, pH 7.5-8, 5 mM Tris, pH 7.5, 5 mM $NH_4HCO_3$, pH 8, or 20 mM Histidine buffer, pH 6. Alum-adjuvanted S. pneumoniae vaccine was used for comparison. On day 21, blood samples were collected (pool of 5 mice/group) and total IgG serum anti-bodies specific for SP2216-1 (A), SP1732-3 (B) and SP1650 (C) were determined by ELISA;

FIG. 23 shows IFN-γ and IL-4 production by total spleen cells: C57BL/6 mice were immunized (s.c.) with 100 μg TRP-2$_{180-189}$ peptide (SEQ ID NO 6) alone or in combination with classical or nanoparticulate IC31® (100 nmol KLK/4 nmol ODN1a per mouse) formulated in 10 mM Tris/135 mM NaCl, pH 7.5-8 (classical IC31®), 5 mM Tris, pH 7.5, 5 mM $NH_4HCO_3$, pH 8, or 20 mM Histidine buffer, pH 6 (nanoparticulate IC31® formulations). On day 21, splenocytes were analyzed for IFN-γ (A) and IL-4 (B) producing cells by ELISpot. For each experimental group, 5×10⁵ cells were plated in triplicate and re-stimulated ex vivo with medium (negative control), OVA$_{257-264}$ (10 μg/mL, irrelevant antigen, SEQ ID NO 7) or TRP-2$_{180-189}$ (10 μg/mL). Results are expressed as numbers of cytokine producing cells per 1×10⁶ cells (mean of triplicates±standard deviation);

FIG. 24 shows IFN-γ production by total spleen cells: C57BL/6 mice were immunized (s.c.) with 50 μg CopN$_{226-240}$ peptide (SEQ ID NO 8) adjuvanted with classical or nanoparticulate IC31® (100 nmol KLK/4 nmol ODN1a per mouse) formulated in 10 mM Tris/135 mM NaCl, pH 7.5-8 (classical IC31®), 5 mM Tris, pH 7.5, 5 mM $NH_4HCO_3$, pH 8, 20 mM Histidine buffer, pH 6, or WFI (nanoparticulate IC31® formulations). One group of mice was immunized with the peptide adjuvanted in CT (10 μg). On day 7, mice were given a booster immunization. A week after the second dose, splenocytes were analyzed for IFN-γ producing cells using ELISpot assays. For each experimental group, 2.5×10⁵ and 5×10⁵ cells were plated in triplicate and re-stimulated ex vivo with medium (negative control), CopN$_{226-240}$ peptide (10 μg/mL) or recombinant CopN (5 μg/mL). Results are expressed as numbers of cytokine producing cells per 1×10⁶ cells (mean of triplicates±standard error).

Figure 25:
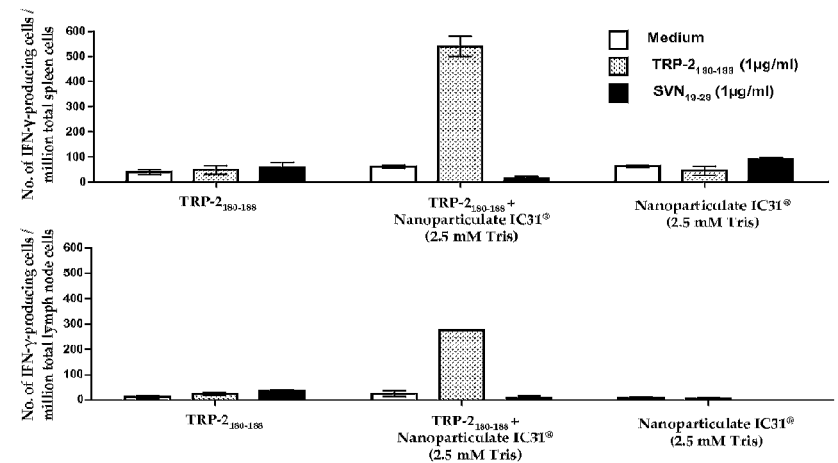
Figure 25:
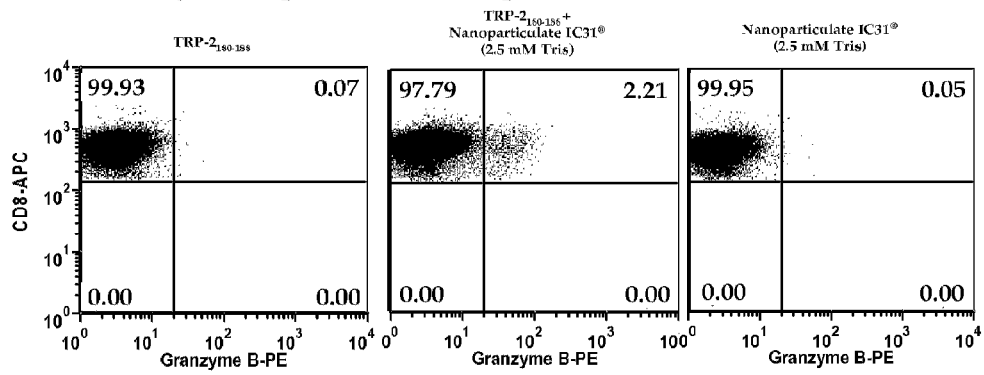

FIG. 25A shows IFN-γ production by total spleen cells and lymph node cells: C57BL/6 mice were immunized intradermally (i.d.) with 60 μg TRP-2$_{180-189}$ peptide alone, 60 μg TRP-2$_{180-189}$ peptide adjuvanted with nanoparticulate IC31® (100 nmol KLK/4 nmol ODN1a per mouse) formulated in 2.5 mM Tris, pH 7.0, or nanoparticulate IC31® alone. On days 13 and 28, mice were given booster immunizations. Two weeks after the second booster, splenocytes and lymph node cells were analyzed for IFN-γ producing cells using ELISpot assays. For each experimental group, $2.5 \times 10^5$ and $5 \times 10^5$ cells were plated in triplicate and re-stimulated ex vivo with medium (negative control), TRP-$2_{180-189}$ peptide (1 μg/mL) or SVN$_{19-28}$ peptide (1 μg/mL; irrelevant peptide, SEQ ID NO 9). Results are expressed as the number of cytokine producing cells per $1 \times 10^6$ cells (mean of triplicates±standard error). FIG. 25B shows the cell-surface expression of the cytolytic marker Granzyme B by CD8$^+$ spleen cells. Mice were treated as for FIG. 25A, cells were analyzed by flow cytometry after staining with Allophycocyanin-labeled anti-mouse CD8 antibodies (CD8-APC; x axis) and Phycoerythrin-labeled anti-mouse Granzyme B antibodies (Granzyme B-PE; y axis).

Figure 26:
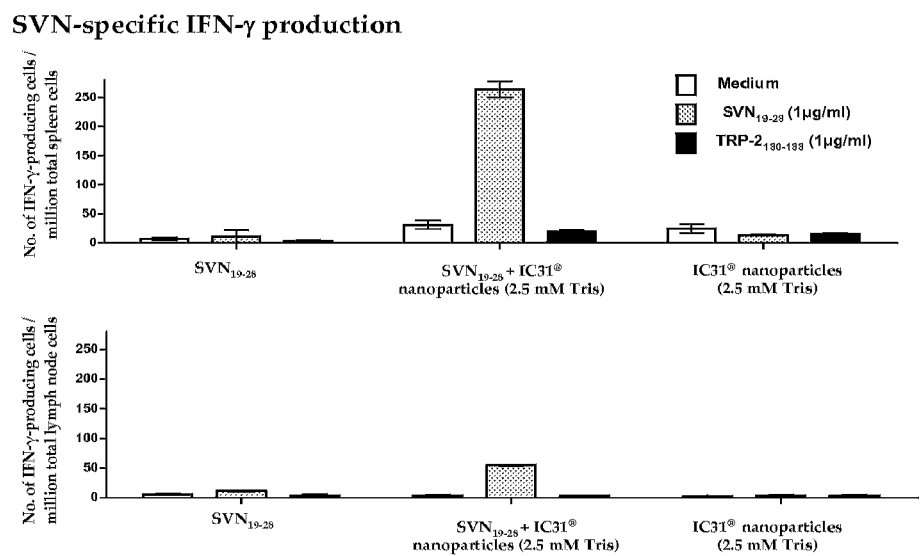

FIG. 26 shows IFN-γ production by total spleen cells and lymph node cells: C57BL/6 mice were immunized intradermally (i.d.) with 60 μg SVN$_{19-28}$ peptide alone, 60 μg SVN$_{19-28}$ peptide adjuvanted with nanoparticulate IC31® (100 nmol KLK/4 nmol ODN1a per mouse) formulated in 2.5 mM Tris, pH 7.0, or nanoparticulate IC31® alone. On days 13 and 28, mice were given booster immunizations. Two weeks after the second booster, splenocytes and lymph node cells were analyzed for IFN-γ producing cells using ELISpot assays. For each experimental group, $2.5 \times 10^5$ and $5 \times 10^5$ cells were plated in triplicate and re-stimulated ex vivo with medium (negative control), SVN$_{19-28}$ peptide (1 μg/mL) or TRP-$2_{180-189}$ peptide (1 μg/mL; irrelevant peptide). Results are expressed as the number of cytokine producing cells per $1 \times 10^6$ cells (mean of triplicates±standard error).

EXAMPLES

TABLE 1A

Abbreviations and terms used in the Examples.

| Abbreviation/Term | Explanation/Definition |
|---|---|
| KLK | KLKL$_5$KLK, peptide component of IC31 ® |
| ODN1a | (dIdC)$_{13}$, oligodeoxynucleotide component of IC31 ® |
| IC31 ® | Adjuvant, a mixture of KLK and ODN1a |
| IC31 ® Low | 100 nmol/mL KLK/4 nmol/mL ODN1a |
| IC31 ® Medium | 350 nmol/mL KLK/14 nmol/mL ODN1a |
| IC31 ® High | 1000 nmol/mL KLK/40 nmol/mL ODN1a |
| IC31 ® 3.3x high | 3300 nmol/mL KLK/132 nmol/mL ODN1a |
| Sterile filtration | Filtration using a 0.2 μm filter |
| Autoclaving | Heating for 20 min at 121° C. |
| Tris | Tris(hydroxymethyl)aminomethane |
| WFI | Water For Injection |
| MES | 2-(N-morpholino)ethanesulfonic acid |
| MOPS | 4-morpholinopropanesulfonic acid |
| PSD | Particle Size Distribution |
| TRP | Tyrosinase-related protein |
| CopN | Chlamydial outer protein N |
| CT | Cholera toxin |
| SVN | Survivin |
| OVA | Ovalbumin |

TABLE 1B

Sequences included in the Examples.

| SEQ ID NO | Type | Name | Sequence |
|---|---|---|---|
| 1 | Peptide | KLK | KLKLLLLLKLK |
| 2 | ODN | ODN1a | (dIdC)$_{13}$ |
| 3 | Protein | SP2216-1 | ETTDDKIAAQ DNKISNLTAQ QQEAQKQVDQ IQEQVSAIQA EQSNLQAEND RLQAESKKLE GEITELSKNI VSRNQSLEKQ ARSAQTNGAV TSYINTIVNS KSITEAISRV AAMSEIVSAN NKMLEQQKAD KKAISEKQVA NNDAINTVIA NQQKLADDAQ ALTTKQAELK AAELSLAAEK ATAEGEKASL LEQKAAAEAE ARAAAVAEAA YKEKRASQQQ SVLASANTNL TAQVQAVSES AAAPVRAKVR P |
| 4 | Protein | SP1732-3 | YLILLASLVL VAASLIWILS RTPATIAIPD VAGQTVAEAK ATLKKANFEI GEEKTEASEK VEEGRIIRTD PGAGTGRKEG TKINLVVSSG KQSFQISNYV GRKSSDVIAE LKEKKVPDNL IKIEEEESNE SEAGTVLKQS LPEGTTYDLS KATQIVLTVA KKATTIQLGN YIGRNSTEVI SELKQKKVPE NLIKIEEEES SESEPGTIMK QSPGAGTTYD VSKPTQIVLT VAKKVTSVAM PSYIGSSLEF TKNNLIQIVG IKEANIEVVE VTTAPAGSVE GMVVEQSPRA GEKVDLNKTR VKISIYKPKT TSATP |
| 5 | Protein | SP1650 | ASGKKDTTSG QKLKVVATNS IIADITKNIA GDKIDLHSIV PIGQDPHEYE PLPEDVKKTS EADLIFYNGI NLETGGNAWF TKLVENAKKT ENKDYFAVSD GVDVIYLEGQ NEKGKEDPHA WLNLENGIIF AKNIAKQLSA KDPNNKEFYE KNLKEYTDKL DKLDKESKDK FNKIPAEKKL IVTSEGAFKY PSKAYGVPSA YIWEINTEEE GTPEQIKTLV EKLRQTKVPS LFVESSVDDR PMKTVSQDTN IPIYAQIFTD SIAEQGKEGD SYYSMMKYNL DKIAEGLAK |

TABLE 1B-continued

Sequences included in the Examples.

| SEQ ID NO | Type | Name | Sequence |
|---|---|---|---|
| 6 | Peptide | TRP-2$_{180-189}$ | SVYDFFVWL |
| 7 | Peptide | OVA$_{257-264}$ | SIINFEKL |
| 8 | Peptide | CopN$_{226-240}$ | DRYTYQDMAIVSSFL |
| 9 | Peptide | SVN$_{19-28}$ | IATFKNWPFL |

Example 1

Development of a Stable Sub-Micron IC31®
Composition: Applying Standard Techniques to
Reduce Particle Size of IC31® Precipitates 1.1 Objective When generating a classical IC31® formulation, KLK precipitates immediately after blending with ODN1a and buffer salts. As a result, the classical IC31® formulation cannot be 0.2 μm sterile filtered. Therefore, the two components are dissolved separately in water (KLK) or buffer/salt solution (ODN1a) and sterile filtered before combining (see FIG. 1). Consequently, all subsequent steps must be done under aseptic conditions, complicating the production process considerably.

The aim of this project was the development of a method to generate sterile IC31® compositions after mixing, eliminating the need for subsequent aseptic processes.

A number of approaches described in the art to reduce particle size were investigated, including heat sterilisation, radioactive inactivation and physical disruption of the particles.

1.2 Introduction & Study Description

Figure 1:
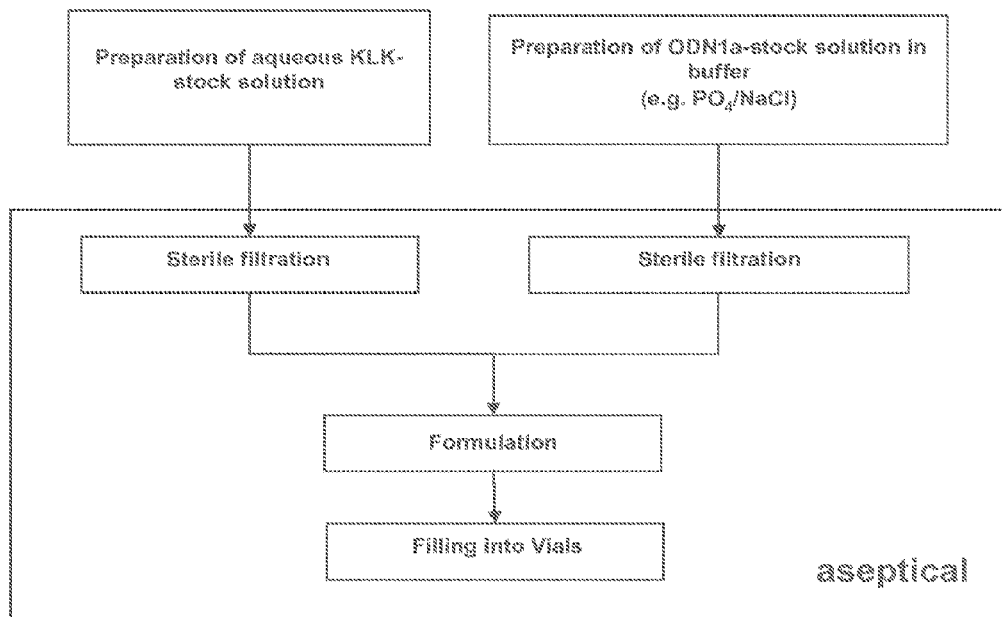
FIG. 1 shows the procedure for production of classical GMP-grade IC31®.

The classical formulation of the adjuvant IC31® is a 25:1 molar mixture of a short peptide (KLK) and an oligodeoxynucleotide (ODN1a) in a physiologic buffer solution containing 135 mM NaCl and either 5 mM phosphate or 10 mM Tris at a pH of 7.5 to 8. The current process of classical IC31® GMP material production is shown in FIG. 1. As the blending of the ingredients results in an immediate precipitation of KLK with a mean particle diameter of 5 to 50 μm, the final product cannot be 0.2 μm sterile filtered. Thus, most steps of the formulation process must be performed under aseptic conditions.

It would therefore be a significant improvement of the process if the particle size of the precipitate could be reduced to less than 0.2 μm to enable a final sterile filtration step thereby removing the need for a completely aseptic process. To explore this possibility, a number of different homogenization methods described in the art were evaluated for their effectiveness to decrease the precipitate's particle size. Additionally, approaches that, according to the information available in the prior art, could lead to a simplified formulation process were tested as well. These included heat sterilisation by autoclaving and γ-sterilisation similar to the process currently used for aluminium hydroxide.

Influences on the stability of the IC31® components KLK and ODN1a were monitored, as well as effects on particle size and optical appearance. Furthermore, physical changes, such as increased viscosity, were analysed as well.

1.3 Materials and Methods 1.3.1 Materials
KLK stock solutions
ODN1a stock solutions
Bench autoclave
γ-radiation facility at Seibersdorf, Austria
Ultra-Turrax IKA T25 Digital High-performance disperser
Panda 2K Niro Soavi high pressure homogenizer
Microfluidics Processor M-110F
Precision thermometer "DIGITAL" VWR NA82021-152 EU 609-0908
Malvern Mastersizer 2000pP
Wyatt Technology Dyna Pro Titan DLS system
Waters Alliance 2695 XESepModWolf HPLC system
Eppendorf pipette, "Research", variable; 200-1000 μL
Eppendorf pipette, "Research", variable; 20-200 μL
Eppendorf pipette, "Research", variable; 10-100 μL
Eppendorf pipette, "Research", variable; 2-20 μL
Water for Injection 1.3.2 Methods
Turbidity measurements: UV spectrometer adsorption at 550 nm
Dynamic light scattering: Malvern Zetasizer Nano ZS with Dispersion Technology Software 5.10
Determination of mean particle size: Measured in Zetasizer using Dispersion Technology Software 5.10
Sterilisation using γ-radiation: Gamma radiation (e.g. Co60) is used to kill microbes. Usual doses are in the range of 25 kGy.
Heat sterilisation: Classical IC31® formulations at low (100 nmol/mL KLK/4 nmol/mL ODN1a), medium (350 nmol/mL KLK/14 nmol/mL ODN1a) and high (1000 nmol/mL KLK/40 nmol/mL ODN1a) concentrations in 5 mM phosphate or 10 mM Tris buffer with 135 mM NaCl were filled in heat-resistant glass vials (1 mL/vial) and autoclaved at 121° C. for 20 min. Following cooling to room temperature, the samples were analysed for KLK and ODN1a recovery and for mean particle size.
High speed homogenization: Classic IC31® formulations (5 mM phosphate/135 mM NaCl or 10 mM Tris/135 mM NaCl) were subjected homogenization by two different methods: high-speed homogenization, using an Ultra-Turrax at 10000-25000 rpm for 1-5 minutes, or high-pressure homogenization using a Panda 2K Niro Soavi high pressure homogenizer at 1500 bar or a Microfluidizer at 1000-5000 bar for several cycles.
Reduction of particle size by sonication: Typical sonication conditions for 1 mL IC31® sample: 1 sec pulse/5 sec swirl with 4 repeats in an ice bath with a Virtis 100 sonicator and VirSonic 100 (3 mm) probe. Sonication conditions for a 25 mL IC31® sample: 5 minutes on ice at 4.5% of maximum setting on a Bandelin Sonoplus sonicator, using a 10 mm probe.

1.4 Results
1.4.1 Physical Characterization of Current Composition

Figure 2:
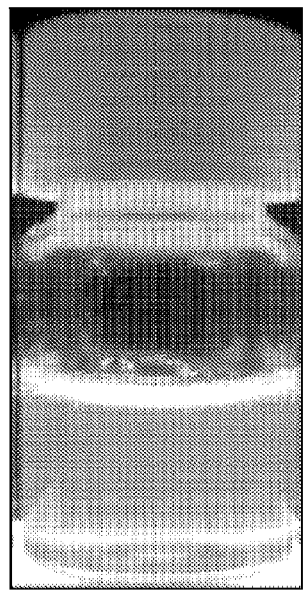
FIG. 2 illustrates the particulate nature of classical IC31® high (1000 nmol/mL KLK/40 nmol/mL ODN1a) formulated in 5 mM phosphate/135 mM NaCl, pH 7.5.

The classic IC31® formulation is a white turbid solution with a precipitate consisting of the two components: KLK and ODN1a (FIG. 2). In this composition, a constant molar ratio of 25 parts KLK to 1 part ODN1a is used together with two alternative buffer systems, 5 mM phosphate/135 mM NaCl, pH 7.5, or 10 mM Tris/135 mM NaCl, pH 7.5. Whereas both KLK and ODN1a are separately quite soluble in water and can easily be sterile filtered, KLK precipitates immediately after mixing with either ODN1a or with buffer alone, presumably due to electrostatic interactions with either the charges of the ODN1a backbone or the salt and buffer ions. Also, precipitation can be due to excess free KLK forming insoluble complexes with phosphate ions.

Figure 3:
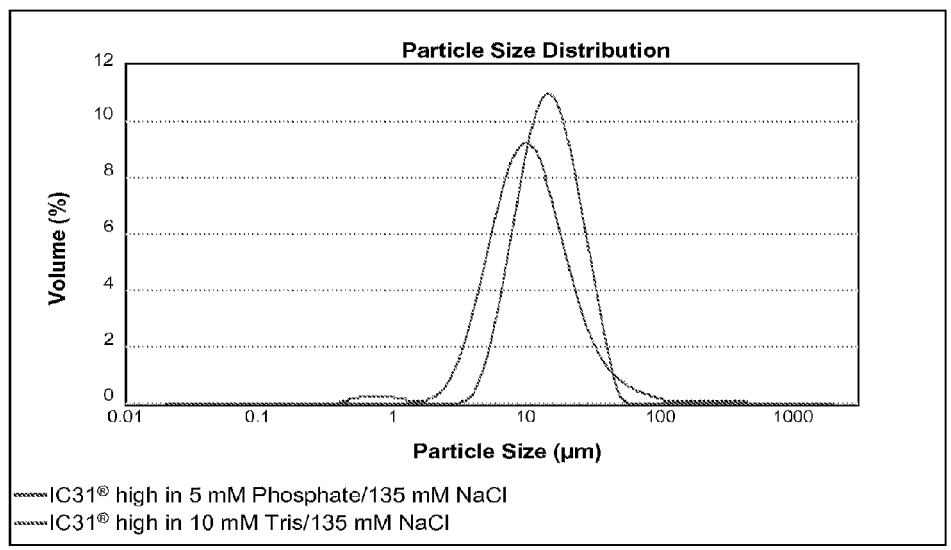
FIG. 3 shows the mean particle diameter of a lab-scale formulation of classical IC31® high (1000 nmol/mL KLK/40 nmol/mL ODN1a) formulated in either 10 mM Tris/135 mM NaCl, pH 7.5 (green line), or in 5 mM phosphate/135 mM NaCl, pH 7.5 (red line)

The mean particle diameter of this precipitate is dependent on external factors such as the strength and duration of stirring after blending and differs with the buffer system employed. On average, a particle size of 5 to 50 μm is observed by light scattering (FIG. 3). GMP produced material has a mean particle diameter of 5 to 20 μm, reflecting the more pronounced stirring (and thereby grinding) of the precipitate.

1.4.2 Sterilisation of Compositions After Blending

Two different methods were evaluated for the sterilisation of IC31® compositions after the precipitate has been formed.

The first method was sterilisation using γ-radiation. For this, IC31® high (1000 nmol/mL KLK/40 nmol/mL ODN1a) in Tris and phosphate buffer were filled in 1 mL glass vials with silicon stoppers and irradiated using 10 and 25 kGy at the facilities of Mediscan, Seibersdorf, Austria. As controls, separate vials containing either 1000 nmol/mL KLK or 40 nmol/mL ODN1a in water were tested as well.

Following irradiation, the samples were analysed for optical changes in IC31® or its components, for changes in the particle size, and for stability of the components.

Figure 4:
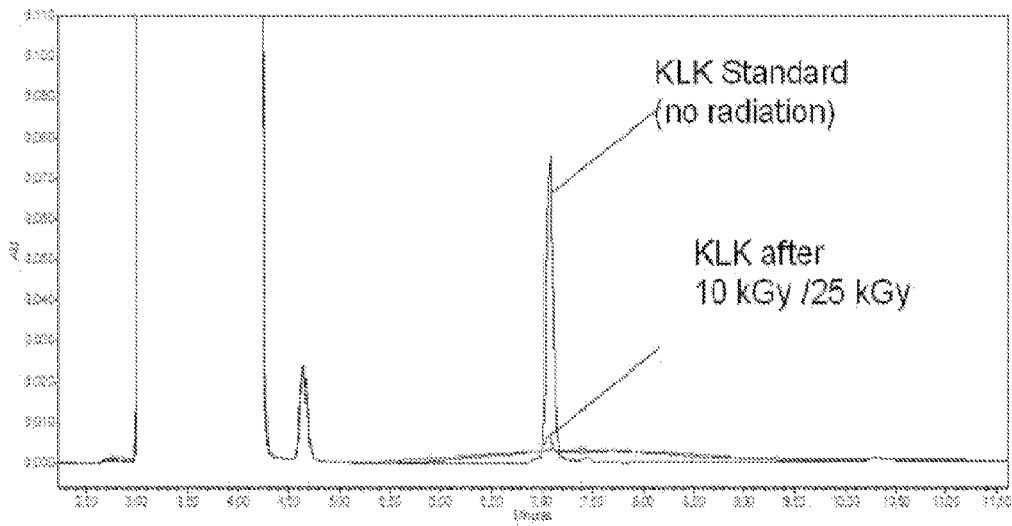
FIG. 4 shows an HPLC trace of reference KLK (1000 nmol/mL) in WFI before and after γ-irradiation, indicating complete degradation of KLK (complete data set is presented in Table 2)

Results of the HPLC recovery analysis are summarized in Table 2 and a sample HPLC analysis of the KLK only control is presented in FIG. 4.

TABLE 2

Summary of HPLC recovery analysis of KLK and ODN1a before and after gamma radiation treatment.

| Sample | KLK recovery (%) | ODN1a recovery (%) |
|---|---|---|
| Standard in water* | 100 | 100 |
| Standard after 10 kGy | 0 | 0 |
| Standard after 25 kGy | 0 | 0 |
| IC31 ® Tris | 100 | 100 |
| IC31 ® Tris after 10 kGy | 43 | 50 |
| IC31 ® Tris after 25 kGy | 12 | 36 |
| IC31 ® Phosphate | 100 | 100 |
| IC31 ® Phosphate after 10 kGy | 69 | 48 |
| IC31 ® Phosphate after 25 kGy | 35 | 26 |

*1000 nmol/mL KLK formulated in WFI and 40 nmol/mL ODN1a formulated in WFI were tested separately. The Tris formulations of classical IC31 ® high (1000 nmol/mL KLK/40 nmol/mL ODN1a) contained 10 mM Tris and 135 mM NaCl. The phosphate formulations contained 5 mM phosphate and 135 mM NaCl.

As can be seen in Table 2, both standards in water were completely destroyed by the radiation procedure. When in complex (precipitated), the two components showed a higher resistance to radiation as, for example, about 70% of KLK in phosphate buffer was recovered after a 10 kGy radiation step. However, these results are unacceptable for a routine procedure. ODN1a showed a similar sensitivity to radiation.

Additionally, differences between the buffers used and changes in the optical properties were observed. Only the particle size was unaffected by the procedure (data not shown).

It can therefore be concluded that γ-sterilisation is not possible for IC31® formulations.

The second method tried was to heat sterilize a final IC31® formulation by simple autoclaving.

The results are summarized in Table 3:

TABLE 3

Summary of HPLC recovery analysis of KLK and ODN1a after autoclaving of classical IC31 ® formulations.

| Buffer | [KLK/ODN1a] (nmol/mL) | KLK recovery (%) | ODN1a recovery (%) |
|---|---|---|---|
| 10 mM Tris 135 mM NaCl | 100/4 (low) | 66 | 65 |
|  | 350/14 (medium) | 84 | 69 |
|  | 1000/40 (high) | 84 | 73 |
| 5 mM phosphate 135 mM NaCl | 100/4 (low) | 68 | 46 |
|  | 350/14 (medium) | 45 | 37 |
|  | 1000/40 (high) | 90 | 64 |

As observed previously for the radiation, the particle size was not affected by autoclaving (data not shown).

In general, the recovery rates were higher at higher IC31® concentrations. However, the recovery of ODN1a was significantly decreased in all samples.

Therefore, heat sterilisation at these conditions cannot be used for IC31® formulations.

1.4.3 Reduction of Particle Size in Final Formulations

Immediately upon blending, KLK forms a white precipitate with a mean particle size of 5 to 50 μm.

These aggregates can be broken down by shearing with a magnetic stirrer to a homogenous population of 1-10 μm particles. If relatively mild shearing can decrease the particle size already quite strongly, it suggests that more rigorous shearing might result in submicron particles.

To test this hypothesis, two different homogenization instruments were evaluated for their ability to decrease IC31® particle size.

An Ultra-Turrax IKA T 25 Digital high-speed disperser was used at different velocities ranging from 1000-25000 rpm to homogenize classical IC31® formulations. As can be seen in FIG. 5, it was indeed possible to reduce the IC31® aggregates to sub-micron particles of about 0.3-0.5 μm by homogenization with the Ultra-Turrax (5 minutes at 25000 rpm, red trace). However, when the same sample was analysed 5 days later, the mean particle diameter was in the 1-5 μm range (green trace). Thus the particles re-aggregated very quickly after shearing, indicating that sub-micron particles generated by the above method are unstable, particularly in the 5 mM phosphate/135 mM NaCl or 10 mM Tris/135 mM NaCl buffered solutions.

Furthermore, it was not possible to reduce all aggregates to the submicron level. A small number of particles remained in the 1-10 μm range; however, these particles contained about 90% of the total mass of KLK and ODN1a present in the formulation. Thus, this method cannot be used for the generation of sterile-filterable IC31® compositions.

High pressure homogenization of IC31® with the Panda 2K Niro Soavi homogenizer efficiently reduced the mean particle size within one to two cycles; however, it was ineffective at reducing the size to less than 1 μm even in the short-term, as can be seen in FIG. 6.

Due to the above results, it was concluded that physical breaking of the aggregates by shearing is not sufficient to generate stable nanoparticulate IC31® compositions.

1.4.4 Reduction of Particle Size by Sonication

As can be seen in FIG. 7, sonication rapidly and efficiently disrupts the larger particles in classical IC31®, generating particles of about 0.2-0.3 µm. Nonetheless, similar to observations following homogenization by shearing, a small but significant number of particles were not reduced in size by sonication. Again, as these larger particles contain more than 90% of the KLK and ODN1a in the solution, this method cannot be used to generate sterile-filterable IC31® compositions.

Example 2

Development of Stable Nanoparticulate IC31® Compositions: Selection of Appropriate Buffer Components and Reduction of Ionic Strength 2.1 Reduction of Ionic Strength in Phosphate-Buffered IC31®

As none of the mechanical means to decrease IC31® particle size were successful, changes in other parameters of the IC31® formulations were investigated. Surprisingly, changes in buffer composition and ionic strength showed promising results, although some formulations without any buffer or salt or with phosphate buffers having a low ionic strength resulted in precipitation.

In the absence of buffer or salt, KLK does precipitate when mixed with ODN1a, but to a much lower extent than in the classical IC31® formulations. However, when the resulting precipitate is removed by 0.2 µm sterile filtration, although about 70% of the KLK is recovered, ODN1a cannot be detected. One possible explanation for this could be that KLK complexed with ODN1a in water forms larger particles than KLK alone.

The addition of just 2 mM phosphate to the formulation, however, results in the loss of detectible KLK in solution. The effect of salts such as NaCl at higher concentrations is similar, though not as pronounced.

Since the addition of very small concentrations of phosphate precipitated KLK quantitatively, it was decided to study the influence of buffer composition in more depth by using only Tris buffer. When testing a large number of different salt and Tris buffer concentrations, additives, stirring speeds and pH values, two compositions were identified that did not show any visible precipitation (FIG. 8 and Table 4).

TABLE 4

Composition and mixing conditions of the four compositions shown in FIG. 8. In samples A-C, the IC31 ® concentration was 800 nmol/mL KLK/10 nmol/mL ODN1a. Sample D was formulated as for classical IC31 ® high (1000 nmol/mL KLK/40 nmol/mL ODN1a).

| Sample | [NaCl] (mM) | [Tris] (mM) | Tween 20 (%) | Stirring (rpm) | pH | Precipitate |
|--------|-------------|-------------|--------------|----------------|-----|-------------|
| A      | 25          | 10          | 0            | 400            | 6   | No          |
| B      | 250         | 10          | 0.4          | 100            | 8   | Yes         |
| C      | 25          | 10          | 0.4          | 100            | 6   | No          |
| D      | 135         | 10          | 0            | 0              | 7.6 | Yes         |

When using the standard IC31® high concentration (1000 nmol/mL KLK/40 nmol/mL ODN1a), these results could only partially be reproduced. It was therefore necessary to revise the molecular background for this composition in order to decide on further steps.

2.2 Development of a Molecular Model

It was shown previously that membrane-penetrating peptides, when attached to lipids, change their secondary structure if the sample is heated to 35-40° C. (Aichinger et al., Cell Biology International 32 (2008), 1449-1458). Furthermore, circular dichroism analysis of KLK indicated a similar structural transition of KLK from a β-sheet to an α-helix when KLK penetrated cell membranes or liposomes (Su et al., J. Mol. Biol. 381 (2008), 1133-1144).

The current model for IC31® indicates that KLK is present in a β-sheet conformation. These β-sheets can form β-stacks, thus leading to the formation of large aggregates (the precipitate) which include the ODN1a molecules in an unordered fashion.

It was therefore hypothesized that energy input, such as a moderate heating step, could induce a β-sheet to transition to an α-helical conformation. As the α-helical KLK molecules cannot form large aggregates, the precipitate should be broken and then only free KLK and ODN1a would be in solution. This composition could then be 0.2 µm sterile filtered and, upon cooling, KLK would convert back to a β-sheet conformation and would precipitate. As shown in 2.1 above (Table 4 and FIG. 8), the two compositions that had low concentrations of salt and buffer remained in suspension without forming a precipitate, whereas medium and high concentrations of ions resulted in precipitation. It was therefore concluded that the concentration of ions must be lowered substantially to prevent precipitation.

2.3 Proving of the Molecular Model and Generation of Nanoparticulate IC31®

To test the model, a number of IC31® high (1000 nmol/mL KLK/40 nmol/mL ODN1a) compositions with various buffer systems (Table 5) and salts (Table 6) were generated and heated for 5 minutes at 45° C. As can be seen from these tables, phosphate or acetate buffers as well as magnesium or calcium salts should not be used for the preparation of IC31® compositions according to the present invention.

However, in compositions with low salt and buffer ion strength, the degree of precipitation is already quite low upon mixing. This low degree of precipitation is apparent in FIG. 9, left vial, which shows IC31® high (1000 nmol/mL KLK/40 nmol/mL ODN1a) formulated in 5 mM Phosphate/25 mM NaCl. This composition could not be sterile filtered, however, as the filter would immediately be clogged by the particles. After increasing the temperature of the composition to 45° C. for 5 minutes, however, the solution cleared and could be 0.2 µm sterile filtered without any problems and with back pressure similar to highly purified water (FIG. 9, middle vial).

HPLC recovery analysis of KLK and ODN1a showed a recovery above 95% for both components after heating and filter sterilising, demonstrating that the clear solution does not contain considerable numbers of particles larger than 0.2 µm.

Unexpectedly, the solution remained clear even after several days' storage at 2-8° C. As the absence of precipitate could potentially have an impact on the biological properties of IC31® (e.g., depot formation, effectiveness), a reconstitution of the composition to its original precipitated state was attempted.

To this end, potassium phosphate to a final concentration of 50 mM was added to the clear filter-sterilised solution. This indeed resulted in precipitation (FIG. 9, right vial).

Analysis of the heated and filtered composition using dynamic light scattering showed that the composition contained particles in the 0.02-0.2 µm range (data not shown). Additionally, the DLS measurements showed a prominent peak at a particle size of 0.1-1 nm corresponding to a molecular weight of 1-10 kDa (the weight of single KLK and ODN1a molecules) (data not shown). However, as light scattering becomes unreliable at this size range, it cannot be stated with certainty that this is a real signal. The reconstituted formulation, by contrast, contained particles in the micrometer range and were thus indistinguishable from classical IC31®.

One can presume that the particles in these formulations should be similar in their composition and structure to the large particles in the original formulation.

To test if the heating procedure is effective on IC31® compositions more concentrated than IC31® high (1000 nmol/mL KLK/40 nmol/mL ODN1a), an IC31® 3.3× high composition was prepared (3300 nmol/mL KLK, 132 nmol/mL ODN1a) in 5 mM Tris/25 mM NaCl. As can be seen in FIG. 10, the 5 minute 45° C. heating step, as well as the subsequent reconstitution of precipitate with 50 mM phosphate ions, was also effective with the IC31® 3.3× high composition.

This demonstrates that heat-induced clearance of the precipitate is effective over a wide range of IC31® concentrations. However, the biophysical model formulated in section 2.2 is at least partly wrong, as CD measurements presented below indicate that there is no change in secondary structure induced by the heating step. This indicates that KLK does not change from a beta-sheet to an alpha-helical state upon heating, as it has been shown in the presence of lipids.

2.4 Biophysical Characterization of Nanoparticulate IC31® Compositions 2.4.1 NMR Analysis of Changes in Secondary Structure Analysis of 1000 nmol/mL KLK in 5 mM Tris buffer with 25 mM NaCl by 1D-NMR revealed that, with increasing temperature, a number of signals disappear as the rigid KLK structure becomes more flexible (FIG. 11a (5° C.) and b (45° C.)).

Additionally, 1D-NMR analysis of 40 nmol/mL ODN1a in 5 mM Tris/25 mM NaCl at 5° C. revealed a peak at 15 ppm, which is characteristic of base pair interactions (FIG. 12). This peak was abolished when the sample was warmed to 20° C. (data not shown), suggesting that the interaction is weak. The remaining signals did not change with increasing temperature, indicating no further change in the structure of ODN1a.

Analysis of IC31® in Tris buffer by 1D-NMR showed only signals characteristic of KLK (FIG. 13). With an increase in temperature, these signals changed identically to those observed in the KLK analysis (see FIG. 11 for reference), indicating that only KLK signals were observable. The absence of a base pair peak at 15 ppm suggests that, in IC31®, double-stranded ODN1a is not present.

2.4.2 CD Spectroscopy Analysis Shows that There is No Change in Secondary Structure It has been shown previously that KLK forms a random coil in water, and takes on a β-sheet conformation when mixed in phosphate buffer or when mixed with ODN1a. When KLK interacts with membrane-like structures such as small unilamellar membranes (SUV), its structure becomes α-helical (Aichinger et al., Cell Biology International 32 (2008), 1449-1458). The same can be seen when hygroscopic agents such as Trifluorethanol (TFE) are added. When in an α-helical conformation, KLK does not precipitate.

Therefore, it is reasonable to hypothesize that the rapid dissolution of the precipitate may be the result of a β-sheet to α-helix transition of KLK. To test this, heat-treated IC31® compositions were analyzed by CD spectroscopy to determine if heating influences KLK secondary structure. Two nanoparticulate IC31® compositions were prepared and analyzed directly after mixing or after a heating step.

As shown in FIG. 14, KLK in water is present in a standard random coil conformation. Analysis of the two nanoparticulate IC31® compositions revealed that the precipitated KLK in the non-heated formulations displays a β-sheet secondary structure as expected. When the same samples are heated, however, the (now soluble) KLK shows a β-sheet conformation identical to the one observed for non-heated IC31®, regardless of the buffer system used. This demonstrates that the secondary structure of KLK is not affected by the heating step, but rather remains unchanged.

To test for changes in KLK secondary structure during the heating step, IC31® was analyzed first at 20° C., followed by heating of the sample to 45° C., and two more measurements were recorded after 1 and 5 minutes incubation at high temperature. As shown in FIG. 15, no change in the secondary structure was observed.

These findings further indicate that there is no change in the KLK secondary structure as a result of the heating step. Consequently, the disruption of the precipitate by the heating step cannot be explained by a change in the secondary structure of KLK.

2.5 Secondary Structure Analysis of KLK

A simple and robust method for the generation of sterile-filterable IC31® compositions has been developed.

It was shown that simple disruption of the precipitate by sonication or high pressure homogenization does not lead to stable sub-micron particle formation.

However, an appropriate energy input, such as a short heating step at moderate temperature, induces a very fast dissolving of the precipitate into <0.2 μm particles. It was shown that a number of different buffer systems such as Tris, $NH_4CO_3$, MOPS, MES and Histidine can be used together with different salts such as NaCl.

Biophysical analysis showed that, in these nanoparticulate compositions, KLK has the same secondary structure as in the original IC31® precipitate. It was furthermore possible to reconstitute the precipitation by the addition of phosphate, resulting in particles of similar size to the original IC31®. This shows that heating does not induce changes in the secondary structure, nor in biophysical or biological characteristics.

It is more likely that during the mixing of the single components, due to local concentration changes, large thermodynamic imbalances occur that are removed by energy introduced into the system with the heating step. This energy would therefore be used to generate the thermodynamic equilibrium that cannot be achieved during the standard formulation reaction.

The presence of only sub-micron particles, as opposed to larger particles, in IC31® might be expected to have an impact on the biological properties observed in classical IC31® studies. For example, with regard to depot formation, nanoparticles may diffuse more readily through the periplasm than classical IC31® particles. In this regard, it may be desired to reconstitute the larger particles of classical IC31® from the nanoparticulate IC31® in order to achieve the same long-lived depot characteristic of IC31® compositions.

For this reason, the possibility of reconstituting the larger particulate nature of IC31® may be a crucial factor in the process.

Example 3

Formulation Parameters for Nanoparticulate IC31®

For the development of nanoparticulate IC31® at lab scale (1-2 mL), sterile PS reaction tubes were used. Each composition was generated by the stepwise addition of each component previously prepared as a concentrated stock solution as follows.

To determine the precise concentration of the stock solution, KLK and ODN1a were dissolved in water at final concentrations of 1000 nmol/mL KLK and 40 nmol/mL ODN1a and analyzed by standard IC31® HPLC methods. Buffer substances were dissolved in water and pH-adjusted using HCl or NaOH. Buffer salts were dissolved in water.

Generation of each nanoparticulate IC31® composition was done using a standardized formulation sheet as described below.

First, the appropriate buffer stock solution was pipetted into a 1.5 or 2 mL reaction tube, salt solutions were added if required and, finally, WFI was added. After thoroughly mixing, ODN1a was added and the composition was mixed by vortexing. As a final step, KLK was added to the composition, causing the form ation of a white precipitate. The reaction tubes were then transferred to a pre-heated thermo-mixer and incubated at 45° C. for 10 min while shaking, resulting in a clear composition with no visible precipitates.

3.1 pH and Buffer Systems Tested

The following pH and buffer systems were tested:

TABLE 5

The effect of pH on IC31 ® solubility in several buffer systems.

| Buffer system | pH of composition (nanoparticles generated) | | | |
|---|---|---|---|---|
| | 5 | 6 | 7 | 7.5 |
| 10 mM Tris | — | Yes | Yes | No |
| 5 mM MES | Yes | Yes | Yes | — |
| 5 mM MOPS | — | Yes | Yes | — |
| 5 mM Sodium phosphate | No | No | No | No |
| 20 mM Histidine | — | Yes | Yes | No |
| 5 mM Sodium acetate | No | No | No | — |
| 10 mM Ammonium bicarbonate | — | — | — | Yes |

Yes = generation of nanoparticulate IC31 ® possible;
No = generation of nanoparticulate IC31 ® not possible;
— = not tested.
In all cases the compositions were IC31 ® high (1000 nmol/mL KLK/40 nmol/mL ODN1a).

The addition of phosphate or acetate buffer resulted in the generation of an IC31® precipitate that could not be re-dissolved by the subsequent heating step. Thus, these buffer systems are considered non-compatible with nanoparticulate IC31® compositions, at least under the conditions used for these experiments (see below).

For the further development of nanoparticulate IC31® compositions for mouse studies, three buffer systems were chosen: 10 mM Tris, pH 7.2, 20 mM Histidine, pH 6, and 10 mM Ammonium bicarbonate, pH 7.8.

3.2 Salt Systems Tested

The following buffer salts were tested in final molar concentrations of 0-50 mM. The highest possible concentration compatible with IC31® nanoparticle formation is stated for the three chosen buffer systems.

TABLE 6

Highest tolerated concentrations of various salts in the tested buffer systems with IC31 ® high (1000 nmol/mL KLK/40 nmol/mL ODN1a).

| | Highest tolerated [salt] (mM) | | | | |
|---|---|---|---|---|---|
| Buffer | NaCl | MgCl$_2$ | KCl | MgSO$_4$ | CaCl$_2$ |
| 10 mM Tris, pH 7 | 25 | 0 | 10 | 0 | 0 |
| 20 mM Histidine, pH 6 | 25 | 0 | 10 | 0 | 0 |
| 10 mM Ammonium bicarbonate, pH 8 | 25 | 0 | 10 | 0 | 0 |

3.3 Use of Citrate and Phosphate Buffers

Citrate and phosphate are commonly used buffers. The impact of citrate and phosphate ions on nanoparticulate IC31® compositions was tested in more detail.

Nanoparticulate IC31® compositions were generated in 10 mM Tris buffer and increasing amounts of citrate or phosphate were added. Precipitation caused by the addition was measured by monitoring the turbidity of the composition at 550 nm. In this regard, an $OD_{550}$ value of >0.2 correlates with the composition being non-sterile-filterable. A summary of the data is provided in Table 7.

TABLE 7

Effect of citrate and phosphate ions on IC31 ® nanoparticle formation in Tris and Histidine buffers. In all cases, IC31 ® high (1000 nmol/mL KLK/40 nmol/mL ODN1a) was used. Effect of citrate and phosphate on sterile-filterability

| | Sterile-filterable | |
|---|---|---|
| | 10 mM Tris, pH 7 | 10 mM Histidine, pH 6 |
| [Citrate] (mM) | | |
| 0 | Yes | Yes |
| ≥1 | No | No |
| [PO$_4$] (mM) | | |
| 0 | Yes | Yes |
| ≥1 | No | No |

Therefore, the addition of phosphate or citrate buffer at concentrations ≥1 mM results in the formation of IC31® aggregates in the micromolar size range and, consequently, a non-sterile-filterable formulation. The formed precipitate consists of KLK and is independent of the presence of ODN1a.

However, the resulting particles show a size distribution very similar to that of classical IC31®, indicating that, by the addition of phosphate buffer to nanoparticulate IC31®, for example, during mixing of an antigen with IC31® for the final formulation, may result in a formulation which is very similar to a mixture of classical IC31® with the same antigen. Consequently the observed immune reaction should be comparable.

3.4 Correlation of Viscosity and pH in a Tris-Buffered System

One of the key factors for sterile-filterable compositions is viscosity. At a viscosity >15 cP, sterile filtration through a 0.2 μm filter is no longer possible. The final viscosity of the nanoparticulate IC31® composition correlates to the final pH of the composition due to the fact that the viscosity of KLK in solution increases drastically with increasing pH, resulting in non-sterile-filterable formulations at a final pH of around 7.2.

TABLE 8 pH and viscosity in Tris compositions.
Effect of pH on the viscosity of KLK formulated in 10 mM Tris

| pH | Viscosity (cP) | Sterile-filterable |
|---|---|---|
| 6.24 | 9.69 | Yes |
| 6.4 | 8.06 | Yes |
| 6.6 | 10.00 | Yes |
| 6.73 | 10.00 | Yes |
| 6.88 | 10.94 | Yes |
| 7.03 | 11.25 | Yes |
| 7.22 | 15.00 | Yes/No* |
| 7.39 | 16.88 | No |
| 7.7 | 16.88 | No |
| 7.96 | 25.00 | No |

TABLE 8-continued pH and viscosity in Tris compositions.
Effect of pH on the viscosity of KLK formulated in 10 mM Tris

| pH | Viscosity (cP) | Sterile-filterable |
|---|---|---|
| 8.4 | 21.88 | No |
| 8.4 | 24.38 | No |
| 8.8 | 87.50 | No |

*Note: solutions with a viscosity >15 cP cannot be 0.2 μm sterile filtered.
The KLK concentration was 2000 nmol/mL and no salt was included.

3.5 Optimising the Minimal Concentration of Buffer in Tris, pH 7.2 and Histidine, pH 6 Buffer Systems If KLK and ODN1a are mixed in water without any buffer or salt ions and without any energy input, the same precipitate is formed as in classical IC31® and in IC31® compositions according to the present invention prior to the energy input step(s). However, the formed precipitate can be dissolved by one or more appropriate energy input steps. Additionally, as described above, IC31® formulated in WFI without any ions may require more energy input than IC31® compositions with a low ion concentration and may be less stable. Thus, the presence of small amounts of ions is preferred for the generation of nanoparticulate IC31®.

Suitable concentrations of Tris and Histidine at the given pH were determined as summarized in Table 9.

TABLE 9

Optimization of buffer concentrations for nanoparticulate
IC31 ® compositions. In all cases, IC31 ® high
(1000 nmol/mL KLK/40 nmol/mL ODN1a) was used.
Effect of Tris and Histidine concentration on particle size

| | Particle size (Diameter in nm) | Sterile-filterable |
|---|---|---|
| Formulated in [Tris] (mM), pH 7.2 | | |
| 1 | >500 | No |
| 2 | >130* | No |
| 3 | 91 | Yes |
| 4 | 77 | Yes |
| 5 | 73 | Yes |
| 6 | 72 | Yes |
| 7 | 70 | Yes |
| 10 | 87 | Yes |
| Formulated in [Histidine] (mM), pH 6 | | |
| 1 | >180* | No |
| 2 | >110* | No |
| 3 | 105 | Yes |
| 4 | 104 | Yes |
| 5 | 101 | Yes |
| 6 | 99 | Yes |
| 7 | 100 | Yes |
| 20 | 83 | Yes |

*bimodal distribution with larger particles present

It was observed that at least 3 mM of Tris or Histidine is required for the successful generation of nanoparticulate IC31®.

For the generation of larger volumes of nanoparticulate IC31® (up to 25 mL), a water bath was used successfully. However, active stirring of the solution was required. For scaling up the process, the addition of a high-pressure homogenization device was tested successfully. Due to the shear force applied during homogenization, the solution temperature was increased to >40° C., resulting in the generation of comparable nanoparticles as for the simple heating step.

From these results it is also evident that optimisation of the compositions according to the present invention is easily possible with the teachings given herein. This may lead to slightly different cut-off values for ion concentrations, depending on the pH or the buffer system used.

3.6 Particle Size Stability of IC31® Nanoparticles Formulated in Tris, Ammonium Bicarbonate or Histidine Buffers The stability of nanoparticulate compositions in terms of the size of the particles, from a process standpoint, is a critical parameter. Therefore, particle size stability of IC31® nanoparticles formulated in three different buffer systems was assessed after 21 days at room temperature. Nanoparticulate IC31® 3.3× high (3300 nmol/mL KLK/132 nmol/mL ODN1a) was formulated in 5 mM Tris, pH 6.5, 5 mM $NH_4HCO_3$, pH 7, and 20 mM Histidine, pH 6. The compositions were heat-treated for 10 min at 45° C. in respective buffers without salt. As shown in FIG. 16, all three IC31® nanoparticle compositions showed particle size stability at this timepoint.

A longer room temperature stability study was performed with Tris- and Histidine-buffered IC31® 3.3× high. The results of this study are shown in Table 10. The actual analysis of mean particle sizes of the Histidine-buffered composition is shown in FIG. 17. In short, the particles tend to become somewhat larger over time but, within the time-frame tested, were still in the sterile-filterable range.

TABLE 10

Stability of the particle diameter of two different
compositions of nanoparticulate IC31 ® over
time at room temperature storage (particle diameter in nm).

| | Stability of IC31 ® particle size at room temperature | | | |
|---|---|---|---|---|
| Sample | Day 0 | Day 21 | Day 57 | Day 200 |
| 5 mM Tris, pH 6.5 | 100 | 150 | 170 | Not done |
| 20 mM Histidine, pH 6.0 | 60 | 95 | 140 | 120 |

3.7 Formulation of Nanoparticulate IC31® in Water for Injection-Grade Water

When it was investigated whether mixing of KLK and ODN1a in water leads to the formation of nanoparticles, the results were variable. Compositions of IC31® high (1000 nmol/mL KLK/40 nmol/mL ODN1a) in WFI, made from different lots of KLK, were heated for 10 min at 45° C. exactly as for the compositions in buffer. It was discovered that the size of the particles in these compositions, to some extent, correlated inversely with the amount of acetate in the KLK stock (see Table 11 and FIG. 18). Acetate is present as a by-product of peptide synthesis. FIG. 18 shows the particle size distribution of IC31® particles formulated in WFI with each of the KLK batches and their acetate content listed in Table 11. As can be derived from Table 11, all WFI compositions resulted in nanoparticulate IC31® compositions. In some cases, even sterile-filterable nanoparticulate IC31® was successfully formulated in WFI. These compositions were tested in selected adjuvanticity studies below (see FIG. 24).

TABLE 11

Several characteristics of KLK peptide are variable from batch to batch.

| Label in FIG. 18a | KLK Lot No. | KLK(powder) acetate content | pH of final composition* | IC31® particle diameter (nm)* |
|---|---|---|---|---|
| A | 1008793 | 18.2% | 5.2 | 235 |
| B | 1014078 | 13.7% | 6.1 | 173 |
| C | 1013247 | 15.3% | 5.6 | 214 |
| D | 1011705 | 19.6% | 5.1 | 288 |
| E | 570280 | 10.5% | 6.5 | 410 |
| F | 566842 | 12.0% | 6.6 | 249 |
| G | 1004278 | 12.1% | 6.4 | 175 |

*IC31® high (1000 nmol/mL KLK/40 nmol/mL ODN1a) in WFI.

Example 4

Adjuvanticity of Novel Nanoparticulate IC31® Compositions

In order to test the adjuvanticity of novel nanoparticulate IC31® compositions according to the present invention as injectables in combination with model antigens in mouse strains of different genetic backgrounds, the following antigens were tested. In all experiments, antigen mixed with a classical IC31® formulation was included as a control.
Protein antigens: Agrippal®S1 (BALB/c, H-$2^d$)
Protein antigens: IC47 composed of three S. pneumoniae proteins SP2216-1, SP1732-3 and SP1650 (C3H/He, H-$2^k$)
Peptide antigen: TRP-$2_{180-189}$ (C57BL/6, H-$2^b$) (CD8$^+$CTL peptide)
Peptide antigen: CopN$_{226-240}$ (C57BL/6, H-$2^b$) (CD4$^+$Th peptide)
Peptide antigen: SVN$_{19-28}$ (C57BL/6, H-$2^b$) (CD8$^+$CTL peptide)
IC31® Compositions
IC31® was formulated in the following buffer systems:
Classical IC31® formulation:
    10 mM Tris/135 mM NaCl, pH 7.5
Nanoparticulate IC31® compositions:
    2.5 mM Tris, pH 7
    5 mM Tris, pH 7
    5 mM NH$_4$HCO$_3$, pH 7.8
    20 mM Histidine, pH 6
    WFI
Note: The nanoparticulate compositions did not contain any other added salt. Additionally, after mixing, the compositions were heated at 40° C. for 5-10 minutes depending on the volume, and then sterile filtered. Antigens were added aseptically directly before immunization of mice.
4.1 Comparison of the Adjuvanticity of Classical IC31® and Nanoparticulate IC31® Compositions in Combination with the Subunit Influenza Vaccine Agrippal®S1 (Season 2008/2009) in BALB/c Mice
4.1.1 Materials & Methods
Agrippal® S1
The trivalent seasonal subunit influenza vaccine Agrippal®S1 (non-adjuvanted, Novartis Vaccines, batch No 83505) was commercially purchased in pre-filled, single dose syringes and stored in the dark at 4-8° C. The three viral strains in these vaccines where those recommended by the World Health Organisation for the influenza season 2008/2009 (45 μg total haemagglutinin (HA)/500 μL, corresponding to 15 μg HA/viral strain):

A/Brisbane/59/2007-corresponding strain (H1N1) (A/Brisbane/59/2007 IVR-148)
A/Brisbane/10/2007-corresponding strain (H3N2) (A/Uruguay/716/2007 NYMC X-175C)
B/Florida/4/2006-corresponding strain (B/Florida/4/2006)
Vaccination of Mice
Five BALB/c mice per group (6-8 weeks of age, Harlan Winkelmann) were immunized intramuscularly (i.m.) with a total volume of 100 μL final vaccine composition per mouse (50 μL/hind limb). All animal experiments were conducted according to Austrian guidelines (BGB1 No 108/2000 & 136/2001).
ELISA
Blood samples of isofluorane-anaesthetized mice were collected via orbital sinus/plexus.
Antigen-specific total IgG, IgG1 and IgG2a serum antibodies of individual mice were determined by sandwich ELISA. Briefly, 96-well Maxisorp microtiter plates (Nunc Immunoplate) were coated overnight with the influenza vaccine Agrippal®S1 (1 μg/mL) in 0.1 M NaHCO$_3$ (pH 9.2-9.5) at 4° C. The next day, the plates were blocked for 1 hour at 37° C. with 1×PBS/1% BSA. Afterwards, prediluted serum samples were added into the first column of the plate and the titration was continued along the row (1:2-fold serial dilution in 1×PBS/0.1% BSA). After 2 hours of incubation at 37° C. followed by a washing step, biotinylated anti-mouse total IgG, IgG1 or IgG2a antibodies (83.3 ng/mL in 1×PBS/0.1% BSA, Southern Biotechnology Associates) were added and plates were incubated for 1 hour at 37° C. Then, streptavidin-horseradish peroxidase conjugate (0.1 U/mL in 1×PBS/0.1% BSA, Roche Diagnostics) was put onto plates for 30 min at 37° C. and unbound enzyme was washed away afterwards. Plates were developed at RT using ABTS substrate solution (Sigma-Aldrich). The colour intensity was measured at 405 nm (0 nm reference) with a Tecan Sunrise microplate reader. Titres were expressed as the reciprocal of the serum dilution resulting in half maximal signal at OD$_{405}$ nm (linear interpolation).
Haemagglutination Inhibition (HI) Assay
Analysis of neutralizing antibody titres against the individual haemagglutinin antigens of the influenza vaccines was performed using a standard HI assay for human sera. Briefly, 2-fold serially diluted test sera (pool of 5 mice/group) were incubated together with 4 HA units of the respective influenza antigen for 40 minutes at room temperature. Subsequently, human erythrocytes were added for an additional 75 minutes at room temperature, followed by a visual inspection for the inhibition of haemagglutination. The HI titre represents the reciprocal of the last dilution of serum that completely inhibited haemagglutination of erythrocytes.
Cell Preparation & ELISpot Assay
All cells were cultured in complete medium, which is defined as DMEM supplemented with 5% heat-inactivated fetal calf serum (FCS), 2 mM L-glutamine, 1 mM non-essential amino acids, 1 mM sodium pyruvate, 100 μg/mL gentamicin (all components from PAA Laboratories) and 50 μM 2-mercaptoethanol (GIBCO).
Mice were sacrificed by cervical dislocation and spleens were collected. All spleens from animals in the same experimental groups were pooled.
Single cell suspensions were prepared by crushing the respective spleens in complete medium through a cell strainer into a Petri-dish with the aid of a syringe plunger. The cell strainer and the plunger were rinsed with complete medium into the Petri-dish and the flow-through was resuspended and transferred to a new tube. After centrifugation, erythrocytes were lysed with red blood cell lysis buffer (1 mL/spleen, Sigma-Aldrich). The reaction was stopped after 2-3 minutes by adding complete medium, and spleen cells were centrifuged and resuspended in fresh complete medium. After washing, the viable cell count was determined by trypan blue (GIBCO) dye exclusion.

ELISpot plates were coated with cytokine-specific capture antibodies (1 μg/mL, BD Pharmingen) in 0.1 M $NaHCO_3$ (pH 9.2-9.5) overnight at 4° C. On the next day, plates were blocked for 1 hour at 37° C. with 1×PBS/1% BSA. Freshly prepared cells were plated at $5×10^5$ cells per well in triplicate. Plates were incubated at 37° C./5% $CO_2$ in the presence of the influenza vaccine (1 μg/mL), an irrelevant control protein (OVA, 10 μg/mL) or complete medium (background control). Concanavalin A (10 μg/mL, Amersham Biosciences) was used as a positive control. After a 16-h incubation, cells were removed by washing plates three times followed by a 2 h incubation at 37° C. with the respective biotinylated detection antibodies (1 μg/mL; BD Pharmingen) in 1×PBS. After washing, streptavidin-horseradish peroxidase conjugate was added (0.1 U/mL in 1×PBS, Roche Diagnostics). After a 30 min incubation at 37° C., plates were washed and the substrate was added (50 μL per well of a mixture of 0.8 mg/mL DAB, 0.4 mg/mL $NiCl_2$ and 0.015% $H_2O_2$ in 100 mM Tris (pH 7.5)). The reaction was stopped after 10-30 min by washing the plates with tap water. Dried plates were finally analysed using a BIOREADER 5000 and results were expressed as numbers of IFN-γ-producing cells per $1×10^6$ total spleen cells (mean of triplicates±standard deviation).

4.1.2 Results

The purpose of the studies presented herein was to compare the adjuvanticity of classical and nanoparticulate IC31® compositions in conjunction with the non-adjuvanted seasonal subunit influenza vaccine Agrippal®S1 in BALB/c ($H-2^d$) mice upon single immunization. The immunogenicity of the different influenza vaccine/adjuvant compositions were demonstrated by three parameters: induction of specific IFN-γ production by spleen cells (assessed by ELISpot assay), specific total IgG, IgG1, IgG2a serum antibody titres (evaluated by ELISA) and serum haemagglutination inhibition (HI) titres (measured by HI assay).

In summary, a single immunization with Agrippal®S1 combined with classical IC31® (10 mM Tris/135 mM NaCl buffer) or nanoparticulate IC31® (5 mM Tris, 5 mM $NH_4HCO_3$ or 20 mM Histidine buffer) compositions resulted in comparable cellular (FIG. 19) and humoral (antibody production, FIG. 20; HI titers, Table 12) immune responses.

TABLE 12

BALB/c mice were immunized (i.m.) with 0.9 μg Agrippal ® S1 alone or in combination with IC31 ® (100 nmol KLK/4 nmol ODN1a per mouse) formulated in 10 mM Tris/135 mM NaCl (classical IC31 ®), 5 mM Tris, 5 mM $NH_4HCO_3$ or 20 mM Histidine buffer (nano-particulate IC31 ® formulations). On day 21, blood samples of mice were collected and analysed for neutralizing antibodies by HI assay (pooled sera from 5 mice/group). HI titres represent the reciprocal of the last dilution of murine serum that completely inhibits haemagglutination of human erythrocytes.

| Composition | A/H1N1 | A/H3N2 | B |
|---|---|---|---|
| 0.9 μg Agrippal ® S1 + Classical IC31 ® (10 mM Tris/135 mM NaCl) | 160 | 160 | 160 |
| 0.9 μg Agrippal ® S1 + Nanoparticulate IC31 ® (5 mM Tris) | 160 | 160 | 40 |
| 0.9 μg Agrippal ® S1 + Nanoparticulate IC31 ® (5 mM $NH_4HCO_3$) | 160 | 320 | 80 |
| 0.9 μg Agrippal ® S1 + Nanoparticulate IC31 ® (20 mM Histidine) | 160 | 320 | 40 |
| 0.9 μg Agrippal ® S1 + 10 mM Tris/135 mM NaCl | 40 | 80 | 40 |
| 0.9 μg Agrippal ® S1 + 5 mM Tris | 40 | 80 | 80 |
| 0.9 μg Agrippal ® S1 + 5 mM $NH_4HCO_3$ | 20 | 80 | 40 |
| 0.9 μg Agrippal ® S1 + 20 mM Histidine | 80 | 80 | 40 |

4.2 Comparison of the Adjuvanticity of Classical IC31® and Nanoparticulate IC31® Compositions in Combination with a *Streptococcus pneumoniae* Vaccine (IC47) in C3H/He Mice 4.2.1 Materials & Methods

*S. pneumoniae* Vaccine (IC47)

IC47, a non-adjuvanted *S. pneumoniae* vaccine, is composed of 3 proteins: SP2216-1, SP1732-3, SP1650 (Giefing, et al., JEM 205 (2008), 117-131) dissolved in 10 mM Tris/70 mM NaCl/0.067% Tween (batch No. 081DGT01). For comparison, Alum-adjuvanted *S. pneumoniae* vaccine (batch No. 081EA01) was also included in the experimental set-up.

Vaccination of Mice

Five C3H/He mice per group (6-8 weeks of age, Janvier) were immunized twice (day 0/day 14) subcutaneously (s.c.) in the flank with a total volume of 200 μL final vaccine composition per mouse. All animal experiments were conducted according to Austrian guidelines (BGB1 No 108/2000 & 136/2001).

ELISA

Blood samples of isofluorane-anaesthetized mice were collected via the orbital sinus/plexus.

Antigen-specific total IgG serum antibodies were determined by sandwich ELISA. Briefly, 96-well Maxisorp microtiter plates (Nunc Immunoplate) were coated overnight with the individual IC47 proteins (1 μg/mL; SP2216-1, SP1732-3, SP1650) in 1×PBS at 4° C. The next day, the plates were blocked for 1 hour at 37° C. with 1×PBS/1% BSA. Afterwards, pre-diluted serum samples were added to the first column of the plate and the titration was continued along the row (1:5-fold serial dilutions in 1×PBS/0.1% BSA). After 2 hours of incubation at 37° C. followed by a washing step, biotinylated anti-mouse total IgG antibody (83.3 ng/mL in 1×PBS/0.1% BSA, Southern Biotechnology Associates) were added and plates were incubated for 1 hour at 37° C. Then, streptavidin-horseradish peroxidase conjugate (0.1 U/mL in 1×PBS/0.1% BSA, Roche Diagnostics) was put onto plates for 30 min at 37° C. and unbound enzyme was washed away afterwards. Plates were developed at RT using TMB substrate solution (Sigma-Aldrich). The colour intensity was measured at 450 nm (620 nm reference) with a Tecan Sunrise microplate reader.

Cell Preparation & ELISpot Assay

This procedure was carried out exactly as described in 4.1.1, with the exception of the restimulation treatments. In this experiment, cells were incubated with the individual *S. pneumoniae* proteins SP2216-1 (10 µg/mL), SP1732-3 (10 µg/mL), SP1650 (10 µg/mL), an irrelevant control protein (OVA, 10 µg/mL) or complete medium (background control).

4.2.2 Results

The aim of the studies was to compare the adjuvanticity of the classic particulate IC31® formulation with novel nanoparticulate IC31® compositions when delivered with a non-adjuvanted *S. pneumoniae* vaccine (IC47) to C3H/HeN (H-$2^k$) mice. The immunogenicity of the different vaccine/adjuvant compositions was measured by two immunological parameters: induction of specific IFN-γ production by spleen cells (based on ELISpot assay) and protein-specific total IgG serum antibody responses (evaluated by ELISA).

In summary, the tested novel nanoparticulate IC31® compositions (5 mM Tris, 5 mM $NH_4HCO_3$ or 20 mM Histidine buffer) induced comparable or even superior cellular (FIG. 21) and humoral (FIG. 22) immune responses against individual IC47 proteins as the classical IC31® formulation in 10 mM Tris/135 mM NaCl buffer.

4.3 Comparison of the Adjuvanticity of Classical IC31® and Nanoparticulate IC31® Compositions in Combination with the CD8$^+$CTL Peptide TRP-$2_{130-189}$ in C57BL/6 Mice 4.3.1 Materials & Methods TRP-$2_{180-189}$ Peptide Mouse tyrosinase-related protein derived peptide (sequence SVYDFFVWL); dissolved in 100% DMSO; Batch No. MG 27/09/2006

Vaccination of Mice

Five C57BL/6 mice per group (6-8 weeks of age, Janvier) were immunized subcutaneously (s.c.) in the flank with 100 µg TRP-$2_{180}$-189 peptide alone or in combination with classical or nanoparticulate IC31® (100 nmol KLK/4 nmol ODN1a per mouse) formulated in 10 mM Tris/135 mM NaCl, pH 7.5-8 (classical IC31®), 5 mM Tris, pH 7.5, 5 mM $NH_4HCO_3$, pH 8, or 20 mM Histidine buffer, pH 6 (nanoparticulate IC31® formulations) in a total volume of 100 µL final vaccine composition per mouse. All animal experiments were conducted according to Austrian guidelines (BGB1 No 108/2000 & 136/2001).

Cell Preparation & ELISpot Assay

This procedure was carried out exactly as described in 4.1.1, with the exception of the restimulation treatments. In this experiment, cells were incubated with TRP-$2_{180-189}$ (10 µg/mL), an irrelevant control peptide (OVA$_{257-264}$. 10 µg/mL) or complete medium (background control).

ELISpot plates were coated with cytokine-specific capture antibodies (1 µg/mL, BD Pharmingen) in 0.1 M $NaHCO_3$ (pH 9.2-9.5) overnight at 4° C. On the next day, plates were blocked for 1 hour at 37° C. with 1×PBS/1% BSA. Freshly prepared cells were plated at 5×10$^5$ cells per well in triplicates. Plates were incubated at 37° C./5% $CO_2$ in the presence of TRP-$2_{180-189}$ (10 µg/mL), an irrelevant control peptide (OVA$_{257-264}$. 10 µg/mL) or complete medium (background control). Concanavalin A (10 µg/mL, Amersham Biosciences) was used as positive control for IFN-γ ELISpot and PMA/Ionomycin (2×10$^{-8}$ M and 7.5×10$^{-7}$ M, respectively, both from Sigma-Aldrich) as a positive control for IL-4-producing T cells (data not shown). After 16-18 hours of incubation for IFN-γ and 40-42 hours for IL-4 determination, cells were removed by washing plates three times followed by 2 hours incubation at 37° C. with the respective biotinylated detection antibody in 1×PBS (1 µg/mL for IFN-γ, 2 µg/mL for IL-4, BD Pharmingen). After washing, streptavidin-horseradish peroxidase conjugate was added (0.1 U/mL in 1×PBS, Roche Diagnostics). After a 30 min incubation at 37° C., plates were washed and the substrate was added (50 µL per well of a mixture of 0.8 mg/mL DAB, 0.4 mg/mL $NiCl_2$ and 0.015% $H_2O_2$ in 100 mM Tris (pH 7.5)). The reaction was stopped 10-30 min later by washing the plates with tap water. Dried plates were analysed using a BIOREADER 5000 and results were expressed as the number of cytokine-producing cells per 1×10$^6$ total cells (mean of triplicates±standard deviation).

4.3.2 Results

In the present experiment, the adjuvant effect of classical particulate IC31® and three novel nanoparticulate IC31® compositions on the immunogenicity of TRP-$2_{180-189}$ peptide (CD8$^+$T cell epitope) was compared in C57BL/6 (H-$2^b$) mice. The immunogenicity of the different vaccine/adjuvant compositions was determined by assessing the number of specific IFN-γ and IL-4 producing spleen cells from the vaccinated mice (based on ELISpot assay).

In summary, the novel nanoparticulate IC31® compositions (5 mM Tris, 5 mM $NH_4HCO_3$ or 20 mM Histidine buffer) induced comparable cellular immune responses against the TRP-$2_{180-189}$ peptide as those observed with the classical particulate IC31® formulation (in 10 mM Tris/135 mM NaCl buffer, FIG. 23).

4.4 Comparison of the Adjuvanticity of Classical IC31® and Nanoparticulate IC31® Compositions in Combination with the CD4$^+$Th Peptide CopN$_{226-240}$ in C57BL/6 Mice 4.4.1 Materials & Methods CopN$_{226-240}$ Peptide Chlamydial (*C. pneumoniae*) outer protein N-derived peptide (CopN$_{226-240}$; sequence DRYTYQDMAIVSSFL); dissolved in 100% DMSO at 20 mg/mL; Batch CPD2454). In addition to using classical IC31® as a positive control and as a reference to compare data generated from nanoparticulate IC31® compositions, Cholera Toxin (CT) was also used as a positive adjuvant control.

Vaccination of Mice

Five C57BL/6 mice per group (6-8 weeks of age, Janvier) were immunized subcutaneously (s.c.) in the flank with a total volume of 100 µL final vaccine composition per mouse. All animal experiments were conducted according to Austrian guidelines (BGB1 No 108/2000 & 136/2001). Compositions with CopN$_{226-240}$ were prepared to include 50 µg of peptide per dose. To prepare the compositions, the buffer system used in each nanoparticulate IC31® composition was first mixed with the peptide solution and then the desired dose of each IC31® composition was added. After mixing, the dose that was injected into each mouse included 100 nmol of KLK, 4 nmol of ODN1a and 50 µg of peptide.

Cell Preparation & ELISpot Assay

This procedure was carried out exactly as described in 4.1.1, with the exception of the restimulation treatments. In this experiment, cells were incubated in the presence of CopN$_{226-240}$ (10 µg/mL), recombinant CopN protein (5 µg/mL) and complete medium as an irrelevant control.

4.4.2 Results

In this experiment, the adjuvant effect of the classical particulate IC31® formulation and novel nanoparticulate IC31® compositions on the immunogenicity of CopN$_{226-240}$ peptide (CD4$^+$T cell epitope) was investigated in C57BL/6 (H-$2^b$) mice. The effect of the different vaccine/adjuvant compositions was demonstrated by the induction of antigen-specific IFN-γ production by spleen cells (based on ELISpot assay).

In summary, recall responses, as assessed by IFN-γ production, to recombinant CopN protein and to the CopN$_{226-240}$ peptide by spleen cells from mice immunized with peptide formulated in three novel nanoparticulate IC31® compositions (5 mM Tris, 5 mM $NH_4HCO_3$, and 20 mM Histidine) were comparable to those observed in splenocytes from mice immunized with peptide adjuvanted with the classical IC31® formulation (in 10 mM Tris/135 mM NaCl) (FIG. 24). Similar numbers of $CopN_{226-240}$-specific IFN-γ-producing $CD4^+T$ cells were evident in the spleens of mice immunized with peptide adjuvanted in cholera toxin.

4.5 Adjuvanticity of Nanoparticulate IC31® in Combination with the $CD8^+CTL$ Peptide $TRP-2_{180-189}$ in C57BL/6 Mice 4.5.1 Materials & Methods $TRP-2_{180-189}$ Peptide Mouse tyrosinase-related protein derived peptide (sequence SVYDFFVWL); dissolved in 100% DMSO; Batch No. MG 27/09/2006

Vaccination of Mice

Five C57BL/6 mice per group (6-8 weeks of age, Janvier) were immunized with 60 μg $TRP-2_{180-189}$ peptide alone, 60 μg $TRP-2_{180-189}$ peptide adjuvanted with nanoparticulate IC31® (100 nmol KLK/4 nmol ODN1a per mouse) formulated in 2.5 mM Tris, pH 7.0, or nanoparticulate IC31® alone. Immunizations were delivered intradermally (i.d.) at the base of the tail in a total volume of 100 μL final vaccine composition per mouse, in two injections of 50 μl each. Mice were given booster vaccinations on days 13 and 28. Spleens and draining lymph nodes were harvested 2 weeks after the last booster. All animal experiments were conducted according to Austrian guidelines (BGB1 No 108/2000 & 136/2001).

Cell preparation & ELISpot Assay

This procedure was carried out exactly as described in 4.1.1, with the exception of the restimulation treatments and lymph node cell preparation (see below). In this experiment, cells were incubated with $TRP-2_{130-139}$ (1 μg/mL), an irrelevant control peptide ($SVN_{19-28}$, 1 μg/mL) or complete medium (background control).

Draining lymph nodes were removed and placed in complete medium. Lymph nodes were pooled by experimental group. A single cell suspension of lymph node cells was prepared under aseptic conditions by mechanical disaggregation through 200-mesh cell strainer using the bottom of a syringe plunger. The cell strainer and the plunger were rinsed with complete medium into a Petri-dish and the lymph node cells were resuspended and transferred to a tube. After washing by centrifugation, lymph node cells were resuspended in fresh complete medium and viable cell counts were performed by exclusion of 0.5% trypan blue.

ELISpot plates were coated with IFN-γ-specific capture anti-bodies (1 μg/mL, BD Pharmingen) in 0.1 M $NaHCO_3$ (pH 9.2-9.5) overnight at 4° C. On the next day, plates were blocked for 1 hour at 37° C. with 1×PBS/1% BSA. Freshly prepared cells were plated at $5×10^5$ cells per well in triplicates. Plates were incubated at 37° C./5% $CO_2$ in the presence of $TRP-2_{130-189}$ (1 μg/mL), an irrelevant control peptide ($SVN_{19-28}$, 1 μg/mL) or complete medium (background control). Concanavalin A (10 μg/mL, Amersham Biosciences) was used as positive control for IFN-γ production (data not shown). After 16-18 hours of incubation, cells were removed by washing plates three times followed by 2 hours incubation at 37° C. with biotinylated IFN-γ detection antibody in 1×PBS (1 μg/mL, BD Pharmingen). After washing, streptavidin-horseradish peroxidase conjugate was added (0.1 U/mL in 1×PBS, Roche Diagnostics). After a 30 min incubation at 37° C., plates were washed and the substrate was added (50 μL per well of a mixture of 0.8 mg/mL DAB, 0.4 mg/mL $NiCl_2$ and 0.015% $H_2O_2$ in 100 mM Tris, pH 7.5). The reaction was stopped 10-30 min later by washing the plates with tap water. Dried plates were analysed using a BIOREADER 5000 and results were expressed as the number of IFN-γ-producing cells per $1×10^6$ total cells (mean of triplicates±standard deviation).

Analysis of Granzyme B Upregulation by $CD8^+$ Spleen Cells

To further determine the antigen-specific activation of spleen cells from the immunized groups as prepared above, total spleen cells were stained with fluorescently-labelled antibodies to assess Granzyme B surface expression on $CD8^+$ cells (anti-mouse Granzyme B-PE, clone 16G6, eBioscience; anti-mouse CD8-APC, clone 53-6.7, BD Pharmingen). Samples were assessed by flow cytometry using the FACSCalibur instrument.

Isolation of CD8+ Lung Cells and Cytometric Bead Array (CBA)

Lungs were removed from mice of the same experimental groups as for spleen and lymph node cell preparation above and placed in cell culture medium. Single cell suspensions of the lungs were prepared by pressing lung tissue through 100-μm mesh cell strainers with a syringe plunger. Lung mononuclear cells were isolated by the use of Lymphocyte Separation Medium and cell counts were determined by trypan blue exclusion. From the resulting cells, $CD8^+$ cells were isolated by negative selection using immunomagnetic beads following the manufacturer's instructions (Miltenyi Biotec). The resulting enriched $CD8^+$ cell population was checked for purity by flow cytometry before use in the CBA assay.

Antigen-stimulated production of a variety of cytokines by these isolated $CD8^+$lung cells was assessed by Cytometric Bead Array (CBA, mouse Th1/Th2 10-plex kit, eBioscience). Isolated cells as prepared above were plated and stimulated for 48 hrs at 37° C./5% $CO_2$ in the presence of $TRP-2_{180-189}$ (1 μg/mL), $SVN_{19-28}$ (irrelevant control peptide, 1 μg/mL) or complete medium (background control). Concanavalin A (10 μg/mL, Amersham Biosciences) was used as positive control (data not shown). After stimulation, cells were isolated and analyzed for cytokine production according to the manufacturer's protocol. Samples were measured by flow cytometry using the FACSCalibur instrument. A total of 1500 events were acquired. The data was analyzed by using the FlowCytomix Pro Software.

4.5.2 Results

In the present experiment, the adjuvant effect of a novel nanoparticulate IC31® composition on the immunogenicity of $TRP-2_{180-189}$ peptide ($CD8^+T$ cell epitope) was tested in C57BL/6 (H-$2^b$) mice. The immunogenicity of the composition was determined by assessing the number of antigen-specific IFN-γ-producing spleen cells and lymph node cells from the vaccinated mice (based on ELISpot assay), by assessing Granzyme B expression on spleen cells by flow cytometry, and by measuring antigen-specific cytokine production by spleen cells by cytokine bead array.

In summary, the nanoparticulate IC31® composition tested induced cellular immune responses against the $TRP-2_{180-189}$ peptide as shown by increased numbers of IFN-γ-producing spleen cells and lymph node cells (ELISpot assay; FIG. 25A). Additionally, the cytolytic marker, Granzyme B, was upregulated by $TRP-2_{180-189}$ peptide on 2.2% of $CD8^+$ spleen cells isolated from mice immunized with $TRP-2_{180-189}$ peptide in combination with IC31® nanoparticles (FIG. 25B). Finally, the $TRP-2_{180-189}$ peptide-stimulated production of IFN-γ, TNF-α, GM-CSF, IL-6, IL-2 and IL-10 by $CD8^+$ cells isolated from the lungs of this experimental group was shown by Cytometric Bead Array (Table 13). This result indicates that IC31® nanoparticle formulations delivered intradermally have the capacity to stimulate mucosal immune responses.

TABLE 13

Production of cytokines by CD8+ cells from the lungs of vaccinated mice. Cells were isolated, stimulated with the indicated treatments and the production by these cells of IFN-γ, TNF-α, GM-CSF, IL-6, IL-2 and IL-10 was quantified by cytometric bead array. The concentrations of the respective cytokines are reported in pg/mL.

| | | Immunizations (d0, d13, d28) | | |
|---|---|---|---|---|
| Cytokine | Treatment | TRP-2$_{180\text{-}188}$ | TRP-2$_{180\text{-}188}$ + IC31® | IC31® |
| IFN-γ | Medium | 41 | 37 | 47 |
| | TRP-2$_{180\text{-}188}$ | 301 | >23880 | 249 |
| | SVN$_{19\text{-}28}$ | 199 | 70 | 74 |
| TNF-α | Medium | 14 | n.d.* | 2 |
| | TRP-2$_{180\text{-}188}$ | 24 | 87 | 4 |
| | SVN$_{19\text{-}28}$de | 9 | n.d. | n.d. |
| GM-CSF | Medium | 46 | 26 | 57 |
| | TRP-2$_{180\text{-}188}$ | 48 | 296 | 54 |
| | SVN$_{19\text{-}28}$ | 57 | 57 | 3 |
| IL-6 | Medium | 109 | 350 | 697 |
| | TRP-2$_{180\text{-}188}$ | 185 | 851 | 722 |
| | SVN$_{19\text{-}28}$ | 115 | 399 | 725 |
| IL-2 | Medium | n.d. | n.d. | 56 |
| | TRP-2$_{180\text{-}188}$ | 33 | 188 | 33 |
| | SVN$_{19\text{-}28}$ | 43 | 21 | 78 |
| IL-10 | Medium | n.d. | 76 | 88 |
| | TRP-2$_{180\text{-}188}$ | 56 | 217 | 88 |
| | SVN$_{19\text{-}28}$ | n.d. | 119 | 125 |

*n.d. = not detected

4.6 Adjuvanticity of Nanoparticulate IC31® in Combination with the CD8+CTL Peptide SVN$_{19\text{-}28}$ in C57BL/6 Mice

4.6.1 Materials & Methods

SVN$_{19\text{-}28}$ Peptide

Mouse Survivin-derived peptide (sequence IATFKN-WPFL); dissolved in 100% DMSO.

Vaccination of Mice

Five C57BL/6 mice per group (6-8 weeks of age, Janvier) were immunized with 60 µg SVN$_{19\text{-}28}$ peptide alone, 60 µg SVN$_{19\text{-}28}$ peptide adjuvanted with nanoparticulate IC31® (100 nmol KLK/4 nmol ODN1a per mouse) formulated in 2.5 mM Tris, pH 7.0, or nanoparticulate IC31® alone. Immunizations were delivered intradermally (i.d.) at the base of the tail in a total volume of 100 µL final vaccine composition per mouse, in two injections of 50 µl each. Mice were given booster vaccinations on days 13 and 28. Spleens and draining lymph nodes were harvested 2 weeks after the last booster. All animal experiments were conducted according to Austrian guidelines (BGB1 No 108/2000 & 136/2001).

Cell Preparation & ELISpot Assay

This procedure was carried out exactly as described in 4.1.1, with the exception of the restimulation treatments (see below) and lymph node cell preparation (see 4.5.1). In this experiment, cells were incubated with SVN$_{19\text{-}23}$ (1 µg/mL), an irrelevant control peptide (TRP-2$_{180\text{-}189}$, 1 µg/mL) or complete medium (background control).

ELISpot plates were coated with IFN-γ-specific capture anti-bodies (1 µg/mL, BD Pharmingen) in 0.1 M NaHCO$_3$ (pH 9.2-9.5) overnight at 4° C. On the next day, plates were blocked for 1 hour at 37° C. with 1×PBS/1% BSA. Freshly prepared cells were plated at 5×10$^5$ cells per well in triplicate. Plates were incubated at 37° C./5% CO$_2$ in the presence of SVN$_{19\text{-}23}$ (1 µg/mL), an irrelevant control peptide (TRP-2$_{180\text{-}189}$, 1 µg/mL) or complete medium (background control). Concanavalin A (10 µg/mL, Amersham Biosciences) was used as positive control for IFN-γ production (data not shown). After 16-18 hours of incubation, cells were removed by washing plates three times followed by 2 hours incubation at 37° C. with biotinylated IFN-γ detection antibody in 1×PBS (1 µg/mL, BD Pharmingen). After washing, streptavidin-horseradish peroxidase conjugate was added (0.1 U/mL in 1×PBS, Roche Diagnostics). After a 30 min incubation at 37° C., plates were washed and the substrate was added (50 µL per well of a mixture of 0.8 mg/mL DAB, 0.4 mg/mL NiCl$_2$ and 0.015% H$_2$O$_2$ in 100 mM Tris, pH 7.5). The reaction was stopped 10-30 min later by washing the plates with tap water. Dried plates were analysed using a BIOREADER 5000 and results were expressed as the number of IFN-γ-producing cells per 1×10$^6$ total cells (mean of triplicates±standard deviation).

4.6.2 Results

In the present experiment, the adjuvant effect of a novel nanoparticulate IC31® composition on the immunogenicity of SVN$_{19\text{-}28}$ peptide (CD8+T cell epitope) was tested in C57BL/6 (H-2$^b$) mice. The immunogenicity of the composition was determined by assessing the number of antigen-specific IFN-γ-producing spleen cells and lymph node cells from the vaccinated mice (based on ELISpot assay).

In summary, the nanoparticulate IC31® composition tested induced cellular immune responses against the SVN$_{19\text{-}28}$ peptide as assessed by increased numbers of IFN-γ-producing spleen cells and lymph node cells (FIG. 26).

The invention claimed is:

1. Pharmaceutical composition in an aqueous mixture form comprising a peptide with the amino acid sequence KLKL$_5$KLK (SEQ ID NO:1) and an oligodeoxynucleotide with the nucleic acid sequence (dIdC)$_{13}$ (SEQ ID NO:2) wherein the peptide and the oligodeoxynucleotide are present as stable complexes, characterized in that
- the peptide is present at a concentration of at least 100 nmol/mL and the oligodeoxynucleotide is present at a concentration of at least 4 nmol/mL,
- molar ratio of the peptide to the oligodeoxynucleotide is between 20:1 and 50:1,
- mean particle size of the stable complexes comprising the peptide and the oligodeoxynucleotide is less than 1 μm,
- sodium ion concentration is from 0 to 25 mM,
- the composition optionally comprises Ca2+ ions, phosphate ions, citrate ions, or acetate ions at a concentration of less than 1 mM each,
- the composition comprises 3 to 10 mM of Tris (Tris(hydroxymethyl)aminomethane) buffer with a pH of 6 to 7.2, 3 to 20 mM of Histidine buffer with a pH of 6 to 7, or 5 to 10 mM of ammonium bicarbonate buffer with a pH of 7 to 8,
- optionally, the composition has a viscosity less than 15 cP, and
- optionally, the composition is sterile.

2. Composition according to claim 1, characterized in that the pharmaceutical composition is a vaccine and contains an antigen.

3. Composition according to claim 1, characterized in that the pharmaceutical composition contains an antigen of a human pathogen.

4. Composition according to claim 1, characterized in that the pharmaceutical composition contains one or more carbohydrates.

5. Composition according to claim 3, wherein the antigen is derived from Influenza virus, Hepatitis A, B or C virus (HAV, HBV, HCV), Human Papilloma virus (HPV), Human Immunodeficiency virus (HIV), Herpes Simplex virus (HSV), Parvovirus B19, Tick Borne Encephalitis virus (TBEV), Dengue virus (DENY), Japanese Encephalitis virus (JEV), West Nile virus (WNV), Yellow Fever virus (YFV), Cytomegalovirus (CMV), *Mycobacterium tuberculosis, Staphylococcus aureus, Staphylococcus epidermidis, Helicobacter pylori, Streptococcus pyogenes, Streptococcus agalactiae, Chlamydia pneumoniae, Chlamydia trachomatis, Streptococcus pneumoniae, Klebsiella pneumoniae, Neisseria meningitidis, Borrelia burgdorferi, Borrelia afzelii, Borrelia garinii, Haemophilus influenzae, Moraxella catarrhalis, Enterococcus faecalis, Enterococcus faecium, Escherichia coli, Clostridium difficile, Shigella flexneri, Campylobacter jejuni, Plasmodium falciparum, Plasmodium vivax, Aspergillus* spp. or *Candida albicans*.

6. The pharmaceutical composition according to claim 2, wherein the antigen is a peptide or a polypeptide.

7. The pharmaceutical composition according to claim 3, wherein the antigen of a human pathogen is from a virus, a bacterium, a fungus or a parasite.

8. The pharmaceutical composition according to claim 7, wherein the antigen of a human pathogen is selected from the group comprising a CD8+ CTL peptide, a CD4+ Th peptide, a polypeptide, a protein, a glycoprotein, a lipoprotein, a virus particle and a whole cell or a subunit thereof.

9. The pharmaceutical composition according to claim 4, wherein the one or more carbohydrates are sucrose and/or sorbitol.

10. The pharmaceutical composition according to claim 1, wherein the composition is sterilized by filtration.

* * * * *

UNITED STATES PATENT AND TRADEMARK OFFICE
CERTIFICATE OF CORRECTION

PATENT NO. : 8,765,148 B2
APPLICATION NO. : 13/578686
DATED : July 1, 2014
INVENTOR(S) : Benjamin Wizel et al.

Page 1 of 2

It is certified that error appears in the above-identified patent and that said Letters Patent is hereby corrected as shown below:

On the Title Page, item (54) and in the Specification, column 1 should read as follows:

IC31 NANOPARTICLES

In the claims:

Claim 1, column 51, line 13, should read:

1. Pharmaceutical composition in an aqueous mixture form comprising a peptide with the amino acid sequence $KLKL_5KLK$ (SEQ ID NO: 1) and an oligodeoxynucleotide with the nucleic acid sequence $(dIdC)_{13}$ (SEQ ID NO:2) wherein the peptide and the oligodeoxynucleotide are present as stable complexes, characterized in that
 - the peptide is present at a concentration of at least 100 nmol/mL and the oligodeoxynucleotide is present at a concentration of at least 4 nmol/mL,
 - molar ratio of the peptide to the oligodeoxynucleotide is between 20:1 and 50:1,
 - mean particle size of the stable complexes comprising the peptide and the oligodeoxynucleotide is less than 1 μm,
 - sodium ion concentration is from 0 to 25 mM,
 - the composition optionally comprises $Ca^{2+}$ ions, phosphate ions, citrate ions or acetate ions at a concentration of less than 1 mM each,
 - the composition comprises 3 to 10 mM of Tris (Tris(hydroxymethyl)aminomethane) buffer with a pH of 6 to 7.2, 3 to 20 mM of Histidine buffer with a pH of 6 to 7, or 5 to 10 mM of ammonium bicarbonate buffer with a pH of 7 to 8,
 - optionally, the composition has a viscosity less than 15 cP, and Signed and Sealed this
Twenty-third Day of September, 2014

Michelle K. Lee
*Deputy Director of the United States Patent and Trademark Office*

CERTIFICATE OF CORRECTION (continued)
U.S. Pat. No. 8,765,148 B2

– optionally, the composition is sterile.

Claim 5, column 52, line 12, should read:

5. Composition according to claim 3, wherein the antigen is derived from Influenza virus, Hepatitis A, B or C virus (HAV, HBV, HCV), Human Papilloma virus (HPV), Human Immunodeficiency virus (HIV), Herpes Simplex virus (HSV), Parvovirus B19, Tick Borne Encephalitis virus (TBEV), Dengue virus (DENV), Japanese Encephalitis virus (JEV), West Nile virus (WNV), Yellow Fever virus (YFV), Cytomegalovirus (CMV), *Mycobacterium tuberculosis*, *Staphylococcus aureus*, *Staphylococcus epidermidis*, *Helicobacter pylori*, *Streptococcus pyogenes*, *Streptococcus agalactiae*, *Chlamydia pneumoniae*, *Chlamydia trachomatis*, *Streptococcus pneumoniae*, *Klebsiella pneumoniae*, *Neisseria meningitidis*, *Borrelia burgdorferi*, *Borrelia afzelii*, *Borrelia garinii*, *Haemophilus influenzae*, *Moraxella catarrhalis*, *Enterococcus faecalis*, *Enterococcus faecium*, *Escherichia coli*, *Clostridium difficile*, *Shigella flexneri*, *Campylobacter jejuni*, *Plasmodium falciparum*, *Plasmodium vivax*, *Aspergillus spp.* or *Candida albicans*.